United States Patent
Mercier et al.

(10) Patent No.: US 10,674,686 B2
(45) Date of Patent: Jun. 9, 2020

(54) **DOMINANT MUTATION IN THE *TDM* GENE LEADING TO DIPLOGAMETES PRODUCTION IN PLANTS**

(71) Applicant: INSTITUT NATIONAL DE LA RECHERCHE AGRONOMIQUE, Paris (FR)

(72) Inventors: Raphaël Mercier, Fontenay le Fleury (FR); Marta Cifuentes, Vanves (FR); Laurence Cromer, Clamart (FR)

(73) Assignee: Institut National de la Recherche Agronomique, Paris (FR)

( * ) Notice: Subject to any disclaimer, the term of this patent is extended or adjusted under 35 U.S.C. 154(b) by 376 days.

(21) Appl. No.: 15/308,807

(22) PCT Filed: Jun. 1, 2015

(86) PCT No.: PCT/EP2015/062174
§ 371 (c)(1),
(2) Date: Nov. 3, 2016

(87) PCT Pub. No.: WO2015/185514
PCT Pub. Date: Dec. 10, 2015

(65) Prior Publication Data
US 2017/0280645 A1    Oct. 5, 2017

(30) Foreign Application Priority Data

Jun. 2, 2014 (EP) .................................... 14305828

(51) Int. Cl.
| | | |
|---|---|---|
| *A01H 1/08* | (2006.01) | |
| *C12N 15/82* | (2006.01) | |
| *C07K 14/415* | (2006.01) | |
| *A01H 1/02* | (2006.01) | |
| *A01H 4/00* | (2006.01) | |

(52) U.S. Cl.
CPC .................. *A01H 1/08* (2013.01); *A01H 1/02* (2013.01); *A01H 4/008* (2013.01); *C07K 14/415* (2013.01); *C12N 15/8218* (2013.01); *C12N 15/8241* (2013.01); *C12N 15/8287* (2013.01)

(58) Field of Classification Search
None
See application file for complete search history.

(56) References Cited

U.S. PATENT DOCUMENTS

| 2004/0031072 A1* | 2/2004 | La Rosa ................ C07H 21/04 800/278 |
| 2007/0039067 A1 | 2/2007 | Feldmann et al. |
| 2007/0214517 A1 | 9/2007 | Alexandrov et al. |

FOREIGN PATENT DOCUMENTS

| WO | 97/30581 A1 | 8/1997 |
| WO | 2010/004431 A1 | 1/2010 |
| WO | 2010/079432 A1 | 7/2010 |
| WO | 2012/075195 A1 | 6/2012 |

OTHER PUBLICATIONS

Cromer et al (2012 PLoS Genetics 1-14 (Year: 2012).*
Cromer, L., et al., "OSD1 Promotes Meiotic Progression via APC/C Inhibition and Forms a Regulatory Network With TDM and CYCA1;2/TAM," PLoS Genetics 8(7):e1002865, Jul. 2012.
D'Erfurth, I., et al., "Turning Meiosis Into Mitosis," PLoS Biology 7(6):e1000124, Jun. 2009.
International Search Report dated Aug. 19, 2015, issued in corresponding International Application No. PCT/EP2015/062174, filed Jun. 1, 2015, 5 pages.
Ross, K.J., et al., "Cytological Characterization of Four Meiotic Mutants of *Arabidopsis* Isolated From T-DNA-Transformed Lines," Chromosome Research 5(8):551-559, Dec. 1997.
Wijnker, E., and A. Schnittger, "Control of the Meiotic Cell Division Program in Plants," Plant Reproduction 26(3):143-158, Sep. 2013.
Written Opinion dated Aug. 19, 2015, issued in corresponding International Application No. PCT/EP2015/062174, filed Jun. 1, 2015, 7 pages.

* cited by examiner

*Primary Examiner* — Brent T Page
(74) *Attorney, Agent, or Firm* — Christensen O'Connor Johnson Kindness PLLC

(57) ABSTRACT

The invention relates to a dominant mutation in the TDM gene leading to the production of 2n gametes in plants, to the plants comprising said mutation, and to their use in plant breeding. The invention relates also to plants in which the dominant mutation in the TDM gene is combined with the inactivation of a gene involved in meiotic recombination in plants and a gene involved in the monopolar orientation of the kinetochores during meiosis. These plants which produce apomeiotic gametes are also useful in plant breeding.

6 Claims, 10 Drawing Sheets

Figure 2:
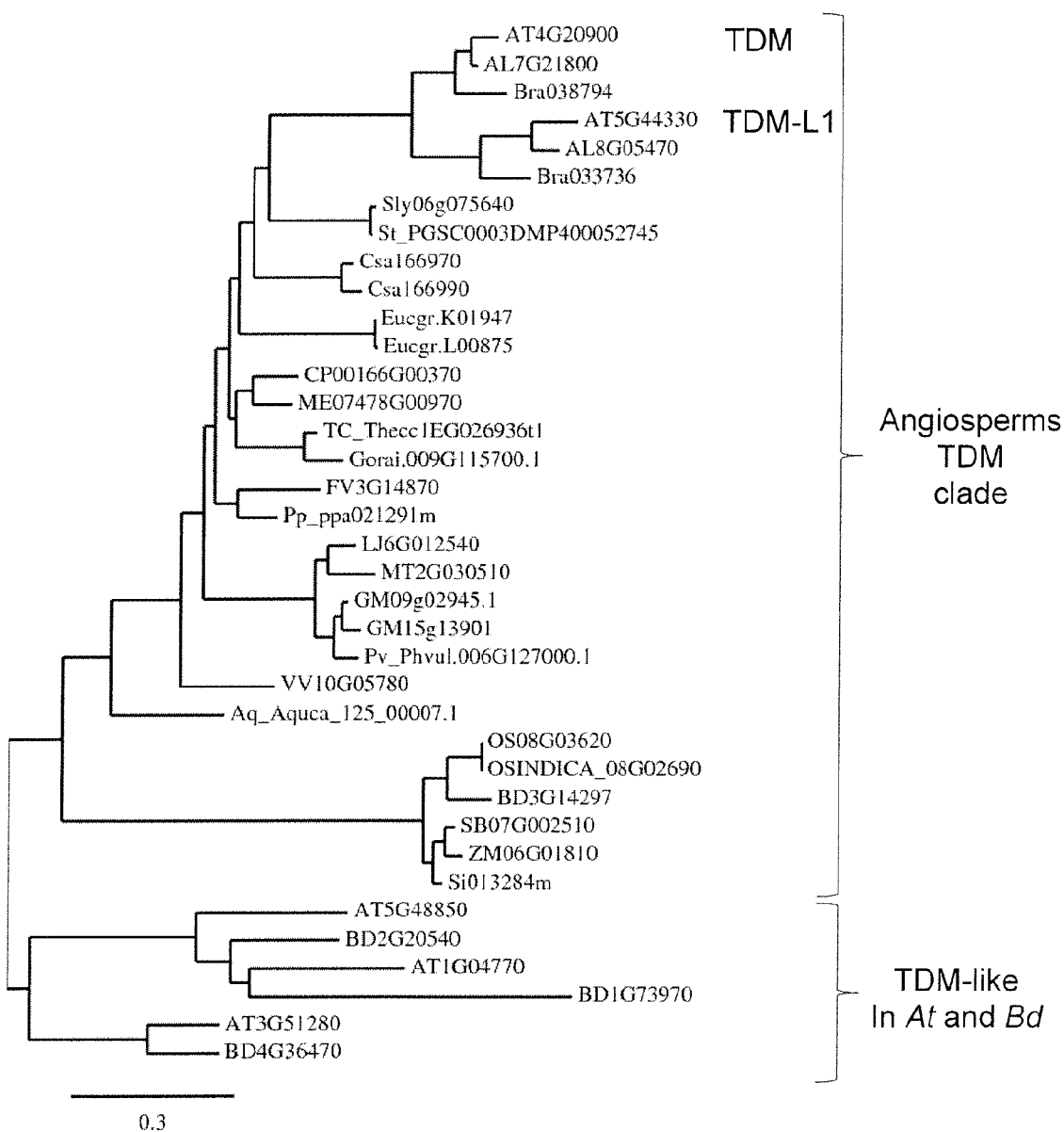

Specification includes a Sequence Listing.

| | | | | Domain of interest | |
|---|---|---|---|---|---|
| AT4G20900_TDM | 1 | MC------------PCV--ER---RA------------------------------------------------PP--GVYY | TPP | PA--- | 20 |
| AL7G21800 | 1 | MC------------PCE--ER---RA------------------------------------------------PP--GVYY | TPP | PA--- | 20 |
| Bra038794 | 1 | MC------------PFE--DR---RA------------------------------------------------PP--GVYW | TPP | PA--- | 20 |
| CP00166G00370 | 1 | -M------------WAN--DR---KP------------------------------------------------LG--RGFS | TPQ | PT--- | 19 |
| TC_Thecc1EG026936t1 | 1 | -M------------WSN--EK---NL------------------------------------------------PSRSRGFF | TPQ | PPA-- | 22 |
| ME07478G00970 | 1 | -M------------WSHH-EN---NI------------------------------------------------PA--RGFS | TPP | PS--- | 20 |
| FV3G14870 | 1 | -M------------WAR--DR---SY------------------------------------------------PP--AGFF | TPP | PP--- | 19 |
| GM09g02945.1 | 1 | ---------------MLF--ER---GS------------------------------------------------PA--RCYM | TPP | PQ-RT | 20 |
| GM15g13901 | 1 | ---------------MQF--ER---GS------------------------------------------------MA--RCYM | TPP | PQ-PP | 20 |
| LJ6G012540 | 1 | ---------------MPF--ER---NS------------------------------------------------PA--RCFM | TPP | PP-RL | 20 |
| MT2G030510 | 1 | ---------------MTF--ER---NS------------------------------------------------PA--RCYM | TPP | SSS-- | 19 |
| VV10G05780 | 1 | -M------------WSH--NN---NF------------------------------------------------PA--KGFS | TPP | PT--- | 19 |
| Csa166970 | 1 | -M------------LTNSGKN---KF------------------------------------------------LC--KGFS | TPP | PS--- | 21 |
| Csa166990 | 1 | -M------------WTNNSKN---NF------------------------------------------------PC--KGFL | TPP | PS--- | 21 |
| Eucgr.K01947 | 1 | -M------------WGN--RE---NF------------------------------------------------PA--RGYF | TPQ | PP--- | 19 |
| Eucgr.L00875 | 1 | -M------------WGN--RE---NF------------------------------------------------PA--RGYF | TPQ | PP--- | 19 |
| Aq_Aquca_125_00007.1 | 1 | -M------------GID--NK---KV------------------------------------------------GM--KGFS | TPP | PPP-- | 20 |
| Pv_Phvul.006G127000.1 | 1 | ---------------MLF--ER---GS------------------------------------------------PA--RCFV | TPP | PP--- | 18 |
| Pp_ppa021291m | 1 | -M------------WTR--DK---SL------------------------------------------------HT--RGFS | TPP | PT--- | 19 |
| Gorai.009G115700.1 | 1 | -M------------WSS--DK---HC------------------------------------------------PA--RGFL | TPQ | PPA-- | 20 |
| Sly06g075640 | 1 | -M------------WRNN-ERVYMT-------------------------------------------------PA--RGFL | TPP | PK--- | 22 |
| St_PGSC0003DMP400052745 | 1 | -M------------WRNN-ERVYMS-------------------------------------------------PA--RGFL | TPP | PK--- | 22 |
| Si013284m | 1 | -MPSGGRRLPPWTS--PR--SAGA--PR--------------------------WSPAAGTPVAGAGCGPV--SGYR | TPP | VS--- | 47 |
| BD3G14297 | 1 | -MRSGGRRLPPWTS--PR--GH----AAAEVVAPTGWSPR--TPAAG-GGGS---GSYV | TPP | LT--- | 49 |
| OS08G03620 | 1 | -MPSGGRRLPPWTS--PR--GA---APR---------------WSPC--TPAGADGS-GR--AAHA | TPP | AS--- | 43 |
| OSINDICA_08G02690 | 1 | -MPSGGRRLPPWTS--PR--GA---APR---------------WSPC--TPAGADGS-GR--AAHA | TPP | AS--- | 43 |
| SB07G002510 | 1 | -MPSGGRRLPPWTS--PR--SAGAGAAR--------------WSPAAGTPAAAGGQRSG--SGYG | TPP | LS--- | 49 |
| ZM06G01810 | 1 | -MPSGGRRLPPWTS--PR--SAGA--PM--------------WSTAGT-P---GGPRPG--PGYG | TPP | VS--- | 43 |

FIGURE 1

```
AT4G20900                     21  --RTSDD----VA-AMPMTERR----RPPYSCS---------S-S-S-ERRD-PFHIVHKVPSGDSPY  64
AL7G21800                     21  --RTSY-----VA-AMPLSERR----RPPFSCS---------S-S-S-EKRD-PFHIVHKVPSGDSPY  63
Bra038794                     21  --RRTEN-AAAM-PMPLSERR----RPP--------------S-S-EKRD-PFHIVHKVPSGDSPY   61
CP00166G00370                 20  --WNSRP-RDSL-VMPMSERK----SS---------------S-P-V-HKGD-LFHVVHKVPAGDSPY 60
TC_Thecc1EG026936t1           23  --WKKAQ----SS-VLPMSERK----RI--------------S-P-A-DQAD-SFHVIHKVPASDSPY 61
ME07478G00970                 21  --WKSPH--CLA-AMPMSERK----SV---------------S-S-G-CKRD-LFHVIHKVPAGDSPY 60
FV3G14870                     20  --RKSGP-P--N-PPPMSERK----RV---------------S-P-AAARSD-LFHVAHKVPAGDSPY 59
GM09g02945.1                  21  SPWKPPH-SRSS-SVPFSERK----MSP--------------N-S-V-NKSD-IFHIIHKVPAGDSPY 64
GM15g13901                    21  SSWKPPH-SQSP-SVPFSERK----KSP--------------N-S-A-NKID-LFHIIHKVPAGDSPY 64
LJ6G012540                    21  SSWRSTP-SRSPIMMPLSERK----RS---------------S-P-NKDD-PYHVIHKVPAGDSPY   63
MT2G030510                    20  SSWKSRP-VRSP-TVPFSERK----KSP--------------S-P-NKDD-LFHVIHKVPSGDSPY   64
VV10G05780                    20  --WKSKA-SFSS-ATPVSEKT----R----------------AAS-V-SKDD-LFHVIHKVPAGDSPY 59
Csa166970                     22  --WKWKPFRLPK-TAPFSESK----RLSP-------------S-M-A-NKDD-LFHVIHKVPAGDSPY 65
Csa166990                     22  --WKSGPFRSPK-TAPFSERK----RSSP-------------N-F-A-NKSD-LFHVIHKVPAGDSPY 65
Eucgr.K01947                  20  --KRAVR-PLVS-PVLMSERK----RA--------------------SPPD-LFHIIHKVPAGDSPY  57
Eucgr.L00875                  20  --KRATR-PLVS-PVLMSERK----RA--------------------SPPD-LFHIIHKVPAGDSPY  57
Aq_Aquca_125_00007.1          21  LRWKSAP-CTPIQTLEMNEESLHQLS----------------A-T-I-AKVD-SFHIIHKVPSGDSPY 67
Pv_Phvu1.006G127000.1         19  SPWKTIS-SRSP-SVPFSERK----KSP--------------N-S-A-NKSD-IFHIIHKVPSGDSPY 62
Pp_ppa021291m                 20  --WKSGP-PNPP-MVPMSERK----RV---------------S-P-S-DGGD-LFHVMHKVPVGDSPY 60
Gorai.009G115700.1            21  --WKKVQ--STT-VLPMSERK----RI---------------S-P-A-NNGD-CFHVIHKVPASDSPY 60
Sly06g075640                  23  --WRS----------PATEKD----QKWP-TH----------A-Q-S-AKAD-LFHVIHKVPSGDSPY 59
St_PGSC0003DMP400052745       23  --WRS----------PASDKD----QRWP-TH----------A-Q-S-AKAD-LFHVIHKVPSGDSPY 59
Si013284m                     48  --AGGC-FGTRV-TPPTSGGA----RVT--------------PPS-TGG-CSSRPRPPPLDSPY     89
BD3G14297                     50  --AG-CCCSS------SSY------RVTP-PSSGGGCTSLLT-PPV-SGGGCSRPPRAPPAVVDSPY  98
OS08G03620                    44  --GG-C--SSHV-TPPASGGG----G---------CYGYRVT-PPT-SGG-CSRPPRAPLSSVDSPY  88
OSINDICA_08G02690             44  --GG-C--SSHV-TPPASGGG----G---------CYGYRVT-PPT-SGG-CSRPPRAPLSSVDSPY  88
SB07G002510                   50  --AG-C-FGTRV-TPPTSGGA----RVT--------------PPS-TGG-CSSRPRPPPSLDSPY    90
ZM06G01810                    44  --AG-C-FGTRV-TPPTSGGT----RVTP-PTSGGAGA-RVT-PPS-TGG-CSSRPRPPPSMDSPY   96
```

FIGURE 1(CONTINUATION)

```
AT4G20900              65  VRAKHAQLIDKDPNRAISLFWTAINAGDRVDSALKDMAVVMKQLGRSDEGIEAIKSFRYLCSFESQDS  132
AL7G21800              64  VRAKHAQLIDKDPNRAISLFWTAINAGDRVDSALKDMVVVMKQLDRSDEGIEAIRSFRYLCSFESQDS  131
Bra038794              62  VRAKHAQLVYKDPNRAISLFWAAINAGDRVDSALKDMAVFKKLDRSDEGIEAIKSFRYLCPFEAQDS  129
CP00166G00370          61  VRAKHVQLIEKDPSRAISLFWAAINAGDRIDSALKDMAVVMKQLNRSDEAIEAIKSFRHLCPYDAQES  128
TC_Thecc1EG026936t1    62  GRAKHVQLIDKDPSKAISLFWAAINAGDRVDSALKDMAVVMKQLNRSDEAIEAIKSFRHLCPHDSQES  129
ME07478G00970          61  VRAKHVQLIEKDPSRAISLFWAAINAGDRIDSALKDMAVVMKQLNRSDEAIEAIKSFRRLCPYDSQES  128
FV3G14870              60  VRAKQVQLIDKNPSKAISLFWAAINAGDRVDSALKDMAVVMKQLDRAEEAIEAIKSFRHLCPYESQES  127
GM09g02945.1           65  VKAKQVQLVDKDPGRAVSLFWAAINAGDRVESALKDMALVMKQLNRSDEAIEAIRSFRHLCPSDSQDS  132
GM15g13901             65  VKAKQVQLVDKDPGRAISLFWAAINARDRVESALKDMALVMKQLNRSDEAIEAIRSFRHLCPSDSRDS  132
LJ6G012540             64  VKAKQVQLVDKDPGKAISLFWAAINAGDRVESALKDMALVMKQLNRSDEAIEAIKSFRHLCPPDSQES  131
MT2G030510             65  VKAKQVQLVDKDPGKAISLFWAAINAGDRVESALKDMALVMKQLNRSDEAIEAIKSFRHLCPSDSQES  132
VV10G05780             60  VRAKQVQLIDKDPNRAISLFWAAINSGDRVDSALKDMAVVMKQLNRSDEAIEAIKSFRHLCPQESQES  127
Csa166970              66  VKAKQVQLIDKDPNRAVSLFWAAINAGDRVDSALKDMAVVMKQLDRSDEAIEAIKSFRHLCPYDSQES  133
Csa166990              66  VKAKQVQLIEKDPSRAVSLFWAAINAGDRVDSALKDMAIVMKQLNRSDEAIEAIKSFRHLCPFDSQES  133
Eucgr.K01947           58  VKAKRVQLIDKDPSKAISLFWAAINAGDRVDSALKDMAIVMKQLNRSDEAIEAIKSFRHLCPFDSQES  125
Eucgr.L00875           58  VKAKRVQLIDKDPSKAISLFWAAINAGDRVDSALKDMAIVMKQLNRSDEAIEAIKSFRHLCTPLSQES  125
Aq_Aquca_125_00007.1   68  VKAKHVQLIDKDPSKSVALFWSAINAGDRVESALKDMAIVMKQLDRSDEAIEAIRSFRHLCPSDSQDS  135
Pv_Phvul.006G127000.1  63  VKAKQVQLVDKDPGRAISLFWAAINAGDRVESALKDMALVMKQLNRSDEAIEAIRSFRHLCPSDSQES  130
Pp_ppa021291m          61  VRAKQVQLIEKDPSKAISLFWAAINAGDRVDSALKDMAIVMKQLNRSEEAIEAIKSFRHLCPHDSQES  128
Gorai.009G115700.1     61  GRAKHVQLIDKDPSKAVSLFWAAINAGDRVDSALKDMAIVMKQLNRSDEAIEAIKSFRHLCPYDSQES  128
Sly06g075640           60  VRAKHVQLIDKDPGKAISLFWAAINSGDRVDSALKDMAVVMKQLDRSDEAIEAIKSFRNLCPSESQES  127
St_PGSC0003DMP400052745 60 VRAKHVQLIDKDPGKAISLFWAAINSGDRVDSALKDMAVVMKQLDRSDEAIEAIKSFRNLCPSESQES  127
Si013284m              90  VRAKQAQVIEKDPNKAVPLFWAAINSGDRIESALKDMANVLKQANRAEEAIEAIRSFRDRCPYEAQDS  157
BD3G14297              99  VRAKQAQLIEKDPNKAVPLFWAAINSGERIESALKDMATVLKQANRAEEAIEAIRSFRDRCPNEAQDS  166
OS08G03620             89  VRAKQAQVIEKDPNKAVPLFWAAINSGDRIESALKDMATVLKQANRAEEAIEAIRSFRDRCPNEAQES  156
OSINDICA_08G02690      89  VRAKQAQVIEKDPNKAVPLFWAAINSGDRIESALKDMATVLKQANRAEEAIEAIRSFRDRCPNEAQES  156
SB07G002510            91  VRAKQAQIVEKDPNKAVPLFWAAINSGDRTESALKDMANVLKQANRAEEAIEAIRSFRDRCPYEAQES  158
ZM06G01810             97  VRAKQAQIVEKDPNKAVPLFWAAINSGDRIESALKDMANVLKQANRSEEAIEAIRSFRDRCPYEAQES  164
```

FIGURE 1(CONTINUATION)

```
AT4G20900               133  IDNLLLELYKKSGRIEEEAVLLEHKLQTLEQGMGFGGRVSRAKRVQGKHVIMTIEQEKARILGNLGWV  200
AL7G21800               132  IDNLLLELYKKSGRIEEEAELLEHKLKTLEQGMGFGGRVIRAKRVQGKHVIMTIEQEKARVLGNLGWV  199
Bra038794               130  IDNLLLELYKKSGRIQEEAELLEHKLKVIEQGMGFGGRIVRAKRVQGKHVIMTVEQEKARVLGNLGWV  197
CP00166G00370           129  LDNVIVELYKRSGRIEEVELLQHKLKNIE-GVTFGGKRTKTARSQGKKIQITVEQEKSRILGNLAWA  195
TC_TheccIEG02693GtI     130  IDNVIVELYKRSGRIEEEIEMLQNKLRNIEGGTVFGGKRTKIARSQGKKIQITIEQEKSRILGNLAWA  197
ME07478G00970           129  IDNVIVELYKRSGRIEEEIEMLHLKLKNIEEGIAFGGKRTKTARSQGKKIQITVEQERSRILGNLAWA  196
FV3G14870               128  LNNVIVELYKRAGRIEDEIETLQSKLKRMDEGIAFNGKRTKTARAQGKKVQITVEQERSRVLGNLAWA  195
GM09g02945.1            133  LDNIIVELYKRSGRVDEEIAMLCHKKLKQIEDGLTFVGRTTKQARSQGKKIQITAEQEISRILGNLAWA  200
GM15g13901              133  LDNIIVELYKRSGRIDEEIAMLHHKLKQIEDGLTFVGRTTKQARSQGKKIQITAEQEISRILGNLAWA  200
LJ6G012540              132  LDNIIVELYKRSGRVDEEISMLHHKLKQIEDGVTFVGRTTKQARSQGKKIHVTAEQEISRILGNLAWA  199
MT2G030510              133  LDNVIVELYKRSGRVDEEIGMLHQKLKQIEDGMTYVGRTTKHARSQGKKIQISAEQEISRILGNLAWA  200
VV10G05780              128  LDNVIVELYKRSGRLDEQIEMLQYKLKNIDEGSAFGGKRTKIARSQGKKIQISIEQEKSRLLGNLAWA  195
Csa166970               134  IDNVLIELYKRSGRIEEEIDMLQCKLKQIEDGTVFGGKRTKAARSQGKKVQITVEQEKSRVLGNLAWA  201
Csa166990               134  IDNVLIELYKRSGRIEEEIDMLQRKLKQIEDGTIFGGKRTKAARSQGKKVQITEEQEKSRVLGNLAWA  201
Eucgr.K01947            126  LDNVLIELYKRSGRIEEEIEMLQHKLRLIEEGKGFVANRTKTARSQGKKIQVTREQERSRIMGNLAWA  193
Eucgr.L00875            126  LDNVLIELYKRSGRIEEEIEMLQHKLRLIEEGKGFVANRTKTARSQGKKIQVTREQERSRIMGNLAWA  193
Aq_Aquca_125_00007.1    136  LDNVIVDLYKRGGRIEHIEEEIEMLIDDGVAFGGKTKIARSQGKKFLVSIDQERSRLLGNLGWA  203
Pv_Phvul.006G127000.1   131  LDNIVELFKRSGRVDEEISMLHHKLKLIEDGITFVGRTTKQARSQGKKIQITAEQEISRILGNLAWA  198
Pp_ppa021291m           129  LNNVIVELYKRAGRIEEEIEMLQSKLKHIDEGIAFGGKRTKTARSQGKKVQITVEQERSRILGNLAWA  196
Gorai.009G115700.1      129  LDNVIVELYKRSGRVDEEIEILLNKLRNIEEGTVFGGKKTKIARSQGKRTKIARSQGKKIQITEQEKSRILGNLAWA  196
Sly06g075640            128  IDNILIELYKRSGRLEEEIELLELELKLKNVEEGIAFGGKRTKIARSQGKKVQITIEKEYARLLGNLAWS  195
St_PGSC0003DMP400052745 128  IDNILIELYKRSGRLEEEIELLELELKLKNVEEGIAFGGKRTKIARSQGKKVQITIEKEYARLLGNLAWS  195
SiO13284m               158  LDNVLLDLYKKCGRTEQIEMLTIKLRVVDEELASGRWKTKLSKSHGRVVYLSKSHGRVVLSLRDEKARLLGNLAWA  225
BD3G14297               167  LDNILLDLYKKCGRTKEQIEMLTIKLRMVDEDLASGRWKTKLSKSHGRVVYLSLRDEKARLLGNLAWA  234
OS08G03620              157  LDNILLDLYKKCGRTKEQIEMLTLKLRIVDEELASGRWKTKLSKSHGRVVYLSLRDEKARLLGNLAWA  224
OSINDICA_08G02690       157  LDNILLDLYKKCGRTKEQIEMLTLKLRIVDEELASGRWKTKLSKSHGRVVYLSLRDEKARLLGNLAWA  224
SB07G002510             159  LDNILLDLYKKCGRTDEQIEMLTIKLRIVDEELASGRWKTKMSKSHGRVVYLSLRDEKARLLGNLAWA  226
ZM06G01810              165  LDNILLDLYKKCGRTDEQIEMLTLKLRIVDEELASGRWKTKLSKSHGRVVLSKSHGRVVLSLRDEKARLLGNLAWA  232
```

FIGURE 1(CONTINUATION)

| ID | Start | Sequence | End |
|---|---|---|---|
| AT4G20900 | 201 | HLQLHNYGIAEQHYRRALGLERDKNKLCNLAICLMRMSRIPEAKSLLDDVRDSPAESECG-DEPFAKS | 267 |
| AL7G21800 | 200 | HLQLHNYGIAEQHYRRALGLERDKNKLCNLAICLMRMGRIPEAKSLLDDVRDSPTESECG-DEPFAKS | 266 |
| Bra038794 | 198 | HLQLHNYGIAEQHYRRALCLEPDKNKQCNLAICLMRMGRIPEAKSMIDAVRDSSAETESG-DEPFTKS | 264 |
| CP00166G00370 | 196 | YLQQHNYGSAEQYYRKALSLEVDRNKQCNLAICLMHMNRIAEAKSLLAVRDSPKK-RQM-DESCAKS | 261 |
| TC_Thecc1EG026936t1 | 198 | YLQQHNYGIAEQHYRKALSLEPDMNKQCNLAICLMHMNRISEAKSLLQDVKASSGN-EQM-DESHSKS | 263 |
| ME07478G00970 | 197 | YLQHHDYGLAEQYYRKALSLEPDRNKQCNLAICLMHMNRIPEAKSLLQAVSDSCGS-KQM-DDSYAKS | 262 |
| FV3G14870 | 196 | YMQQGNYTTAEEHYKNALALEPDRNKQCNLAICLMHMNRITEARHLLQAVRDSAGN-KPM-DESYAKS | 261 |
| GM09g02945.1 | 201 | YLQKGDYKTAEEHYRKALSFEVDRNKQCNLAICLIHMNKIKEAKFLLQAVRTATKN-RKM-DDSFAKS | 266 |
| GM15g13901 | 201 | YLQKGDYKAAEEHYRKALSFEVDRNKQCNLAICLIHMNKIKEAKFLLQAVRTATKN-RKM-DDSFAKS | 266 |
| LJ6G012540 | 200 | YLQKGDYKAAEEHYRKALSFEVDRNKQCNLAICLMQTNRITEAKFLLQAVTTASKH-RKM-DDSCAKS | 265 |
| MT2G030510 | 201 | YLQKGDYKTAEEHYRKALSFEVDRNKQCNLAICLMQMNKVTEARFLLQAVTAATKN-RKM-DDSFVKS | 266 |
| VV10G05780 | 196 | YLQQGNYKTAGELYKQALALDPDRNKECNLAICLMYMNKIKEAKAMLYAIQVSSQN-GRM-DDSYVKS | 261 |
| Csa166970 | 202 | FLQLDNIYIAEEYYRKALSLESDNNKKCNLAICLILTNRLTEAKSLLQSVRASSGG-KPM-EESYAKS | 267 |
| Csa166990 | 202 | FLQLNNIYVAEDYYRKALSLEADNNKKCNLAICQILTNRLTEAKSLLQSVRASSGG-KPM-EESYAKS | 267 |
| Eucgr.K01947 | 194 | HLQLSNYEIAEGLYREALSLEPDKNKQCNLAICLMNMNKLADAKAVLDAVRGPCGD-GDM-DESYAKS | 259 |
| Eucgr.L00875 | 194 | HLQLSNYEIAEGLYREALSLEPDKNKQCNLAICLMNMNKLADAKAVLDAVRGPCGD-GDM-DESYAKS | 259 |
| Aq_Aquca_125_00007.1 | 204 | YMQQNDYKTAEEIYRKALSIEQDKNKQCNLAICLMNRGEIMEAKSLLQTVTPSSTE-REL-VDPFIKS | 269 |
| Pv_Phvul.006G127000.1 | 199 | YLQKEDYKTAEEHYRRALSFEVDRNKQCNLAICLMHMNKIKEAKFLLQAVRTATKN-RKM-DESFVKS | 264 |
| Pp_ppa021291m | 197 | YLQQGNYKTAEEYYMKSLSLELDRNKQCNLAICLMHMNKILAEAKSLLQVVRASSGN-KPM-DESYAKS | 262 |
| Gorai.009G115700.1 | 197 | YLQQHNYGIAEQHYRKALSLEPDKNKQCNLAICLMHMNRLGEAKSLLQDVKVSAGT-EEM-DESYSKS | 262 |
| Sly06g075640 | 196 | YMQLNNFKLAEEYYRKALSLESDKNKQSNLAICLMHMNKIAEARFLLQSIKTSDR--RQM-DESCTKS | 260 |
| St_PGSC0003DMP400052745 | 196 | YMQLNNFKLAEEYYRKALSLESDKNKQSNLAICLMHMNKIAEARFLLQSIKASDR--WQM-DESCTKS | 260 |
| Si013284m | 226 | HMQSENYEEAEMLYRQALAIEADYNKECNLAICLMKTGKLAEAKYLLQAIPYNCD------DESHVKS | 287 |
| BD3G14297 | 235 | HMQSENYEEAEMLYRQALAIEADYNKECNLAVCLMKTGKVAEAKYLLQAIPYNSS------DEKHVRS | 296 |
| OS08G03620 | 225 | HMQSENYDEAEMLYRQALAIEADYNKECNLAICLIKTGKVAEAKYLLQSIPDNCS------DESHVRS | 286 |
| OSINDICA_08G02690 | 225 | HMQSENYEAEMLYRQALAIEADYNKECNLAICLIKTGKVAEAKYLLQSIPDNCS------DESHVRS | 286 |
| SB07G002510 | 227 | YMQSENYEGAEMLYRQALAIEADYNKECNLAICLMKTGKVAEAKYLIQAIPYNCD------DESHVKS | 288 |
| ZM06G01810 | 233 | YMQSENYEEAEMLYRQALAIEADYNKECNLAICLMKTGKLAEAKYLIHAIPYNCN------DESHVKS | 294 |

FIGURE 1(CONTINUATION)

| | | | |
|---|---|---|---|
| AT4G20900 | 268 | YDRAVEMLAEIESKK 282 | [...] 434 |
| AL7G21800 | 267 | YDRAVEMLAEIESKN 281 | [...] 426 |
| Bra038794 | 265 | YNRAVEMLAEVESKD 279 | [...] 432 |
| CP00166G00370 | 262 | FERAYQILREKESQH 276 | [...] 670 |
| TC_Thecc1EG026936t1 | 264 | YERALDMLIQVESQS 278 | [...] 676 |
| ME07478G00970 | 263 | FERAVDILTELESKS 277 | [...] 631 |
| FV3G14870 | 262 | FERSFEMLTELEQQS 276 | [...] 673 |
| GM09g02945.1 | 267 | FERASQMLIEIETSS 281 | [...] 601 |
| GM15g13901 | 267 | FERASQMLIEIETSS 281 | [...] 602 |
| LJ6G012540 | 266 | FERASQMLMDMESSS 280 | [...] 603 |
| MT2G030510 | 267 | YERATQMLQEMESTA 281 | [...] 617 |
| VV10G05780 | 263 | FERASQVLTELEANS 276 | [...] 673 |
| Csa166970 | 268 | FERASHMLAEKESKS 282 | [...] 773 |
| Csa166990 | 268 | FERAFHMLTEKESKS 282 | [...] 683 |
| Eucgr.K01947 | 260 | FDRALQMLNEIKSRP 274 | [...] 644 |
| Eucgr.L00875 | 260 | FDRALQMLNEIKSLP 274 | [...] 634 |
| Aq_Aquca_125_00007.1 | 270 | FDRAYEMLIELESKS 284 | [...] 689 |
| Pv_Phvul.006G127000..1 | 265 | FERASQMLVEIETSS 279 | [...] 625 |
| Pp_ppa021291m | 263 | FERAIQMLTELEAKS 277 | [...] 758 |
| Gorai.009G115700.1 | 263 | YERAMEILMQVETQS 277 | [...] 649 |
| Sly06g075640 | 261 | FERATQMLAELESHG 275 | [...] 614 |
| St_PGSC0003DMP400052745 | 261 | FERATQMLAELETHG 275 | [...] 614 |
| Si013284m | 288 | LSRATEMLRDLELQS 302 | [...] 683 |
| BD3G14297 | 297 | FARATEMIKELESQA 311 | [...] 717 |
| OS08G03620 | 287 | LARAREMLMELESPT 301 | [...] 815 |
| OSINDICA_08G02690 | 287 | LARAREMLMELESPT 301 | [...] 813 |
| SB07G002510 | 289 | LSRATEMLRELELQS 303 | [...] 685 |
| ZM06G01810 | 295 | LSRATEMLREFDLQS 309 | [...] 690 |

FIGURE 1(CONTINUATION)

DOMINANT MUTATION IN THE *TDM* GENE LEADING TO DIPLOGAMETES PRODUCTION IN PLANTS

The sequence listing associated with this application is provided in text format in lieu of a paper copy and is hereby incorporated by reference into the specification. The name of the text file containing the sequence listing is 56972_Sequence_Revised_final_2016-11-17. The text file is 186 KB; was created on Nov. 17, 2016; and is being submitted via EFS-Web with the filing of the specification.

The invention relates to a dominant mutation in the TDM gene leading to the production of 2n gametes in plants, to the plants comprising said mutation, and to their use in plant breeding. The invention relates also to plants in which the dominant mutation in the TDM gene is combined with the inactivation of a gene involved in meiotic recombination in plants and a gene involved in the monopolar orientation of the kinetochores during meiosis. These plants which produce apomeiotic gametes are also useful in plant breeding.

Meiosis is a key step in the life cycle of sexually reproducing eukaryotes such as the majority of flowering plants.

In normal meiosis, chromosomes first duplicate, resulting in pairs of sister chromatids. This round of replication is followed by two rounds of division, known as meiosis I and meiosis II. During meiosis I homologous chromosomes recombine and are separated into two cell compartments, each of them comprising one entire haploid content of chromosomes. In meiosis II the two sets of chromosomes resulting from meiosis I further divide, and the sister chromatids segregate. The four spores resulting from this division are thus haploid (n) and carry recombined genetic information.

By comparison, during mitosis in diploid cells, chromosomes replicate and sister chromatids segregate to generate daughter cells that are diploid (2n) and genetically identical to the initial cell.

Abnormal gametes resulting from anomalies during meiosis have been shown to be useful for the genetic improvement of several plants of interest, including crops (for review, cf. for instance RAMANNA & JACOBSEN, Euphytica 2003, 133, 3-18,). In particular, 2n and apomeiotic gametes are useful for producing polyploids plants, or for crossing plants of different ploidy level, for instance tetraploid crop plants and their diploid wild relatives, in order to use their genetic diversity in plant breeding programs. They can also be used in methods of genetic mapping. Apomeiotic gametes are also of interest for the production of apomictic plants, i.e., plants which are able to form seeds from the maternal tissues of the ovule, resulting in progeny that are genetic clones of the maternal parent.

2n gametes (also known as diplogametes) are gametes having the somatic chromosome number rather than the gametophytic chromosome number. The abnormalities leading to 2n gametes formation include in particular abnormal cytokinesis, the skip of the first or second meiotic division, or abnormal spindle geometry (for review cf. Veilleux, *Plant Breeding Reviews*, 1985, 3, 252-288, or Bretagnolle & Thompson, *New Phytologist*, 1995, 129, 1-22). These abnormalities lead to different classes of unreduced gametes. For instance, skipping of the first meiotic division results in First Division Restitution (FDR) gametes, while absence of the second meiotic division results in Second Division Restitution (SDR) gametes. Numerous mutants that are able to produce 2n gametes have been reported in various plant species. However, the mutations involved in the formation of diplogametes in these plants have not been characterized.

Apomeiotic gametes are gametes which are genetically identical to the initial cell, retaining all parent's genetic information. Apomeiotic gametes production is one of the key components of apomixis (Bicknell & Koltunow, Plant Cell, 2004, 16, S228-45). Although, over 400 species of plant are apomictic, these include few crop species. Furthermore, attempts to introduce this trait by crossing have failed ("The Flowering of Apomixis: From Mechanisms to Genetic Engineering", 2001; Editor: Savidan et al.; Publisher: CIMMYT, IRD, European Commission DG VI (FAIR), MEXICO, 2001. Spillane et al., Sexual Plant Reproduction, 2001, 14, 179-187).

To date, only a few genes implicated in the formation of 2n or apomeiotic pollen have been identified.

The inactivation of AtPS1 (*Arabidopsis thaliana* PARALLEL SPINDLES) generates diploid male spores, giving rise to viable diploid pollen grains with recombined genetic information and to spontaneous triploid plants in the progeny (WO 2010/004431; d'Erfurth et al., *PLoS Genet.*, 2008, 4, e1000274).

The inactivation of TAM (TARDY ASYNCHRONOUS MEIOSIS, also known as CYCA1;2) or of OSD1 (OMISSION OF SECOND DIVISION) leads to a premature exit from meiosis after meiosis I, and thus the production of diploids spores and SDR gametes with recombined genetic information (d'Erfuth et al., *PLoS Genet.*, 2010, 6, e1000989; d'Erfuth et al., *PLoS Biol.*, 2009, 7, e1000124; WO 2010/079432).

SPO11-1 encodes a protein necessary for efficient meiotic recombination in plants, and whose inhibition eliminates recombination and pairing (Grelon et al., *Embo J.*, 2001, 20, 589-600), and REC8 (At2g47980) encodes a protein necessary for the monopolar orientation of the kinetochores during meiosis (Chelysheva et al., *J. Cell. Sci.*, 2005, 118, 4621-32), and whose inhibition modifies chromatid segregation. The Atspo11-1 mutant undergoes an unbalanced first division followed by a second division leading to unbalanced spores and sterility. The Atspo11-1/Atrec8 double mutant undergoes a mitotic-like division instead of a normal first meiotic division, followed by an unbalanced second division leading to unbalanced spores and sterility (Chelysheva et al., *J. Cell. Sci.*, 2005, 118, 4621-32).

In the triple osd1/spo11-1/rec8 mutant, the presence of the spo11-1 and rec8 mutations leads to a mitotic-like first meiotic division and the presence of the osd1 mutation prevents the second meiotic division from occurring. Thus meiosis is totally replaced by mitosis without affecting subsequent sexual processes. Thus, the osd1/spo11-1/rec8 mutant is named MiMe for Mitosis instead of Meiosis (d'Erfuth et al., *PLoS Biol.*, 2009, 7, e1000124 and WO 2010/079432). The spores and gametes obtained from the MiMe mutant are genetically identical to the initial cell.

To date, the engineering of plants able to produce 2n or apomeiotic gametes is thus restricted to a limited number of genes.

Therefore, to increase the number of genes which can be modified to produce high frequency of 2n or apomeiotic gametes, there is a need for other genes implicated in the formation of these gametes in plants.

The TDM (THREE-DIVISION MUTANT) gene, also designated as TDM1, MS5 (PROTEIN MALE STERILE 5) or POLLENLESS 3, encodes a protein which belongs to a small protein family conserved in plants. The sequence of the TDM gene of *Arabidopsis thaliana* is available in the TAIR database under the accession number At4g20900, or in the GenBank database under the accession number NC_003075.7. It encodes a protein of 434 amino acids (aa) whose sequence is represented in the enclosed sequence listing as SEQ ID NO: 1.

The TDM gene is described as required at the end of meiosis to exit meiosis II. TDM mutation leads to formation of polyads and male sterility caused by entry into an aberrant third meiotic division after normal meiosis I and II. The tdm mutants were shown to carry a mutation resulting in a gene which encodes a truncated TDM protein lacking 305 or 112 amino acids at its C-terminus (Bulankova et al., The Plant Cell, 2010, 22, 3791-3803; Cromer et al., PLoS Genet., 2012, 8, e10028652012; Glover et al., The Plant Journal, 1998, 15, 345-356; Ross et al., Chrom. Res., 1997, 5, 551-559; WO/9730581).

In contrast, as shown herein, the inventors have identified dominant mutations in the TDM gene which lead to the premature exit from meiosis before meiosis II and consequently to the production of diploid male and female SDR gametes and diploids spores with recombined genetic information. In addition, they have shown that the introduction of a dominant mutation in the TDM gene of a spo11-1 rec8 double mutant results in a MiMe mutant.

The inventors have thus identified another gene implicated in the formation of 2n and apomeotic gametes in plants.

Compared to the other mutations involved in diplogametes production which are recessive and thus require an additional step of self-fertilizing the primary mutants (heterozygous for the mutation) to obtain plants homozygous for the mutation, this step is not required for the mutation in the TDM gene which is dominant. The primary mutants carrying the dominant mutation in the TDM gene are capable of production 2n gametes.

The invention thus provides a method for obtaining a plant producing Second Division Restitution (SDR) 2n gametes, wherein said method comprises providing a plant comprising a dominant mutation within a gene, herein designated as TDM gene, coding for a protein designated herein as TDM protein, wherein said protein has at least 75% sequence identity with amino acid residues 1 to 286 of the TDM protein of SEQ ID NO: 1 when said plant is Brassica spp. or at least 30% sequence identity with said residues when said plant is different from Brassica spp, and the 60 first amino acids of said protein comprise a motif $X_1X_2X_3$, wherein $X_1$ is a Threonine (T), $X_2$ is a Proline (P), and $X_3$ is a Proline (P) or a Glutamine (Q), herein designated as TPP/Q motif, and wherein said dominant mutation results in the ability of the plant to produce SDR 2n gametes.

In the following description, the standard one letter amino acid code is used.

TDM gene and protein sequences are available in the public database, such as with no limitations the Plaza databank (http://bioinformatics.psb.ugent.be/plaza/) and the phytozome web portal http://www.phytozome.net/ (phytosome v9.1).

The protein sequence identities for the TDM proteins are calculated on residues 1 to 286 of SEQ ID NO: 1, after sequence alignment using T-Coffee (v6.85) with default parameters (http://toolkit.tuebingen.mpg.de/t_coffee); the percentage identity is obtained from this alignment using Bioedit 7.2.5 (Hall, T. A., 1999. BioEdit: a user-friendly biological sequence alignment editor and analysis program for Windows 95/98/NT. Nucl. Acids. Symp. Ser. 41:95-98).

Each species has one or two TDM genes, usually one (FIGS. 1 and 2 and Table I). The TDM protein consists of about 400 to about 850 amino acids, depending on the species (FIG. 1). The first half of the TDM proteins is conserved as shown in the alignment of TDM proteins from various angiosperm species presented in FIG. 1. In particular, the 60 first amino acids of all TDM proteins comprise a conserved TPP/Q motif (FIG. 1).

The percentage sequence identity of the TDM proteins from various angiosperm species with residues 1 to 286 of the TDM protein of SEQ ID NO: 1 were calculated after multiple sequence alignment using T-Coffee (v6.85) with default parameters (http://toolkit.tuebingen.mpg.de/t_coffee). The identity matrix was obtained from this alignment using Bioedit 7.2.5 (Hall, T. A., 1999. BioEdit: a user-friendly biological sequence alignment editor and analysis program for Windows 95/98/NT. Nucl. Acids. Symp. Ser. 41:95-98). The results are presented in Table I, below.

TABLE I

TDM proteins sequence identity

| Plant | Sequence* Reference | SEQ ID NO: | Percent identity |
|---|---|---|---|
| Arabidopsis thaliana (At) | AT4G20900 | 1 | 100 |
| Arabidopsis lyrata (Al) | AL7G21800 | 2 | 93.5 |
| Brassica rapa (Bra) | Bra038794 | 3 | 81.5 |
| Carica papaya (Cp) | CP00166G00370 | 4 | 60.6 |
| Theobroma cacao (TC) | TC_Thecc1EG026936t1 | 5 | 59.3 |
| Manihot esculenta (ME) | ME07478G00970 | 6 | 61.3 |
| Fragaria vesca (FV) | FV3G14870 | 7 | 56.3 |
| Glycine max. (GM) | GM09g02945.1 | 8 | 54.5 |
| Glycine max. (GM) | GM15g13901 | 9 | 54.1 |
| Lotus japonicus (LJ) | LJ6G012540 | 10 | 53.6 |
| Medicago truncatula (MT) | MT2G030510 | 11 | 53.1 |
| Vitis vinifera (VV) | VV10G05780 | 12 | 53.1 |
| Cucumis sativus (Csa) | Csa166970 | 13 | 56.1 |
| Cucumis sativus (Csa) | Csa166990 | 14 | 55.7 |
| Eucalyptus grandis (Eucgr) | Eucgr.K01947 | 15 | 57 |
| Eucalyptus grandis (Eucgr) | Eucgr.L00875 | 16 | 57 |
| Aquilegia caerula (Aq) | Aq_Aquca_125_00007.1 | 17 | 52.2 |
| Phaseolus vulgaris (VV) | Pv_Phvul.006G127000.1 | 18 | 55.6 |
| Prunus persica (Pp) | Pp_ppa021291m | 19 | 55.6 |
| Gossypium raimondii | Gorai.009G115700.1 | 20 | 58.1 |
| Solanum lycopersicum (Sly) | Sly06g075640 | 21 | 57.2 |
| Solanum tuberosum (St) | St_PGSC0003DMP400052745 | 22 | 56.5 |
| Setaria italica (Si) | Si013284m | 23 | 39.6 |
| Brachypodium distachyon (BD) | BD3G14297 | 24 | 36.6 |
| Oryza sativa japonica (OS) | OS08G03620 | 25 | 37.8 |
| Oryza sativa indica(OSINDICA) | OSINDICA_08G02690 | 26 | 37.8 |
| Sorghum bicolor (SB) | SB07G002510 | 27 | 38 |
| Zea mays (ZM) | ZM06G01810 | 28 | 38.1 |

*All the sequences are from the Plaza databank (http://bioinformatics.psb.ugent.be/plaza/) except: Cucumus sativus, Solanum lycopersicum, Aquilegia caerulea, Phaseolus vulgaris, Prunus persica, Gossypium raimondii, Glycine max and Theobroma cacao that come from http://www.phytozome.net/ (phytosome v9.1).

A sequence having at least 30% sequence identity with amino acid residues 1 to 286 of the TDM protein of SEQ ID NO: 1 has at least 50% sequence similarity with amino acid residues 1 to 286 of the TDM protein of SEQ ID NO: 1. Therefore the TDM protein of plants other than Brassica spp. are alternatively defined as having at least 50% sequence similarity with amino acid residues 1 to 286 of the TDM protein of SEQ ID NO: 1 and comprising a TPP/Q motif in the 60 first amino acids of the protein.

The SDR 2n gametes produced according to the invention are useful in all the usual applications of 2n gametes, for instance for producing polyploid plants, or to allow crosses between plants of different ploidy level. They can also be useful in methods of genetic mapping, for instance the method of "Reverse progeny mapping" disclosed in WO 2006/094774.

According to a preferred embodiment of the method for obtaining a plant producing Second Division Restitution 2n gametes, said protein has at least 35%, and by order of increasing preference, at least 40, 45, 50, 55, 60, 65, 70, 75, 80, 85, 90, 95 or 98% sequence identity with the TDM protein of SEQ ID NO: 1, when said plant is different from *Brassica* spp. or at least 80% and by order of increasing preference, at least 85, 90, 95 or 98% sequence identity with the TDM protein of SEQ ID NO: 1, when said plant is *Brassica* spp. According to another preferred embodiment of the method for obtaining a plant producing Second Division Restitution 2n gametes, said TPP/Q motif is situated in a region of said protein which is that situated from positions 16-18 of SEQ ID NO: 1.

According to the invention, said dominant mutation is within an allele of a TDM gene or a TDM transgene, wherein the TDM gene or transgene is from any plant species, such as for example those mentioned in Table I. Therefore, the plant able to produce SDR 2n gametes is obtained by targeted or random mutagenesis of the TDM gene or by genetic transformation.

According to a preferred embodiment of the method of the invention for obtaining a plant able to produce SDR 2n gametes, said method comprises:
    providing a plant having said dominant mutation within an allele of a TDM gene, said plant being heterozygous or homozygous for this mutation.

Mutagenesis of the TDM gene can be targeted or at random. Random mutagenesis, for instance through EMS mutagenesis, is followed by screening of the mutants within the desired gene. Methods for high throughput mutagenesis and screening are available in the art. By way of example, one can mention TILLING (Targeting Induced Local Lesions IN Genomes, described by McCallum et al., Plant Physiology, 2000, 123, 439-442). Targeted mutagenesis is performed using standard techniques which are known in the art and use homologous recombination, preferably in combination with a nuclease such as for example a TALEN or CRISPR.

According to another preferred embodiment of the method of the invention for providing a plant able to produce SDR 2n gametes, said plant is a transgenic plant, and said method comprises:
    a) transforming at least one plant cell with a vector containing a DNA construct comprising a TDM gene having said dominant mutation;
    b) cultivating said transformed plant cell in order to regenerate a plant having in its genome a transgene containing said DNA construct.

The DNA construct comprises a TDM gene that can be either from the same species as the plant in which it is introduced or from a different one.

Among the mutations within the TDM gene, those resulting in the ability to produce SDR 2n gametes can be identified on the basis of the phenotypic characteristics of the plants which are heterozygous for this mutation: these plants can form at least 5%, preferably at least 10%, more preferably at least 20%, still more preferably at least 50%, and up to 100% of dyads as a product of meiosis.

Alternatively, dominant mutations within the TDM gene resulting in the ability of the mutant or transgenic plant to produce SDR 2n gametes can be identified by their ability to restore the fertility of *A. Thaliana* spo11/rec8 double mutants, wherein fertile spo11/rec8/tdm triple mutants are heterozygous for the TDM mutation, as demonstrated in the examples of the present application *A. Thaliana* spo11/rec8 double mutants are used for the screening of dominant mutations, which are then introduced into a plant of interest.

According to another preferred embodiment of the method of the invention for obtaining a plant producing Second Division Restitution 2n gametes, said dominant mutation comprises or consists of the mutation of at least one residue of the conserved TPP/Q motif.

The mutation may be a substitution, an insertion or a deletion, preferably a substitution or a deletion.

In a more preferred embodiment, said dominant mutation comprises or consists of the mutation of the T residue and/or its adjacent P residue. TP is a potential phosphorylation site. The examples of the present application demonstrate that the mutation of the T16 or P17 residue is able to dominantly confer premature meiotic exit. Without wishing to be bound by theory, the inventors believe that in view of these results, TDM is regulated by phosphorylation to ensure the meiosis I to meiosis II transition.

Therefore, the mutation is advantageously a mutation which abrogates phosphorylation of the T residue of said motif, i.e., a mutation which disrupts the TP phosphorylation site.

Said mutation is advantageously a substitution of said T and/or P residue(s) with a different residue, for example T is substituted with A and P is substituted with L. Alternatively, said mutation is a deletion of the T and P residues, and eventually additional residues flanking said T and/or P residues, such as for example the deletion of 1 to 10, preferably 1 to 5, even more preferably 1 or 2 residues.

Another aspect of the present invention relates to a DNA construct comprising a TDM gene having said dominant mutation resulting in the ability of the mutant/transgenic plant to produce SDR 2n gametes, as defined above. The TDM gene can be either from the same species as the plant in which it is introduced or from a different one. The DNA construct comprises the TDM gene in expressible form. Preferably, the TDM gene is placed under transcriptional control of a promoter functional in a plant cell. The promoter may be a TDM gene promoter such as the endogenous promoter of said TDM gene or another promoter which is functional in plant.

A large choice of promoters suitable for expression of heterologous genes in plants is available in the art.

They can be obtained for instance from plants, plant viruses, or bacteria such as *Agrobacterium*. They include constitutive promoters, i.e. promoters which are active in most tissues and cells and under most environmental conditions, as well as tissue-specific or cell-specific promoters which are active only or mainly in certain tissues or certain cell types, and inducible promoters that are activated by physical or chemical stimuli, such as those resulting from nematode infection. The promoter is chosen so as to be functional in meiocytes.

Non-limitative examples of constitutive promoters that are commonly used in plant cells are the cauliflower mosaic virus (CaMV) 35S promoter, the Nos promoter, the rubisco promoter, the Cassava vein Mosaic Virus (CsVMV) promoter.

Organ or tissue specific promoters that can be used in the present invention include in particular promoters able to confer meiosis-associated expression, such as the DMC1 promoter (KLIMYUK & JONES, Plant J, 1997, 11, 1-14).

The DNA constructs of the invention generally also include a transcriptional terminator (for instance the 35S transcriptional terminator, the nopaline synthase (Nos) transcriptional terminator or a TDM gene terminator).

The invention also includes recombinant vectors containing a DNA construct of the invention. Classically, said recombinant vectors also include one or more marker genes, which allow for selection of transformed hosts.

The selection of suitable vectors and the methods for inserting DNA constructs therein are well known to persons of ordinary skill in the art. The choice of the vector depends on the intended host and on the intended method of transformation of said host. A variety of methods for genetic transformation of plant cells or plants are available in the art for many plant species, dicotyledons or monocotyledons. By way of non-limitative examples, one can mention virus mediated transformation, transformation by microinjection, by electroporation, microprojectile mediated transformation, *Agrobacterium* mediated transformation, and the like.

The invention also provides a host cell comprising a recombinant DNA construct of the invention. Said host cell can be a prokaryotic cell, for instance an *Agrobacterium* cell, or a eukaryotic cell, for instance a plant cell genetically transformed by a DNA construct of the invention. The construct may be transiently expressed; it can also be incorporated in a stable extrachromosomal replicon, or integrated in the chromosome.

The inventors have further found that by combining the dominant mutation in the TDM mutation, with the inactivation of two genes, one which is essential for meiotic recombination initiation and is selected among SPO11-1, SPO11-2, PRD1, PRD2 (AT5G57880), PRD3/PAIR1 and DFO (AT1G07060) and the other one which is REC8, results in a MiMe mutant producing apomeiotic gametes.

The apomeiotic gametes produced by the MiMe mutant can be used, in the same way as the SDR 2n gametes, for producing polyploids plants, or for crossing plants of different ploidy level. They are also of interest for the production of apomictic plants, i.e. plants which are able to form seeds from the maternal tissues of the ovule, resulting in progeny that are genetic clones of the maternal parent.

A further object of the present invention is thus a method for obtaining a plant producing apomeiotic gametes, wherein said method comprises:

a) providing a plant comprising a dominant mutation in a TDM gene as defined above;

b) inhibiting in said plant a first protein involved in initiation of meiotic recombination in plants, said protein being selected among:

a protein designated as SPO11-1 protein, wherein said protein has at least 40%, and by order of increasing preference, at least 45, 50, 55, 60, 65, 70, 75, 80, 85, 90, 95 or 98% sequence identity, or at least 60%, and by order of increasing preference, at least, 65, 70, 75, 80, 85, 90, 95 or 98% sequence similarity with the SPO11-1 protein having the sequence accession number Q9M4A2 in the SwissProt database, corresponding to SEQ ID NO: 29 in the enclosed sequence listing;

a protein designated as SPO11-2 protein, wherein said protein has at least 40%, and by order of increasing preference, at least 45, 50, 55, 60, 65, 70, 75, 80, 85, 90, 95 or 98% sequence identity, or at least 60%, and by order of increasing preference, at least, 65, 70, 75, 80, 85, 90, 95 or 98% sequence similarity with the SPO11-2 protein having the sequence accession number Q9M4A2 in the SwissProt database, corresponding to SEQ ID NO: 30 in the enclosed sequence listing;

a protein designated as PRD1 protein, wherein said protein has at least 25%, and by order of increasing preference, at least 30, 35, 40, 45, 50, 55, 60, 65, 70, 75, 80, 85, 90, 95 or 98% sequence identity, or at least 35%, and by order of increasing preference, at least, 40, 45, 50, 55, 60, 65, 70, 75, 80, 85, 90, 95 or 98% sequence similarity with the PRD1 protein having the sequence accession number ABQ12642 in the GenBank database, corresponding to SEQ ID NO: 31 in the enclosed sequence listing;

a protein designated as PRD2 protein, wherein said protein has at least 25%, and by order of increasing preference, at least 30, 35, 40, 45, 50, 55, 60, 65, 70, 75, 80, 85, 90, 95 or 98% sequence identity, or at least 35%, and by order of increasing preference, at least, 40, 45, 50, 55, 60, 65, 70, 75, 80, 85, 90, 95 or 98% sequence similarity with the PRD2 protein having the sequence accession number AT5G57880 in the Plaza databank, corresponding to SEQ ID NO: 32 in the enclosed sequence listing;

a protein designated as PAIR1 protein, wherein said protein has at least 30%, and by order of increasing preference, at least 35, 40, 45, 50, 55, 60, 65, 70, 75, 80, 85, 90, 95 or 98% sequence identity, or at least 40%, and by order of increasing preference, at least, 45, 50, 55, 60, 65, 70, 75, 80, 85, 90, 95 or 98% sequence similarity with the PAIR1 protein having the sequence accession number NP_171675 in the GenBank database, corresponding to SEQ ID NO: 33 in the enclosed sequence listing;

a protein designated as DFO protein, wherein said protein has at least 30%, and by order of increasing preference, at least 35, 40, 45, 50, 55, 60, 65, 70, 75, 80, 85, 90, 95 or 98% sequence identity, or at least 40%, and by order of increasing preference, at least, 45, 50, 55, 60, 65, 70, 75, 80, 85, 90, 95 or 98% sequence similarity with the DFO protein having the sequence accession number AT1G07060 in the in the Plaza databank, corresponding to SEQ ID NO: 34 in the enclosed sequence listing; and c) inhibiting in said plant a second protein designated as REC8 protein, wherein said protein has at least 40%, and by order of increasing preference, at least 45, 50, 55, 60, 65, 70, 75, 80, 85, 90, 95 or 98% sequence identity, or at least 45%, and by order of increasing preference, at least, 50, 55, 60, 65, 70, 75, 80, 85, 90, 95 or 98% sequence similarity with the REC8 protein having the sequence accession number NP_196168 in the GenBank database, corresponding to SEQ ID NO: 35 in the enclosed sequence listing.

The protein sequence identity and similarity values provided herein for the SPO11-1, SPO11-2, PRD1, PRD2, DFO, PAIR1, or REC8 proteins are calculated using the BLASTP program under default parameters. Similarity calculations are performed using the scoring matrix BLOSUM62.

The inhibition of the above mentioned SPO11-1, SPO11-2, PRD1, PRD2, PAIR1, DFO or Rec8 proteins can be obtained either by abolishing, blocking, or decreasing their function, or advantageously, by preventing or down-regulating the expression of the corresponding genes. The SPO11-1, SPO11-2, PRD1, PRD2, DFO, PAIR1, and Rec8 proteins, and the inhibition of said proteins are disclosed in details in the Application WO 2010/00431.

By way of example, inhibition of said protein can be obtained by mutagenesis of the corresponding gene or of its promoter, and selection of the mutants having partially or totally lost the activity of said protein. Said inhibition is disclosed on page 5, beginning of last paragraph to page 6, end of 4$^{th}$ paragraph and page 6, last paragraph of WO 2010/00431 which are incorporated herein by reference.

Alternatively, the inhibition of the target protein is obtained by silencing of the corresponding gene. Such an inhibition is disclosed on page 7, beginning of 4$^{th}$ paragraph to page 9, end of paragraph before last and page 10, first three paragraphs of WO 2010/00431 which are incorporated herein by reference.

According to a preferred embodiment of the method of the invention for obtaining a plant able to produce apomeiotic gametes, said method comprises:

a) providing a plant having a dominant mutation within an allele of a TDM gene resulting in the ability to produce SDR 2n gametes, said plant being heterozygous for this mutation;

b) providing a plant having a mutation within an allele of a gene selected among the SPO11-1, SPO11-2, PRD1, PRD2, DFO, or PAIR1 gene resulting in the inhibition of the protein encoded by said allele, said plant being heterozygous for this mutation;

c) providing a plant having a mutation within an allele of the REC8 gene resulting in the inhibition of the protein encoded by said allele, said plant being heterozygous for this mutation;

e) crossing the plants of steps a) b) and c) in order to obtain a plant having a dominant mutation within an allele of a TDM gene, a mutation within an allele of a gene selected among the SPO11-1, SPO11-2, PRD1, PRD2, DFO or PAIR1 gene, and a mutation within an allele of the REC8 gene, said plant being heterozygous for each mutation;

f) self-fertilizing the plant of step e) in order to obtain a plant homozygous for the mutation within the TDM gene, for the mutation within the gene selected among the SPO11-1, SPO11-2, PRD1, PRD2, DFO or PAIR1 gene, and for the mutation within the REC8 gene.

According to another preferred embodiment of the method of the invention for obtaining a plant able to produce apomeiotic gametes, said plant is a transgenic plant, and said method comprises:

a) transforming at least one plant cell with a vector containing a DNA construct of the invention comprising a dominant mutation in a TDM gene as defined above, a vector containing a DNA construct targeting a gene selected among SPO11-1, SPO11-2, PRD1, PRD2, DFO and PAIR1, and a vector containing a DNA construct targeting the REC8 gene;

b) cultivating said transformed plant cell in order to regenerate a plant having in its genome transgenes containing said DNA constructs.

The expression of a DNA construct comprising a dominant mutation in a TDM gene, provides to said transgenic plant the ability to produce 2n SDR gametes. The co-expression of a DNA construct gene, comprising a dominant mutation in a TDM gene, a DNA construct targeting a gene selected among SPO11-1, SPO11-2, PRD1, PRD2, DFO and PAIR1, and a DNA construct targeting the REC8 gene, results in a down regulation of the proteins encoded by these three genes and provides to said transgenic plant the ability to produce apomeiotic gametes.

The invention also encompasses plants able to produce SDR 2n or apomeiotic gametes, obtainable by the methods of the invention.

This includes in particular plants comprising a dominant mutation within a TDM gene as defined above, as well as plants further comprising a first mutation within a gene selected among SPO11-1, SPO11-2, PRD1, PRD2, DFO or PAIR1 gene, wherein the SPO11-1, SPO11-2, PRD1, PRD2, DFO or PAIR1 protein encoded by said gene is inhibited as a result of this mutation; and a second mutation within the REC8 gene, wherein the REC8 protein is inhibited as a result of this mutation This also includes plants genetically transformed by at least one DNA construct of the invention. Preferably, said plants are transgenic plants, wherein said construct is contained in a transgene integrated in the plant genome, so that it is passed onto successive plant generations.

The invention also encompasses a method for producing SDR 2n gametes, wherein said method comprises cultivating a plant obtainable by a method of the invention and recovering the gametes produced by said plant. Preferably said gametes comprises at least 10%, more preferably at least 20%, and by order of increasing preference, at least 30%, 40%, 50%, 60%, 70%, 80%, or 90% of viable 2n gametes.

The invention also encompasses a method for producing apomeiotic gametes, wherein said method comprises cultivating a plant obtainable by a method of the invention and recovering the gametes produced by said plant. Preferably said gametes comprises at least 10%, more preferably at least 20%, and by order of increasing preference, at least 30%, 40%, 50%, or 60%, 70%, 80%, or 90% of viable apomeiotic gametes.

The present invention applies to a broad range of monocot- or dicotyledon plants of agronomical interest. By way of non-limitative examples, one can mention potato, rice, wheat, maize, tomato, cucumbers, alfalfa, sugar cane, sweet potato, manioc, clover, soybean, ray-grass, banana, melon, watermelon, cotton or ornamental plants such as roses, lilies, tulips, and *narcissus*.

The practice of the present invention will employ, unless otherwise indicated, conventional techniques which are within the skill of the art. Such techniques are explained fully in the literature.

In addition to the above arrangements, the invention also comprises other arrangements, which will emerge from the description which follows, which refers to exemplary embodiments of the subject of the present invention, with reference to the attached drawings in which:

FIG. 1 represents alignment of TDM proteins from various angiosperm species. Sequences were aligned with T-Coffee (v6.85) with default parameters. The sequence alignment was edited with BioEdit. Only the first half of the sequences which is conserved in TDM proteins is shown. The residues showing more than 80% identity in the TDM proteins which are aligned are in bold. The conserved region comprising the TPP/Q motif is boxed. Sequence identifiers for the amino acid sequences of the TDM proteins presented can be found in Table I and are as follows: AT4G20900_TDM, SEQ ID NO:1; AL7G21800, SEQ ID NO:2; Bra038794, SEQ ID NO:3; CP00166G00370, SEQ ID NO:4; TC_Thecc1EG02636t1, SEQ ID NO:5; ME07478G00970, SEQ ID NO:6; FV3G14870, SEQ ID NO:7; GM09g02945.1, SEQ ID NO:8; GM15g13901, SEQ ID NO:9; LJ6G012540, SEQ ID NO:10; MT2G030510, SEQ ID NO:11; VV10G05780, SEQ ID NO:12; Csa166970, SEQ ID NO:13; Csa166990, SEQ ID NO:14; Eucgr.K01947, SEQ ID NO:15; Eucgr.L00875, SEQ ID NO:16; Aq_Aquca_125_00007.1, SEQ ID NO:17; Pv_Phvu1.006G127000.1, SEQ ID NO:18; Pp_ppa021291m, SEQ ID NO:19; Gorai.009G115700.1, SEQ ID NO:20; Sly06g075640, SEQ ID NO:21; St_PGSC0003DMP400052745, SEQ ID NO:22; Si013284m, SEQ ID NO:23; BD3G14297, SEQ ID NO:24;

OS08G03620, SEQ ID NO:25; OSINDICA 08G02690, SEQ ID NO:26; SB07G002510, SEQ ID NO:27; ZM06G1810, SEQ ID NO:28.

FIG. 2 represents the phylogenetic tree of TDM proteins from various angiosperms, TDM_like1 proteins from Brassicales and TDM-like proteins from *Arabidopsis thaliana* and *Brachypodium distachyon*. The analysis was performed on the Phylogeny.fr platform and comprised the following steps. Sequences were aligned with T-Coffee (v6.85) using the following pair-wise alignment methods: the 10 best local alignments (Lalign_pair), an accurate global alignment (slow_pair). After alignment, positions with gap were removed from the alignment. The phylogenetic tree was reconstructed using the maximum likelihood method implemented in the PhyML program (v3.0 aLRT). Proteins of the TDM clade are shown for all species (including TDM-like1 in Brassicales). More distant TDM paralogues are shown only for *Arabidopsis thaliana* and *Brachypodium distachyon*.

At: *Arabidopsis thaliana*. Al: *Arabidopsis lyrata*. Bra: *Brassica rapa*. Sly: *Solanum lycopersicum*. St: *Solanum tuberosum*. Csa *Cucumis sativus*. Eucgr: *Eucalyptus grandis*. Cp: *Carica papaya*. ME: *Manihot esculenta*. TC: *Theobroma cacao*. Goraii *Gossypium raimondii*. FV: *Fragaria vesca*. Pp: *Prunus persica*. LI: *Lotus japonicus*. MT: *medicago truncatula*. GM: *Glycine max*. Pv *Phaseolus vulgaris*. VV: *Vitis vinifera*. Aq: *Aquilegia caerulea*. OS: *Oryza sativa japonica*. OSINDICA: *Oryza sativa indica*. BD: *Brachypodium distachyon*. SB: *Sorghum bicolor*. ZM: *Zea mays*. Si: *Setaria italica*.

Figure 3:
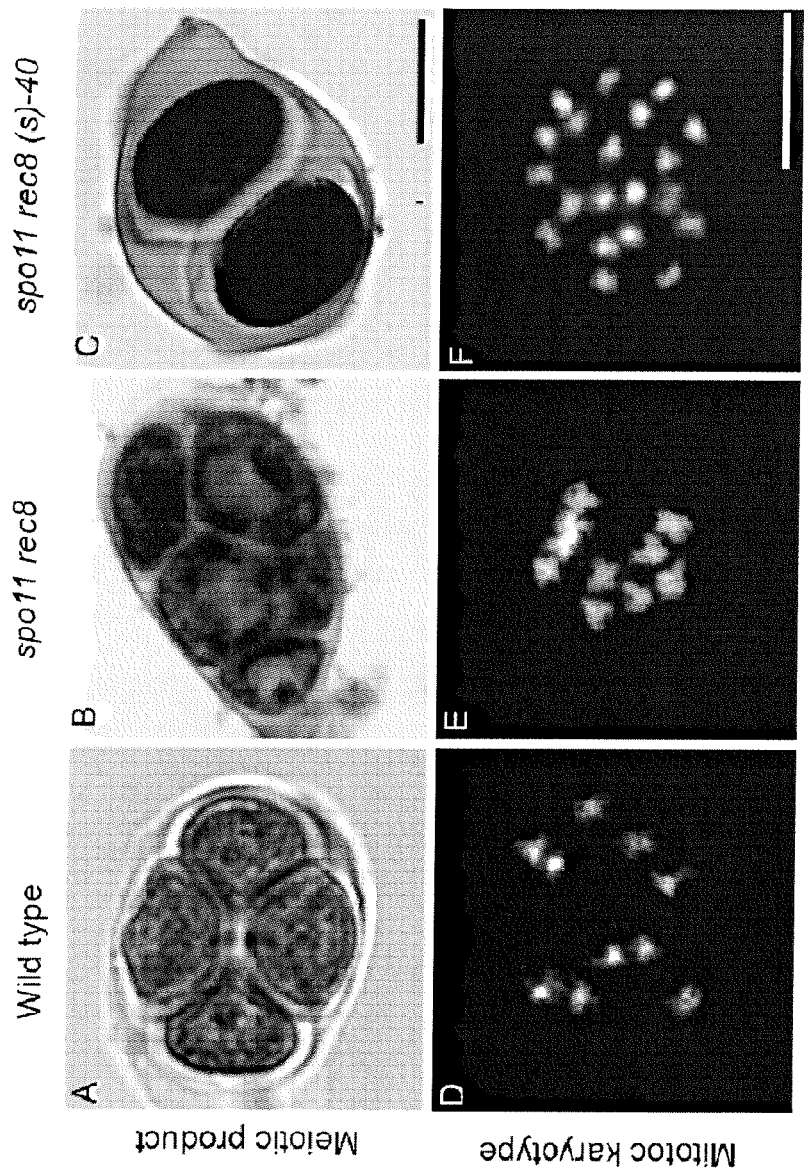

FIG. 3 shows that spo11-1 rec8 (s)-40 mutant produces dyads and is tetraploid. (A to C). Male meiotic products stained by toluidine blue. (A) Wild type produces tetrads of spores. (B) spo11-1 rec8 produces unbalanced polyads of spores. (C) spo11-1 rec8 (s)-40 produces dyads of spores. (D to F) Mitotic caryotype. (D) Wild type is diploid, having ten chromosomes aligned on mitotic metaphase plates. (E) spo11-1 rec8 is diploid. (F) spo11-1 rec8 (s)-40 is tetraploid, having 20 chromosomes aligned on mitotic metaphase plates. Scale bar=10 µM.

Figure 4:
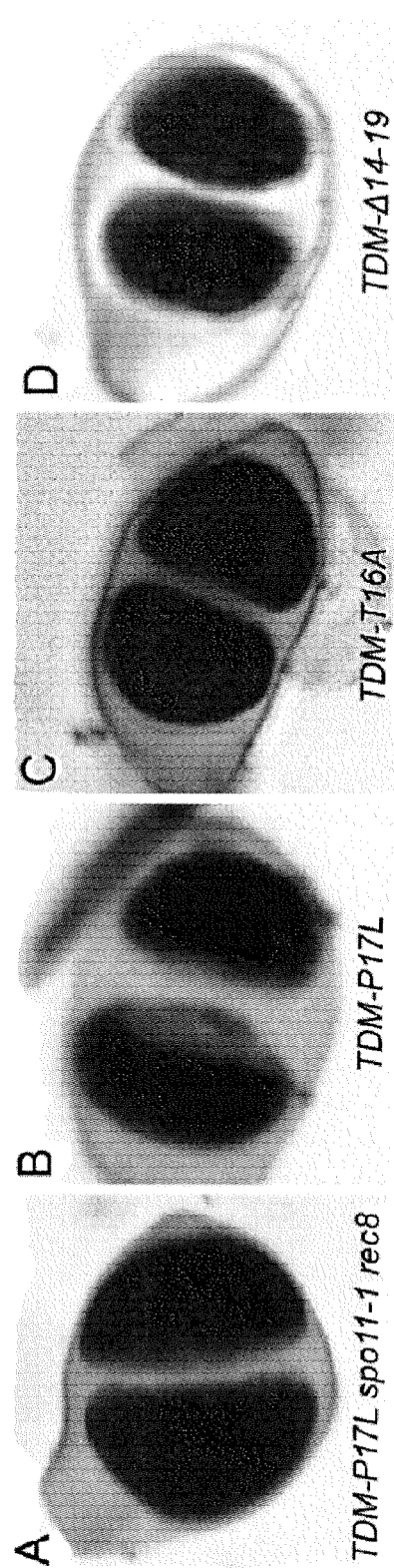

FIG. 4 illustrates meiotic products of TDM-P17L, TDM-T16A and TDM-Δ14-19. (A) spo11-1 rec8 mutants transformed with TDM-P17L. Wild type plants transformed by (B) TDM-P17L, (C) TDM-T16A or (D) TDM-Δ14-19. Dyads of spores are observed, compared to tetrads in wild type (FIG. 3A) and polyads in spo11-1 rec8 (FIG. 3B).

Figure 5:
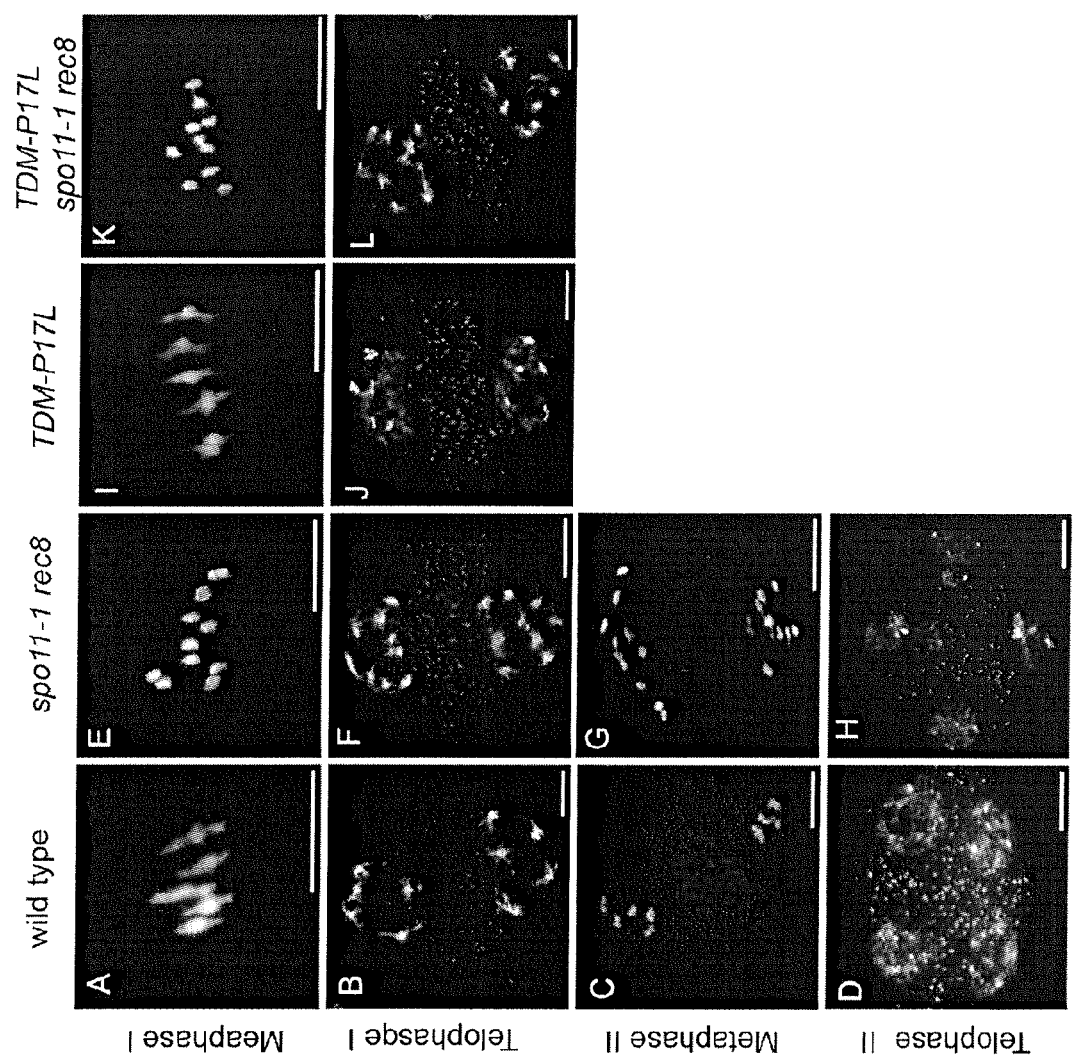

FIG. 5 illustrates meiotic chromosome spreads in wild type, spo11-1 rec8, TDM-P17 and spo11-1 rec8 TDM-P17 plants. (A to D) Meiosis in wild type. (A) Five bivalents align at metaphase I and (B) pairs of homologous chromosome are distributed into two nuclei at telophase I. (C) Five pairs of sister chromatids align on the two metaphase plates. (D) Four balanced nuclei are formed at telophase II. (E to H) Meiosis in spo11-1 rec8. The first division resembles a mitotic division with (E) alignment at 10 pairs of chromatids on the metaphase plates and (F) segregation into two groups of 10 chromatids. (G) single chromatids fail to align properly at metaphase II, resulting into (H) a variable number of unbalanced nuclei at telophase II. (I to J) Meiosis in wild type plant transformed with TDM-P17. A single, meiosis I-like division is observed. (K to L) Meiosis in spo11-1 rec8 plants transformed with TDM-P17. A single, mitotic-like division is observed.

EXAMPLES

Experimental Procedures

1. Growth Conditions and Genotyping

*Arabidopsis* plants were cultivated in greenhouse as previously described (Vignard et al., *PLoS Genet.*, 2007, 3, 1894-1906) or in vitro on *Arabidopsis* medium, as previously described (Estelle and Somerville, *Mol. Genet.*, 1987, 206, 200-206) at 21° C., under a 16-h to 18-h photoperiod and 70% relative humidity.

spo11-1-3 rec8-2 plants were genotyped as previously described (d'Erfurth et al., *PLoS Biol.*, 2009, 7, e1000124). tdm-3 plants were genotyped as described in Cromer et al., *PLoS Genet.*, 2012, 8, e1002865.

2. EMS Mutagenesis and Mutation Identification

EMS mutagenesis was performed as previously described (Crismani et al., Science, 2012, 336, 1588-1590). Whole genome sequencing was done by HiSeq™ 2000 (Illumina). A list of SNPs was generated compared to the reference genome of *Arabidopsis thaliana* TAIR10 (cultivar Columbia).

3. Cytology and Ploidy Analysis

Male meiotic products observation, chromosomes spreads, and ploidy measurement were carried out using the techniques described by d'Erfurth et al. (*PLoS Genet.*, 2008, 4, e1000274).

4. Directed Mutagenesis Constructs and Plant Tranformation

TDM genomic fragment was amplified by PCR using TDM U (5'-GACATCGGCACTTGCTTAGAG-3'; SEQ ID NO: 36) and TDM L (5'-GCGATATAGCTCCCACTGGTT-3'; SEQ ID NO: 37). The amplification covered 986 nucleotides before the ATG and 537 nucleotides after the stop codon. The PCR product was cloned, by Gateway™ technology (Invitrogen), into the pDONR207™ vector (Invitrogen), to create pENTR-TDM, on which directed mutagenesis was performed using the Stratagene QuickChange™ Site-Directed Mutagenesis Kit, according to the manufacturer's instructions. The mutagenic primers used to generate mutated version of TDM were SEQ ID NO: 38 to 41:

```
TDM-P17L:
5'-GAGTTTACTATACTCTGCCGCCGGCGAGAAC-3';

TDM-T16A:
5'-CTCCACCTGGAGTTTACTATGCCCCGCCGCCGGCGAGA-3';

TDM-Y14A:
5'-CCACCTGGAGTTGCGTATACTCCGCCGCGGCG-3';

TDM-Δ14-19:
5'-CCACCTGGAGTTGCGAGAACAAGTGATCATGTGGC-3';
``` and their respective reverse complementary primers. To generate binary vectors for plant transformation, an LR recombination reaction was performed with the binary vector for the Gateway™ system, pGWB1 (Nakagawa et al., Journal of Bioscience and Bioengineering. 2007, 104, 34-41). The resulting binary vectors, pTDM, pTDM-P17L, pT16A, and pTDM-Y14A, were transformed using the *Agrobacterium*-mediated floral dip method (Clough, S. J. and Bent A. F., Plant J., 1998, 16, 735-743) on wild type plants and plant populations segregating for the spo11-1 or rec8 or tdm-3 mutation. Transformed plants were selected on agar plates containing 20 mg/L hygromycin.

Example 1: A Dominant Mutation in TDM Leads to Premature Meiotic Exit

To identify new genes controlling meiotic progression, a genetic screen was designed based on the idea that mutations that lead to the skipping of the second meiotic division such as osd1 and cyca1;2/tam will restore the fertility of mutants that have unbalanced chromosome segregation defect only at the second meiotic division (d'Erfurth et al., *PLoS Biol.*, 2009, 7, e1000124; d'Erfurth et al., *PLoS Genet.*, 2010, 6, e1000989 and WO 2010/079432). This is the case of spo11rec8 double mutants, in which the first meiotic division resembles a mitosis (balanced segregation of sister chromatids to opposite poles) but the second division is unbalanced and leads to aneuploid gametes and hence very limited fertility (FIG. 5) (Chelysheva et al., *J. Cell. Sci.*, 2005, 118, 4621-32). Mutations in OSD1 (d'Erfurth et al., *PLoS Biol.*, 2009, 7, e1000124 2009) or CYCA1;2/TAM (d'Erfurth et al., *PLoS Genet.*, 2010, 6, e1000989), that lead to meiotic exit before meiosis II, are indeed able to restore fertility of spo11-1 rec8. Thus, a genetic screen was ran based on the restoration of fertility of spo11-1 rec8, aiming at identifying mutants conferring similar defects than osd1 or tam. Despite their meiotic segregation defect, spo11-1 rec8 plants produced enough residual seeds that were mutagenized with ethylmethane sulfonate (EMS). The M1 plants that are presumably heterozygous for EMS mutations were self-fertilized and harvested in bulks of ~5 to produce M2 families. About 2000 M2 families (400 bulks) were screened for increased fertility compared to spo11-1 rec8 non-mutagenized control.

Three bulks segregated plants with increased fertility. Genotyping confirmed that they were spo11-1 rec8 mutants which indicated that were genuine suppressors. Analysis of male meiotic products stained by toluidine blue showed that in all three cases, fertile plants produced dyads of spores, as observed in osd1 or cyca1;2/tam, instead of tetrads, as observed in wild type, suggesting that the second meiotic division did not occur in those plants (FIG. 3). Sequencing of candidate genes (CYCA1;2/TAM and OSD1) identified recessive mutations in CYCA1;2/TAM in two of the three families. The identified mutations were a splicing site in exon 7 (TAIR10 chr1:29082522 C>T) and a mutation in the 5'UTR region which introduced an upstream out of frame start codon (TAIR10 chr1:29084174 G>A). A complementation test showed that they were allelic, confirming that the mutations in CYCA1;2 caused the dyad phenotype and the restoration of fertility. The third family (spo11rec8(s)-40) had no mutation in OSD1 and CYCA1;2 and is the focus of this study.

Chromosome spreads unexpectedly showed that the four plants were tetraploids (FIG. 3). This suggested that the causal mutation was dominant and caused the production of diploid gametes in both male and female organs of the M1 plant. Whole genome sequencing of the bulk of two sister plants with ~100× coverage revealed the presence of 1144 SNPs compared to wild type. However, only 15 SNPs appeared as homozygote. These few homozygote SNPs were dispersed in the genome suggesting that they were present in the spo11-1 rec8 line before mutagenesis, rather than resulting from fixation of EMS induced mutations. The fact that almost all detected mutations were heterozygote further suggested that the causal mutation was dominant. This mutation would have been phenotypically expressed in the M1 plant leading, in combination with spo11-1 rec8 mutation, to the production of diploid clonal gamete as observed in a spo11-1 rec8 osd1 triple mutant (MiMe, d'Erfurth et al., *PLoS Biol.*, 2009, 7, e1000124 and WO 2010/079432), hence maintaining heterozygosity of EMS induced mutations from the M1 plant in the tetraploid M2 plants.

Candidate causal mutations were then looked for among the heterozygote SNPs. Among these 1129 mutations, 341 were predicted to affect a coding sequence (non-sense, missense or splicing site). Among them, a mutation in TDM resulting in an amino acid change (TDM-P17L), appeared as a good candidate as the potential causal dominant mutation. TDM was previously shown to be essential for meiotic exit at the end of meiosis II. Even if the meiotic defect observed in tdm knockout mutants (an extra round of division) differs drastically from the (spo11rec8(s)-40) defect, a dominant mutation in TDM appeared as a potential candidate to be the causal mutation in (spo11rec8(s)-40).

To test this hypothesis, a genomic clone containing the TDM gene (including promoter and terminator) that is able to complement tdm-3 mutant (n=8 transformants, 100% tetrads) was produced and mutated to recreate the mutation identified in the screen (TDM-P17L). When introduced in spo11-1rec8 plants, the TDM-P17L clone restored fertility of primary transformants (n=2/3. spo11-1 rec8: 0.1 seeds per fruit (n=197), spo11-1 rec8 TDM-P17L#15: 25 seeds per fruit (n=15), spo11-1 rec8 TDM-P17L#67: 48 seeds per fruit (n=10)) and led to the production of dyads (FIG. 4, table II). This demonstrates that the mutation in TDM is indeed the causal dominant mutation in spo11rec8(s)-40. Analysis of meiotic chromosome spreads in spo11-1rec8 TDM-P17L transformants showed a mitotic-like first division, with 10 univalents aligned at metaphase-I and sister chromatids segregated at anaphase I, and absence of second division (FIG. 5). Next, the ploidy level of spo11-1rec8 TDM-P17L offspring was explored. Among selfed progeny, only tetraploids (4n) were found (Table III). When spo11-1rec8 TDM-P17L pollen was used to fertilise a wild-type plant, all the resulting progeny were triploid (Table III). When spo11-1 rec8 TDM-P17L ovules were fertilised with wild-type pollen grains, only triploid plants were found (Table III). This demonstrated that spo11-1 rec8 mutants transformed by TDM-P17L produce high levels of male and female (100%) mitosis-like derived spores, which result in functional diploid gametes.

When introduced in wild type plants and tdm-3 mutants, the TDM-P17L genomic clone modified the meiotic phenotype of both genotypes by the production of dyads (FIG. 4, Table II).

TABLE II

| | Meiotic product of primary transformants | | |
|---|---|---|---|
| Construct | Transformed genotype | Number of independent transformants | Male meiotic products |
| — | wild type | — | Tetrads |
| — | tdm-3 | — | lobed monads |
| — | osd1 or tam | — | Dyads |
| — | spo11-1 rec8 | — | Polyads |
| TDM | tdm-3 | 8 | 8 tetrads |
| TDM-P17L | spo11-1 rec8 | 3 | 2 dyads |
| | | | 1 lobed monads |
| | wild type | 20 | 14 dyads |
| | | | 2 dyads and tetrads |
| | | | 4 lobed monads |
| | tdm-3 | 2 | 2 dyads |
| TDM-T16A | wild type | 2 | 2 dyads |
| TDM-Δ14_19 | wild type | 6 | 3 dyads |
| | | | 1 dyads and tetrads |
| | | | 2 tetrads |
| | tdm-3 | 4 | 4 dyads |
| TDM-Y14A | wild type | 5 | 5 tetrads |
| | tdm-3 | 3 | 2 tetrads |
| | | | 1 lobed monads |

TDM-P17L plants that produced dyads showed a wild type first division and an absence of meiosis II (FIG. 5)

which caused the formation of 2n gametes, a phenotype reminiscent of the one from osd1 and cyca1;2/tam (d'Erfurth et al., *PLoS Biol.*, 2009, 7, e1000124 and WO 2010/079432; d'Erfurth et al., *PLoS Genet.*, 2010, 6, e1000989). Ploidy levels were measured among the offspring of TDM-P17L plants (Table III). Among selfed progeny, tetraploids and triploids were found. When TDM-P17L ovules were fertilised with wild-type pollen grains, diploid and triploid plants were isolated (Table III).

TABLE III

Ploidy of spo11-1 rec8 TDM-P17L and TDM-P17L offsprings

| | Trans-formant | Selfed | Crossed as male with wild type | Crossed as female with wild type |
|---|---|---|---|---|
| spo11-1 rec8 | #15 | 100% 4n (n = 25) | 100% 3n (n = 5) | 100% 3n (n = 24) |
| TDM-P17L | #67 | 100% 4n (n = 24) | 100% 3n (n = 10) | 100% 3n (n = 18) |
| TDM-P17L | #1 | 100% 4n (n = 4) | nd | 43% 3n, 57% 2n (n = 7) |
| | #2 | 60% 4n, 40% 3n (n = 30) | nd | 5% 3n, 95% 2n (n = 18) |
| | #3 | 73% 4n, 27% 3n (n = 11) | nd | nd |
| | #4 | nd | nd | 27% 3n, 73% 2n (n = 15) |
| | #8 | nd | nd | 22% 3n, 78% 2n (n = 18) |

In summary, the tdm-p17L dominant mutation confers a similar meiotic defect than the recessive osd1 or tam mutations, leading to the premature exit from meiosis before the second division and consequently to the production of diploid male and female gametes.

TDM belongs to a small family of protein conserved in plants. For instance, the *Arabidopsis* genome contains five other genes showing significant sequence similarity with TDM (FIG. 2). These TDM-like genes are of unknown function. The analysis of the protein sequences showed that the causal mutation was in a small domain conserved only in the TDM protein subfamily that contains typically one or two genes per plant species (FIG. 1). The Pro17 amino acid is absolutely conserved as well as the adjacent Thr16 amino acid (FIG. 1). This defines a minimum consensus phosphorylation site on the T16. To test this two other potential loss-of-phosphorylation versions of the genomic TDM gene were created at that site by substituting the phosphorylable amino acid by a non phosphorylable one (TDM-T16A), and by deleting the entire conserved domain (TDM-Δ14_19). Both TDM-T16A and TDM-Δ14_19 gave the dyad phenotype in a dominant manner when introduced into wild type plants, recapitulating the effect of TDM-P17L (Table II; FIG. 4). Further, when introduced into tdm-3 mutants, TDM-Δ14_19 also showed the dyad phenotype (Table II). However mutation of the TDM tyrosine 14 (TDM-Y14A), a slightly less conserved amino acid of the domain, was unable to confer the dyad phenotype when introduced in wild type and was able to complement the tdm-3 mutation (Table II). In summary, expression of TDM-P17L, -T16A and -Δ14-19 mutations are equally able to dominantly confer premature meiosis exit. As TP is a potential phosphorylation sites, this results suggest that TDM may be regulated by phosphorylation to ensure the meiosis I to meiosis II transition.

The invention claimed is:

1. A method for obtaining a plant producing Second Division Restitution 2n gametes,
   wherein said method comprises mutating, with a dominant mutation, by random or targeted mutagenesis or by genetic transformation, a plant comprising a gene, herein designated as TDM gene, coding for a protein designated herein as TDM protein,
   wherein said TDM protein is selected from the protein of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, or SEQ ID NO:28,
   and wherein said dominant mutation is a mutation of at least one residue of a motif $X_1X_2X_3$ in the 60 first amino acids of said TDM protein, wherein X1 is a Threonine (T), X2 is a Proline (P), and X3 is a Proline (P), or a Glutamine (Q), designated as the TPP/Q motif, said mutation being selected from the group consisting of the substitution of T and/or its adjacent P residues with a different amino acid residue and the deletion of said T and/or P residues, alone or with one or two amino acid residues flanking said T and/or P residues.

2. The method according to claim 1, wherein said mutation abrogates phosphorylation at the T residue of said motif.

3. The method according to claim 1, which comprises: providing by random or targeted mutagenesis, a plant having said dominant mutation within an allele of a TDM gene, said plant being heterozygous for this mutation.

4. The method according to claim 1, wherein said plant is a transgenic plant, and said method comprises:
   a) transforming at least one plant cell with a vector containing a DNA construct comprising a TDM gene having said dominant mutation;
   b) cultivating said transformed plant cell in order to regenerate a plant having in its genome a transgene containing said DNA construct.

5. A method for producing Second Division Restitution 2n gametes, wherein said method comprises cultivating a plant obtained by the method of claim 1, and recovering the gametes produced by said plant.

6. The method according to claim 1, wherein said plant is selected from the group comprising: *Arabidopsis thaliana, Arabidopsis lyrata, Brassica rapa, Carica papaya, Theobroma cacao, Manihot esculenta, Fragaria vesca, Glycine* max, Lotus japonicus, Medicago truncatula, Vitis vinifera, Cucumis sativus, Eucalyptus grandis, Aquilegia caerula, Phaseolus vulgaris, Prunus persica, Gossypium raimondii, Solanum lycopersicum, Solanum tuberosum, Setaria italica, Brachypodium distachyon, Oryza sativa japonica, Oryza sativa indica, Sorghum bicolor, and Zea mays.

* * * * *

SEQUENCE LISTING

```
<160> NUMBER OF SEQ ID NOS: 41

<210> SEQ ID NO 1
<211> LENGTH: 434
<212> TYPE: PRT
<213> ORGANISM: Arabidopsis thaliana

<400> SEQUENCE: 1

Met Cys Pro Cys Val Glu Arg Arg Ala Pro Pro Gly Val Tyr Tyr Thr
1               5                   10                  15

Pro Pro Pro Ala Arg Thr Ser Asp Asp Val Ala Ala Met Pro Met Thr
            20                  25                  30

Glu Arg Arg Arg Pro Pro Tyr Ser Cys Ser Ser Ser Ser Glu Arg Arg
        35                  40                  45

Asp Pro Phe His Ile Val His Lys Val Pro Ser Gly Asp Ser Pro Tyr
    50                  55                  60

Val Arg Ala Lys His Ala Gln Leu Ile Asp Lys Asp Pro Asn Arg Ala
65                  70                  75                  80

Ile Ser Leu Phe Trp Thr Ala Ile Asn Ala Gly Asp Arg Val Asp Ser
                85                  90                  95

Ala Leu Lys Asp Met Ala Val Val Met Lys Gln Leu Gly Arg Ser Asp
            100                 105                 110

Glu Gly Ile Glu Ala Ile Lys Ser Phe Arg Tyr Leu Cys Ser Phe Glu
        115                 120                 125

Ser Gln Asp Ser Ile Asp Asn Leu Leu Leu Glu Leu Tyr Lys Lys Ser
    130                 135                 140

Gly Arg Ile Glu Glu Glu Ala Val Leu Leu Glu His Lys Leu Gln Thr
```

```
            145                 150                 155                 160
Leu Glu Gln Gly Met Gly Phe Gly Gly Arg Val Ser Arg Ala Lys Arg
                165                 170                 175

Val Gln Gly Lys His Val Ile Met Thr Ile Glu Gln Glu Lys Ala Arg
            180                 185                 190

Ile Leu Gly Asn Leu Gly Trp Val His Leu Gln Leu His Asn Tyr Gly
                195                 200                 205

Ile Ala Glu Gln His Tyr Arg Arg Ala Leu Gly Leu Glu Arg Asp Lys
    210                 215                 220

Asn Lys Leu Cys Asn Leu Ala Ile Cys Leu Met Arg Met Ser Arg Ile
225                 230                 235                 240

Pro Glu Ala Lys Ser Leu Leu Asp Asp Val Arg Asp Ser Pro Ala Glu
                245                 250                 255

Ser Glu Cys Gly Asp Glu Pro Phe Ala Lys Ser Tyr Asp Arg Ala Val
                260                 265                 270

Glu Met Leu Ala Glu Ile Glu Ser Lys Lys Pro Glu Ala Asp Leu Ser
            275                 280                 285

Glu Lys Phe Tyr Ala Gly Cys Ser Phe Val Asn Arg Met Lys Glu Asn
        290                 295                 300

Ile Ala Pro Gly Thr Ala Asn Lys Asn Tyr Ser Asp Val Ser Ser Ser
305                 310                 315                 320

Pro Ala Ser Val Arg Pro Asn Ser Ala Gly Leu Tyr Thr Gln Pro Arg
                325                 330                 335

Arg Cys Arg Leu Phe Glu Glu Thr Arg Gly Ala Ala Arg Lys Leu
                340                 345                 350

Leu Phe Gly Lys Pro Gln Pro Phe Gly Ser Glu Gln Met Lys Ile Leu
            355                 360                 365

Glu Arg Gly Glu Glu Pro Met Lys Arg Lys Leu Asp Gln Asn
        370                 375                 380

Met Ile Gln Tyr Leu His Glu Phe Val Lys Asp Thr Ala Asp Gly Pro
385                 390                 395                 400

Lys Ser Glu Ser Lys Lys Ser Trp Ala Asp Ile Ala Glu Glu Glu
                405                 410                 415

Ala Glu Glu Glu Glu Glu Arg Leu Gln Gly Glu Leu Lys Thr Ala
            420                 425                 430

Glu Met

<210> SEQ ID NO 2
<211> LENGTH: 426
<212> TYPE: PRT
<213> ORGANISM: Arabidopsis lyrata

<400> SEQUENCE: 2

Met Cys Pro Cys Glu Glu Arg Arg Ala Pro Pro Gly Val Tyr Tyr Thr
1               5                   10                  15

Pro Pro Pro Ala Arg Thr Ser Tyr Val Ala Ala Met Pro Leu Ser Glu
            20                  25                  30

Arg Arg Arg Pro Pro Phe Ser Cys Ser Ser Ser Glu Lys Arg Asp
        35                  40                  45

Pro Phe His Ile Val His Lys Val Pro Ser Gly Asp Ser Pro Tyr Val
    50                  55                  60

Arg Ala Lys His Ala Gln Leu Ile Asp Lys Asp Pro Asn Arg Ala Ile
65                  70                  75                  80

Ser Leu Phe Trp Thr Ala Ile Asn Ala Gly Asp Arg Val Asp Ser Ala
```

```
                85                  90                  95

Leu Lys Asp Met Val Val Met Lys Gln Leu Asp Arg Ser Asp Glu
            100                 105                 110

Gly Ile Glu Ala Ile Arg Ser Phe Arg Tyr Leu Cys Ser Phe Glu Ser
        115                 120                 125

Gln Asp Ser Ile Asp Asn Leu Leu Glu Leu Tyr Lys Lys Ser Gly
        130                 135                 140

Arg Ile Glu Glu Glu Ala Glu Leu Leu Glu His Lys Leu Lys Thr Leu
145                 150                 155                 160

Glu Gln Gly Met Gly Phe Gly Gly Arg Val Ile Arg Ala Lys Arg Val
                165                 170                 175

Gln Gly Lys His Val Thr Met Thr Ile Glu Gln Lys Ala Arg Val
            180                 185                 190

Leu Gly Asn Leu Gly Trp Val His Leu Gln Leu His Asn Tyr Gly Ile
        195                 200                 205

Ala Glu Gln His Tyr Arg Arg Ala Leu Gly Leu Glu Arg Asp Lys Asn
        210                 215                 220

Lys Gln Cys Asn Leu Ala Ile Cys Leu Met Arg Met Gly Arg Ile Pro
225                 230                 235                 240

Glu Ala Lys Ser Leu Leu Asp Asp Val Arg Asp Ser Pro Thr Glu Ser
                245                 250                 255

Glu Cys Gly Asp Glu Pro Phe Ala Lys Ser Tyr Asp Arg Ala Val Glu
            260                 265                 270

Met Leu Ala Glu Ile Glu Ser Lys Asn Pro Glu Ala Asp Leu Ser Asp
        275                 280                 285

Lys Phe Tyr Ala Gly Cys Ser Phe Ala Asn Gly Met Lys Glu Asn Ile
        290                 295                 300

Ala Pro Gly Ile Ala Asn Lys Asn Tyr Ser His Val Ser Ser Ser Pro
305                 310                 315                 320

Ala Ser Val Val Pro Asn Ser Ala Gly Leu Tyr Thr Gln Pro Arg Gly
                325                 330                 335

Cys Arg Ala Gly Met Tyr Glu Glu Thr Arg Gly Ala Ala Arg Lys
            340                 345                 350

Leu Leu Phe Glu Lys Pro Lys Pro Phe Ala Ser Glu Gln Ile Lys Ile
        355                 360                 365

Leu Lys Arg Gly Glu Glu Pro Gln Lys Arg Lys Leu Asp Pro
        370                 375                 380

Asn Met Ile Gln Tyr Leu His Glu Phe Ile Lys Asp Thr Ala Asp Gly
385                 390                 395                 400

Pro Lys Asn Glu Ser Lys Lys Ser Trp Ala Asp Ile Ala Glu Glu Glu
                405                 410                 415

Glu Glu Glu Glu Arg Leu Gln Ala Glu Thr
            420                 425

<210> SEQ ID NO 3
<211> LENGTH: 432
<212> TYPE: PRT
<213> ORGANISM: Brassica rapa

<400> SEQUENCE: 3

Met Cys Pro Phe Glu Asp Arg Arg Ala Pro Pro Gly Val Tyr Trp Thr
1               5                   10                  15

Pro Pro Pro Ala Arg Arg Thr Glu Asn Ala Ala Ala Met Pro Met Pro
            20                  25                  30
```

-continued

Leu Ser Glu Arg Arg Pro Pro Ser Ser Glu Lys Arg Asp Pro Phe
         35                  40                  45

His Ile Val His Lys Val Pro Ser Gly Asp Ser Pro Tyr Val Arg Ala
 50                  55                  60

Lys His Ala Gln Leu Val Tyr Lys Asp Pro Asn Arg Ala Ile Ser Leu
 65                  70                  75                  80

Phe Trp Ala Ala Ile Asn Ala Gly Asp Arg Val Asp Ser Ala Leu Lys
                 85                  90                  95

Asp Met Ala Val Val Phe Lys Lys Leu Asp Arg Ser Asp Glu Gly Ile
            100                 105                 110

Glu Ala Ile Lys Ser Phe Arg Tyr Leu Cys Pro Phe Glu Ala Gln Asp
        115                 120                 125

Ser Ile Asp Asn Leu Leu Glu Leu Tyr Lys Lys Ser Gly Arg Ile
    130                 135                 140

Gln Glu Glu Ala Glu Leu Leu Glu His Lys Leu Lys Val Ile Glu Gln
145                 150                 155                 160

Gly Met Gly Phe Gly Gly Arg Ile Val Arg Ala Lys Arg Val Gln Gly
                165                 170                 175

Lys His Val Thr Met Thr Val Glu Gln Glu Lys Ala Arg Val Leu Gly
            180                 185                 190

Asn Leu Gly Trp Val His Leu Gln Leu His Asn Tyr Gly Ile Ala Glu
        195                 200                 205

Gln His Tyr Arg Arg Ala Leu Cys Leu Glu Pro Asp Lys Asn Lys Gln
    210                 215                 220

Cys Asn Leu Ala Ile Cys Leu Met Arg Met Gly Arg Ile Pro Glu Ala
225                 230                 235                 240

Lys Ser Met Ile Asp Ala Val Arg Asp Ser Ser Ala Glu Thr Glu Ser
                245                 250                 255

Gly Asp Glu Pro Phe Thr Lys Ser Tyr Asn Arg Ala Val Glu Met Leu
            260                 265                 270

Ala Glu Val Glu Ser Lys Asp Pro Glu Asp Gly Leu Ser Asp Lys Phe
        275                 280                 285

Tyr Ala Gly Cys Ser Phe Ala Asn Gly Thr Met Lys Glu Asn Lys Ala
    290                 295                 300

Pro Arg Asn Ala Asn Arg Asn His Ser His Val Pro Pro Ser Pro Ala
305                 310                 315                 320

Ser Val Arg Gln Asn Ser Ala Gly Leu Phe Thr Gln Pro Arg Gly Cys
                325                 330                 335

Lys Gly Asp Pro Lys Asn Gly Val Ser Glu Glu Thr Gly Gly Ala
            340                 345                 350

Ala Arg Lys Leu Leu Phe Asp Lys Pro Ile Gly Ser Gln Arg Val Lys
        355                 360                 365

Leu Leu Lys Ser Gly Glu Gly Glu Gln His Val Lys Gly Lys Lys Leu
    370                 375                 380

Asp Gln Asn Met Ile Gln Asp Leu His Glu Tyr Ile Lys Asp Thr Ala
385                 390                 395                 400

Asp Cys Leu Lys Ser Gly Ser Lys Lys Ser Trp Ala Asp Met Ala Glu
                405                 410                 415

Glu Glu Asp Glu Glu Ser Val Gln Ser Gln Leu Lys Thr Ala Lys Ile
            420                 425                 430

<210> SEQ ID NO 4
<211> LENGTH: 670
<212> TYPE: PRT

<213> ORGANISM: Carica papaya

<400> SEQUENCE: 4

```
Met Trp Ala Asn Asp Arg Lys Pro Leu Gly Arg Gly Phe Ser Thr Pro
1               5                   10                  15

Gln Pro Thr Trp Asn Ser Arg Pro Arg Asp Ser Leu Val Met Pro Met
            20                  25                  30

Ser Glu Arg Lys Ser Ser Ser Pro Val His Lys Gly Asp Leu Phe His
        35                  40                  45

Val Val His Lys Val Pro Ala Gly Asp Ser Pro Tyr Val Arg Ala Lys
    50                  55                  60

His Val Gln Leu Ile Glu Lys Asp Pro Ser Arg Ala Ile Ser Leu Phe
65                  70                  75                  80

Trp Ala Ala Ile Asn Ala Gly Asp Arg Ile Asp Ser Ala Leu Lys Asp
                85                  90                  95

Met Ala Val Val Met Lys Gln Leu Asn Arg Ser Asp Glu Ala Ile Glu
            100                 105                 110

Ala Ile Lys Ser Phe Arg His Leu Cys Pro Tyr Asp Ala Gln Glu Ser
        115                 120                 125

Leu Asp Asn Val Leu Val Glu Leu Tyr Lys Arg Ser Gly Arg Ile Glu
    130                 135                 140

Glu Glu Val Glu Leu Leu Gln His Lys Leu Lys Asn Ile Glu Gly Val
145                 150                 155                 160

Thr Phe Gly Gly Lys Arg Thr Lys Thr Ala Arg Ser Gln Gly Lys Lys
                165                 170                 175

Ile Gln Ile Thr Val Glu Gln Glu Lys Ser Arg Ile Leu Gly Asn Leu
            180                 185                 190

Ala Trp Ala Tyr Leu Gln Gln His Asn Tyr Gly Ser Ala Glu Gln Tyr
        195                 200                 205

Tyr Arg Lys Ala Leu Ser Leu Glu Val Asp Lys Asn Lys Gln Cys Asn
    210                 215                 220

Leu Ala Ile Cys Leu Met His Met Asn Arg Ile Ala Glu Ala Lys Ser
225                 230                 235                 240

Leu Leu Leu Ala Val Arg Asp Ser Pro Lys Arg Gln Met Asp Glu
                245                 250                 255

Ser Cys Ala Lys Ser Phe Glu Arg Ala Tyr Gln Ile Leu Arg Glu Lys
            260                 265                 270

Glu Ser Gln His Glu Arg Ser Gly Arg Ser Glu Asp Ser Phe Tyr Val
        275                 280                 285

Val Asp Asn Glu Ser Ser Asn Ser Asp Lys Asn Gly Leu Asp Asn Trp
    290                 295                 300

Ser Asn Gly Cys Cys Ser Glu Ser Ser Leu Glu Met Ser Asn Phe Ala
305                 310                 315                 320

Asp Gly Met Lys Arg Tyr Gln Asn Gly Lys Glu Thr Glu Ala Ser Leu
                325                 330                 335

Gly Asn Asn Ser Tyr Ser Thr Cys Thr Arg Arg Lys Ser Gly Ile Phe
            340                 345                 350

Leu Thr Gln Pro Arg Arg Cys Ser Trp Gly Leu Glu Asp Glu Asn Tyr
        355                 360                 365

Arg Glu Ile Trp Gly Lys Ser Leu Gly Gly Ser Ser Val Arg Lys Leu
    370                 375                 380

Ser Phe Glu Gln Asn Lys Ile Thr Glu Asn Ala Phe Ser His Ala Ser
385                 390                 395                 400
```

Gly Asn Leu Lys Ser Gly Ile Leu Leu Thr Gln Pro Arg Arg Cys Ser
                    405                 410                 415

Trp Gly Leu Lys Asp Glu Lys Tyr Arg Glu Arg Leu Gly Lys Ser Leu
            420                 425                 430

Gly Gly Ser Ser Val Arg Lys Leu Ser Phe Glu Gln Ala Lys Ile Thr
        435                 440                 445

Glu Asn Ala Phe Ser His Ala Ser Gly Asn Leu Ile Glu Glu Pro Val
    450                 455                 460

Thr Cys Thr Asp Asp Asn Val Glu Ser His Ser Gly Val Leu Leu Thr
465                 470                 475                 480

Gln Pro Arg Val Ser Leu Gly Ile Asn Glu Asp Gln Arg Gly Lys Trp
                485                 490                 495

Gly Glu Asn Met Val Asp Ser Ser Pro Arg Gln Leu Ser Phe Glu Tyr
            500                 505                 510

Lys Asn Gln Lys Glu Asp Pro Val Asp Glu Asn Pro Glu Asn Leu Lys
        515                 520                 525

Asp Lys Ala Lys Ser Trp Ala Asp Ile Ala Glu Gly Asp Glu Glu
    530                 535                 540

Met Tyr Lys Glu Leu Val Cys Gly Asp Thr Pro Ser Lys Tyr Phe Asp
545                 550                 555                 560

Gly Leu Lys Ser Lys Glu Glu Glu Lys Phe Ser Asp Glu Asn Leu
                565                 570                 575

Asp Thr Asn Leu Met Tyr Gln Ser Pro Tyr Tyr Pro Leu Ser Gln Thr
            580                 585                 590

Glu Ala Ala Gly Gln Glu Leu Lys Ser Phe Tyr Gln Lys Asp Gly Tyr
        595                 600                 605

Asn Gly Thr Ser Gly Asn Ala Val Ser Ser Arg Asn Pro Thr Ala Arg
    610                 615                 620

Arg Ser Leu Tyr Phe Gly Gly Asp Ser Asn Ser Leu Pro Leu Lys Glu
625                 630                 635                 640

Lys Asp Ser Phe Thr Gly Lys Asn Ile Ser Met Thr Arg Arg Asn Arg
                645                 650                 655

Leu Lys Val Phe Thr Glu Ile Thr Leu Leu Pro Asp Ser Pro
            660                 665                 670

<210> SEQ ID NO 5
<211> LENGTH: 676
<212> TYPE: PRT
<213> ORGANISM: Theobroma cacao

<400> SEQUENCE: 5

Met Trp Ser Asn Glu Lys Asn Leu Pro Ser Arg Ser Arg Gly Phe Phe
1               5                   10                  15

Thr Pro Gln Pro Pro Ala Trp Lys Lys Ala Gln Ser Ser Val Leu Pro
            20                  25                  30

Met Ser Glu Arg Lys Arg Ile Ser Pro Ala Asp Gln Ala Asp Ser Phe
        35                  40                  45

His Val Ile His Lys Val Pro Ala Ser Asp Ser Pro Tyr Gly Arg Ala
    50                  55                  60

Lys His Val Gln Leu Ile Asp Lys Asp Pro Ser Lys Ala Ile Ser Leu
65                  70                  75                  80

Phe Trp Ala Ala Ile Asn Ala Gly Asp Arg Val Asp Ser Ala Leu Lys
                85                  90                  95

Asp Met Ala Val Val Met Lys Gln Leu Asn Arg Ser Asp Glu Ala Ile
            100                 105                 110

```
Glu Ala Ile Lys Ser Phe Arg His Leu Cys Pro His Asp Ser Gln Glu
            115                 120                 125

Ser Leu Asp Asn Val Leu Val Glu Leu Tyr Lys Arg Ser Gly Arg Val
    130                 135                 140

Glu Glu Glu Ile Glu Met Leu Gln Asn Lys Leu Arg Asn Ile Glu Gly
145                 150                 155                 160

Gly Thr Val Phe Gly Gly Lys Arg Thr Lys Ile Ala Arg Ser Gln Gly
                165                 170                 175

Lys Lys Ile Gln Ile Thr Ile Glu Gln Glu Lys Ser Arg Ile Leu Gly
            180                 185                 190

Asn Leu Ala Trp Ala Tyr Leu Gln Gln His Asn Tyr Gly Ile Ala Glu
        195                 200                 205

Gln His Tyr Arg Lys Ala Leu Ser Leu Glu Pro Asp Met Asn Lys Gln
    210                 215                 220

Cys Asn Leu Ala Ile Cys Leu Met His Met Asn Arg Ile Ser Glu Ala
225                 230                 235                 240

Lys Ser Leu Leu Gln Asp Val Lys Ala Ser Gly Asn Glu Gln Met
                245                 250                 255

Asp Glu Ser His Ser Lys Ser Tyr Glu Arg Ala Leu Asp Met Leu Ile
            260                 265                 270

Gln Val Glu Ser Gln Ser Met Leu Glu Pro Val Ala Lys Glu Pro Asp
    275                 280                 285

Lys Gly Arg Glu Ile Gln Arg Pro Ser Thr Pro Cys Arg Asp Arg Gly
290                 295                 300

Leu Lys Glu Ala Gly Ile Phe Leu Pro Arg Asn Glu Asp Asn Ile Ser
305                 310                 315                 320

Gly Phe Met Gly Arg Arg Leu Pro Tyr Ala His Trp Glu Gly Lys
                325                 330                 335

Met Leu Ile Asp Glu Gln Asn Gly Glu Ser Tyr Arg Arg Asn Pro Leu
            340                 345                 350

Glu Lys Asn Asp Asn Phe Pro Gly Tyr Asp Asp Arg Ser Ser Lys Cys
        355                 360                 365

Thr Pro Ile Gly Gln Lys Gly Tyr Leu Gln Ser Pro Gln Ser Met
    370                 375                 380

Phe Thr Glu Lys Trp Arg Ile Gly Ser Tyr Trp Glu Ser Pro Cys Glu
385                 390                 395                 400

Gly Tyr Ser Thr Gly Glu Glu Val Gly Ser Ala Gln Lys Lys Ile Tyr
                405                 410                 415

Ala Ser Ser Ala Ala Ser Lys Lys Asn Ser Glu Ala Leu Phe Thr Gln
            420                 425                 430

Pro Arg Arg Cys Ser Gln Gly Phe Asn Asn Ala Asp Gln Lys Arg Gly
        435                 440                 445

Gly Arg Trp Gly Glu Asp Thr Val Arg Asn Ser Ile Arg Lys Leu Ser
    450                 455                 460

Phe Glu Gln Ser Leu Thr Ser Glu Ser Glu Pro Leu His Ser Ile Gln
465                 470                 475                 480

Asn Leu Asn Glu Lys Pro Gln Ala Ser Asn Gly Lys Ser Glu Asn
                485                 490                 495

Ser Ala Thr Gly Pro Val Glu Glu Val Gln Glu Gly Leu Ser Gly
            500                 505                 510

Val Leu Phe Thr Gln Pro Arg Asn Ser Leu Leu Trp Leu Asn Asn Arg
        515                 520                 525
```

-continued

Asp Gln Arg Met Glu Arg Trp Ala Glu Glu Ser Val Gly Cys Pro Phe
    530                 535                 540

Arg Lys Leu Ser Phe Glu Lys Asn Ile Thr Gly Val Thr Pro His Ser
545                 550                 555                 560

Ala Asp Gly Leu Asn Gly Glu Pro Leu Phe Ser Ser Lys Asp Glu Ser
                565                 570                 575

Glu Ile Gly Leu Glu Arg Pro Ala Asn Ala Pro Asn Lys Lys Ser Trp
            580                 585                 590

Ala Asp Met Val Glu Glu Glu Lys Glu Glu Leu Leu Asn Ser Tyr
        595                 600                 605

Asp Gly Phe Asn Arg Glu Glu Val Phe Asn Asp Glu Asn Leu Asn Ser
    610                 615                 620

Asn Ile Ile Tyr Pro Arg Pro Asp Cys Lys Asp His Ile Gly Asn Ile
625                 630                 635                 640

Thr Gln Gln Leu Glu Ser Phe Asp Met Lys Gly Gly Asp Asn Ala Ser
                645                 650                 655

Ala Asn Thr Val Ser Ser Arg Arg Asn Arg Leu Pro Val Phe Arg Asp
            660                 665                 670

Ile Thr Ser Ser
        675

<210> SEQ ID NO 6
<211> LENGTH: 631
<212> TYPE: PRT
<213> ORGANISM: Manihot esculenta

<400> SEQUENCE: 6

Met Trp Ser His His Glu Asn Asn Ile Pro Ala Arg Gly Phe Ser Thr
1               5                   10                  15

Pro Pro Pro Ser Trp Lys Ser Pro His Cys Leu Ala Ala Met Pro Met
            20                  25                  30

Ser Glu Arg Lys Ser Val Ser Ser Gly Cys Lys Arg Asp Leu Phe His
        35                  40                  45

Val Ile His Lys Val Pro Ala Gly Asp Ser Pro Tyr Val Arg Ala Lys
    50                  55                  60

His Val Gln Leu Ile Glu Lys Asp Pro Ser Arg Ala Ile Ser Leu Phe
65                  70                  75                  80

Trp Ala Ala Ile Asn Ala Gly Asp Arg Ile Asp Ser Ala Leu Lys Asp
                85                  90                  95

Met Ala Val Val Met Lys Gln Leu Asn Arg Ser Asp Glu Ala Ile Glu
            100                 105                 110

Ala Ile Lys Ser Phe Arg Arg Leu Cys Pro Tyr Asp Ser Gln Glu Ser
        115                 120                 125

Ile Asp Asn Val Leu Val Glu Leu Tyr Lys Arg Ser Gly Arg Ile Glu
    130                 135                 140

Glu Glu Ile Glu Met Leu His Leu Lys Leu Asn Ile Glu Glu Gly
145                 150                 155                 160

Ile Ala Phe Gly Gly Lys Arg Thr Lys Thr Ala Arg Ser Gln Gly Lys
                165                 170                 175

Lys Ile Gln Ile Thr Val Glu Gln Glu Arg Ser Arg Ile Leu Gly Asn
            180                 185                 190

Leu Ala Trp Ala Tyr Leu Gln His His Asp Tyr Gly Leu Ala Glu Gln
        195                 200                 205

Tyr Tyr Arg Lys Ala Leu Ser Leu Glu Pro Asp Lys Asn Lys Gln Cys
    210                 215                 220

```
Asn Leu Ala Ile Cys Leu Met His Met Asn Arg Ile Pro Glu Ala Lys
225                 230                 235                 240

Ser Leu Leu Gln Ala Val Ser Asp Ser Cys Gly Ser Lys Gln Met Asp
            245                 250                 255

Asp Ser Tyr Ala Lys Ser Phe Glu Arg Ala Val Asp Ile Leu Thr Glu
            260                 265                 270

Leu Glu Ser Lys Ser Val Leu Lys Pro Ala Glu Asp Lys Glu Asn
        275                 280                 285

Gln Arg Ser Leu Ala Ser Pro Leu Leu Ser Asp Lys His Asp Arg Gly
        290                 295                 300

Ser Tyr Cys Gly Ile His Ser Glu Glu Gln Gly Asn Phe Ile Ser Ser
305                 310                 315                 320

Ser Gly Lys Gly Pro Gly Leu Ala Asn Lys Arg Met Leu Asp Ser Pro
                325                 330                 335

Ala Ala Val Leu Tyr Thr Gln Pro Lys Arg Val Met Gly Arg Ser Asp
            340                 345                 350

Glu Glu Glu Gln Arg Arg Gly Val Gly Trp Glu Asn Asp Thr Val Glu
        355                 360                 365

Lys Pro Ser Lys Asn Val Ser Ala Cys Ile Ile Arg Ser Leu Asp Gly
370                 375                 380

Glu Leu Leu Asp Pro Pro Ala Glu Arg Asn Trp Arg Glu Lys Ser Trp
385                 390                 395                 400

Thr Glu Val Ala Gln Gly Lys Ile Thr Gly Val Thr Val Pro Tyr Gln
                405                 410                 415

Phe Ser Gln Pro Arg Ile Arg Ala Phe Thr Gly Tyr Asn Asp Ala His
            420                 425                 430

Leu Lys Asp Glu Asn Val Thr Lys Ser Asp Ser Gln Gln Pro Ser Trp
        435                 440                 445

Arg Ser Asn Ala Arg Glu Thr Gly Gly Gln Met Gly Ser Thr Asn Glu
        450                 455                 460

Lys Ser Asp Ala Ser Ser Lys Phe His Leu Glu Gln Asn Met Val Val
465                 470                 475                 480

Asp Asp Ala Arg Gln Ser Glu Thr Ser Ile Asp Gly Lys Cys Gly Gln
                485                 490                 495

Thr Phe Gly Ile Asn Gly Cys Leu Gly Lys Asn Ser Ser Ser Lys Phe
            500                 505                 510

Ala Ile Lys Ser Trp Ala Asp Met Val Glu Glu Glu Glu Lys Leu
        515                 520                 525

Leu Thr Gly Lys Asp Leu Ser Pro Tyr Phe Asp Gly Gly Trp Asp Tyr
        530                 535                 540

Glu Glu Glu Ser Ala Asp Glu Asn Gln Asp Ser Asn Ile Ile His Gln
545                 550                 555                 560

Thr Ser Cys Pro Lys Ser Pro Ala Glu Ala Ile Asn Gln Lys Phe Glu
                565                 570                 575

Ala Phe Asp Leu Lys Asp Gly Phe Ala Phe Ser Asn Ala Val Ser
            580                 585                 590

Pro Arg Asn Pro Thr Val Arg Arg Ser Leu Arg Phe Asp Ala Lys Asn
        595                 600                 605

Asp Phe Ser Thr Arg Lys Lys His Arg Leu Gln Val Phe Gln Asp Ile
        610                 615                 620

Thr Pro Ser Ile Asp Ser Pro
625                 630
```

<210> SEQ ID NO 7
<211> LENGTH: 673
<212> TYPE: PRT
<213> ORGANISM: Fragaria vesca

<400> SEQUENCE: 7

```
Met Trp Ala Arg Asp Arg Ser Tyr Pro Pro Ala Gly Phe Phe Thr Pro
1               5                  10                  15

Pro Pro Pro Arg Lys Ser Gly Pro Pro Asn Pro Pro Met Ser Glu
            20                  25                  30

Arg Lys Arg Val Ser Pro Ala Ala Arg Ser Asp Leu Phe His Val
            35                  40                  45

Ala His Lys Val Pro Ala Gly Asp Ser Pro Tyr Val Arg Ala Lys Gln
    50                  55                  60

Val Gln Leu Ile Asp Lys Asn Pro Ser Lys Ala Ile Ser Leu Phe Trp
65                  70                  75                  80

Ala Ala Ile Asn Ala Gly Asp Arg Val Asp Ser Ala Leu Lys Asp Met
                85                  90                  95

Ala Val Val Met Lys Gln Leu Asp Arg Ala Glu Glu Ala Ile Glu Ala
            100                 105                 110

Ile Lys Ser Phe Arg His Leu Cys Pro Tyr Glu Ser Gln Glu Ser Leu
        115                 120                 125

Asn Asn Val Leu Val Glu Leu Tyr Lys Arg Ala Gly Arg Ile Glu Asp
    130                 135                 140

Glu Ile Glu Thr Leu Gln Ser Lys Leu Lys Arg Met Asp Gly Ile
145                 150                 155                 160

Ala Phe Asn Gly Lys Arg Thr Lys Thr Ala Arg Ala Gln Gly Lys Lys
                165                 170                 175

Val Gln Ile Thr Val Glu Gln Glu Arg Ser Arg Val Leu Gly Asn Leu
            180                 185                 190

Ala Trp Ala Tyr Met Gln Gln Gly Asn Tyr Thr Thr Ala Glu Glu His
        195                 200                 205

Tyr Lys Asn Ala Leu Ala Leu Glu Pro Asp Lys Asn Lys Gln Cys Asn
    210                 215                 220

Leu Ala Ile Cys Leu Met His Met Asn Arg Ile Thr Glu Ala Arg His
225                 230                 235                 240

Leu Leu Gln Ala Val Arg Asp Ser Ala Gly Asn Lys Pro Met Asp Glu
                245                 250                 255

Ser Tyr Ala Lys Ser Phe Glu Arg Ser Phe Glu Met Leu Thr Glu Leu
            260                 265                 270

Glu Gln Gln Ser Val Leu Arg Pro Ile Gln Gln Asn Glu Asn Tyr Cys
        275                 280                 285

Thr Gly Ile Ser Arg Thr Pro Lys Pro Ser Gly Ser Gly Tyr Met Pro
    290                 295                 300

Met Pro Pro Arg Arg Trp Thr Asp Gly Pro Glu Tyr Val Thr Val Ala
305                 310                 315                 320

Asn Glu Arg His Arg Glu Ser Phe Arg Pro Gly Ser Cys Ala Lys Ser
                325                 330                 335

Phe Asp Lys Trp Lys Lys Asp Tyr Asp Leu Lys Asn Thr Gly Asp Ser
            340                 345                 350

Arg Pro Ser Phe Ser Ser Val Lys Gln Asn Gln Asp Gly Met Thr
        355                 360                 365

Val Thr Glu Val Asn Pro His Glu Lys Thr Tyr Val Ser Pro Val Leu
    370                 375                 380
```

```
Tyr Thr Gln Pro Arg Arg Pro Ser Trp Gly Phe Asn Asp Gly His Gln
385                 390                 395                 400

Arg Ser Glu Ile Trp Gly Asn Gly Val Gly Ser Asn Lys Lys Leu
                405                 410                 415

Pro Pro Glu Arg Ser Ala Gly Asn Val Arg Ala His Val Val Arg Asn
            420                 425                 430

Leu Asn Ala Asp Leu Leu Ala Ser Thr Pro Arg Glu Ser Asp Ser Ser
        435                 440                 445

Leu Ser Ser Arg Ser His Gly Asp Trp Arg Met Pro Gln Arg Asp Ala
    450                 455                 460

Val Ala Arg Pro Val Leu Gln Pro Val Ser Ser Met Thr Ser Arg Gly
465                 470                 475                 480

Asn Glu Gly Tyr Leu Pro Val Arg Asn Glu Ala Met Ile Asp Arg Ser
                485                 490                 495

Ser Lys Tyr Thr Gly Asn Gly Asp Ile Arg Arg Val Thr Trp Asp Asn
            500                 505                 510

Ala Gly Met Gln Lys Ser Ala Ala Gly Ser Gln Val Asp Glu Asn
        515                 520                 525

Ala Lys Ala Leu Leu Leu Cys Ile Asp Glu Gly Asp Ser Gln Ser Ser
    530                 535                 540

Gly Thr Thr Val Leu Gly Ser Met Glu Asn Met Asn Ala Ser Val Glu
545                 550                 555                 560

Glu Asp Cys Leu Gly Asp Asn Ser Ser Gly Thr Leu Asp Asn Val His
                565                 570                 575

Gln Ser Pro Ala Glu Asn Glu Arg Pro Thr Leu His Gln Ser Pro Ala
            580                 585                 590

Glu Thr Glu Lys Pro Thr Pro Asp Phe Trp Lys Tyr Ser Gly Lys Lys
        595                 600                 605

Ser Trp Ala Asp Met Val Glu Glu Glu Glu Glu Leu Arg Ser Gly
    610                 615                 620

Thr Thr Gly Tyr Phe Asp Ser Trp Asn Thr Gly Asp Glu Phe Asp Asp
625                 630                 635                 640

Glu Asn Arg Asn Pro Asn Ile Met Thr Pro Gln Ser Pro Gln Phe Gln
                645                 650                 655

Thr Gln Met Lys Arg Arg Asn Arg Leu Gln Ser Phe Gln Asp Ile Thr
            660                 665                 670

Asn

<210> SEQ ID NO 8
<211> LENGTH: 601
<212> TYPE: PRT
<213> ORGANISM: Glycine max

<400> SEQUENCE: 8

Met Leu Phe Glu Arg Gly Ser Pro Ala Arg Cys Tyr Met Thr Pro Pro
1               5                   10                  15

Pro Gln Arg Thr Ser Pro Trp Lys Pro Pro His Ser Arg Ser Ser Ser
            20                  25                  30

Val Pro Phe Ser Glu Arg Lys Met Ser Pro Asn Ser Val Asn Lys Ser
        35                  40                  45

Asp Ile Phe His Ile Ile His Lys Val Pro Ala Gly Asp Ser Pro Tyr
    50                  55                  60

Val Lys Ala Lys Gln Val Gln Leu Val Asp Lys Asp Pro Gly Arg Ala
65                  70                  75                  80
```

```
Val Ser Leu Phe Trp Ala Ala Ile Asn Ala Gly Asp Arg Val Glu Ser
                85                  90                  95

Ala Leu Lys Asp Met Ala Leu Val Met Lys Gln Leu Asn Arg Ser Asp
            100                 105                 110

Glu Ala Ile Glu Ala Ile Arg Ser Phe Arg His Leu Cys Pro Ser Asp
        115                 120                 125

Ser Gln Asp Ser Leu Asp Asn Ile Leu Val Glu Leu Tyr Lys Arg Ser
    130                 135                 140

Gly Arg Val Asp Glu Glu Ile Ala Met Leu Cys His Lys Leu Lys Gln
145                 150                 155                 160

Ile Glu Asp Gly Leu Thr Phe Val Gly Arg Thr Thr Lys Gln Ala Arg
                165                 170                 175

Ser Gln Gly Lys Lys Ile Gln Ile Thr Ala Glu Gln Glu Ile Ser Arg
            180                 185                 190

Ile Leu Gly Asn Leu Ala Trp Ala Tyr Leu Gln Lys Gly Asp Tyr Lys
        195                 200                 205

Thr Ala Glu Glu His Tyr Arg Lys Ala Leu Ser Phe Glu Val Asp Arg
    210                 215                 220

Asn Lys Gln Cys Asn Leu Ala Ile Cys Leu Ile His Met Asn Lys Ile
225                 230                 235                 240

Lys Glu Ala Lys Phe Leu Leu Gln Ala Val Arg Thr Ala Thr Lys Asn
                245                 250                 255

Arg Lys Met Asp Asp Ser Phe Ala Lys Ser Phe Glu Arg Ala Ser Gln
            260                 265                 270

Met Leu Ile Glu Ile Glu Thr Ser Ser Gln Asn Ala Ala Phe Ser
        275                 280                 285

Met Thr Thr Gln Cys Pro Pro Gln Ser Phe Glu Asn Ser Ile Arg Met
    290                 295                 300

Ser Ser Asp Ser Val Gln Ser Arg Ser Glu Asn Arg Ser Glu Ile Ser
305                 310                 315                 320

Glu Gly Asp Ala Pro His Ala Arg Arg Arg Leu Tyr Gln Ser Pro Asp
                325                 330                 335

Pro Ser Arg Arg Asp Leu Ser Val Pro Cys Thr Lys Pro Lys Arg Cys
            340                 345                 350

Ser Trp Gly Phe Asn Asn Gly His Arg Arg Glu Ala Trp Gly Asp Ala
        355                 360                 365

Asn Ser Asp Tyr Lys Pro Thr Phe Gly Thr Pro Asn Asp Lys His
    370                 375                 380

Val Thr Arg Met Leu Asn Ser Arg Glu Asn Gly Phe Ser Ser Pro Ala
385                 390                 395                 400

Asn Gly Asn Gly Lys Ala Ala Thr Leu Glu Asp Pro Ala Ile Leu Lys
                405                 410                 415

His Glu Ala Thr Lys Val Thr Ser Ser Asp Ser Leu His Thr Leu Asn
            420                 425                 430

Thr Glu Ser Ala Thr Glu Phe Thr Glu Lys Glu Lys Ser Ala Ala Asp
        435                 440                 445

Asp Ser Ser Tyr Gly Ser Ile Leu Ser Glu Ser His Val Thr Val Val
    450                 455                 460

Asn Gly Val Asn Glu Phe Ala Ser Gly Lys Arg Lys Pro Glu Lys Lys
465                 470                 475                 480

Ser Trp Ala Asp Ile Val Glu Glu Glu Gln Asn Glu Glu Asn Asp Phe
                485                 490                 495
```

```
Phe Ser Gly Phe Thr Asn Phe Asp Asp Lys Asn Gly Ala Glu Val Phe
                500                 505                 510

Asn Asp Glu Asn Glu Asp Ser Asn Ile Ile Tyr Pro Ser Pro Trp Pro
            515                 520                 525

Gln Asn Gln Pro Asp Glu Trp Ser Ser Lys Lys Leu Glu Ser Leu Asp
        530                 535                 540

Lys Lys Asp Gly His Tyr Ala Ser Glu Ser Ala Ile Leu Ser Arg Asn
545                 550                 555                 560

Pro Thr Ala Arg Arg Ser Leu Cys Phe Asn Pro Glu Leu Ile Gly Glu
                565                 570                 575

Lys Arg Leu Thr Arg Arg Ser Arg Leu Gln Val Phe Gln Asp Ile Thr
            580                 585                 590

Leu Leu Pro Glu Thr Pro Arg Phe Ala
        595                 600

<210> SEQ ID NO 9
<211> LENGTH: 602
<212> TYPE: PRT
<213> ORGANISM: Glycine max

<400> SEQUENCE: 9

Met Gln Phe Glu Arg Gly Ser Met Ala Arg Cys Tyr Met Thr Pro Pro
1               5                   10                  15

Pro Gln Pro Pro Ser Ser Trp Lys Pro Pro His Ser Gln Ser Pro Ser
            20                  25                  30

Val Pro Phe Ser Glu Arg Lys Lys Ser Pro Asn Ser Ala Asn Lys Ile
        35                  40                  45

Asp Leu Phe His Ile Ile His Lys Val Pro Ala Gly Asp Ser Pro Tyr
    50                  55                  60

Val Lys Ala Lys Gln Val Gln Leu Val Asp Lys Asp Pro Gly Arg Ala
65                  70                  75                  80

Ile Ser Leu Phe Trp Ala Ala Ile Asn Ala Arg Asp Arg Val Glu Ser
                85                  90                  95

Ala Leu Lys Asp Met Ala Leu Val Met Lys Gln Leu Asn Arg Ser Asp
            100                 105                 110

Glu Ala Ile Glu Ala Ile Arg Ser Phe Arg His Leu Cys Pro Ser Asp
        115                 120                 125

Ser Arg Asp Ser Leu Asp Asn Ile Leu Val Glu Leu Tyr Lys Arg Ser
    130                 135                 140

Gly Arg Ile Asp Glu Glu Ile Ala Met Leu His His Lys Leu Lys Gln
145                 150                 155                 160

Ile Glu Asp Gly Leu Thr Phe Val Gly Arg Thr Thr Lys Gln Ala Arg
                165                 170                 175

Ser Gln Gly Lys Lys Ile Gln Ile Thr Ala Glu Gln Glu Ile Ser Arg
            180                 185                 190

Ile Leu Gly Asn Leu Ala Trp Ala Tyr Leu Gln Lys Gly Asp Tyr Lys
        195                 200                 205

Ala Ala Glu Glu His Tyr Arg Lys Ala Leu Ser Phe Glu Val Asp Arg
    210                 215                 220

Asn Lys Gln Cys Asn Leu Ala Ile Cys Leu Ile His Met Asn Lys Ile
225                 230                 235                 240

Lys Glu Ala Lys Phe Leu Leu Gln Ala Val Arg Thr Ala Thr Lys Asn
                245                 250                 255

Arg Lys Met Asp Asp Ser Phe Ala Lys Ser Phe Glu Arg Ala Ser Gln
            260                 265                 270
```

```
Met Leu Ile Glu Ile Glu Thr Ser Ser Ser Gln Asn Ala Ala Phe
        275                 280                 285

Ser Met Thr Thr Met Ser Gln Cys Ser Pro Gln Ser Phe Glu Asn Ser
    290                 295                 300

Ile Arg Lys Ser Ser Asp Arg Val Gln Ser Gly Ser Glu Ser Arg Ser
305                 310                 315                 320

Glu Thr Ser Glu Gly Asp Val Pro His Ala Arg Arg Arg Leu Tyr Gln
                325                 330                 335

Ser Pro Asp Pro Ser Arg Arg Asp Leu Ser Val Pro Cys Thr Lys Pro
                340                 345                 350

Lys Arg Cys Ser Trp Gly Phe Asn Thr Gly Tyr Arg Arg Glu Ala Trp
            355                 360                 365

Gly Asp Val Asn Ser Asp Tyr Lys Pro Ser Phe Gly Thr Pro Pro Asn
        370                 375                 380

Asp Lys His Ala Thr Arg Met Leu Asn Ser Arg Glu Asn Gly Leu Ser
385                 390                 395                 400

Ser Pro Ala Asn Gly Lys Trp Arg Ala Met Thr Leu Glu Asp Gln Ala
                405                 410                 415

Ile Leu Lys His Glu Ala Thr Thr Ala Thr Ser Ser Asp Ser Leu His
            420                 425                 430

Ala Leu Asn Thr Glu Val Ala Met Glu Phe Thr Glu Lys Lys Ser
        435                 440                 445

Ala Ala Asp Asp Ser Ser Tyr Arg Ser Ile Leu Ser Glu Ser His Val
    450                 455                 460

Thr Val Val Asn Gly Ala Asn Glu Phe Ala Ser Gly Lys Arg Lys Pro
465                 470                 475                 480

Glu Lys Lys Ser Trp Ala Asp Ile Val Glu Glu Gln Asn Glu Glu
                485                 490                 495

Tyr Asp Phe Leu Ser Gly Phe Thr Asn Phe Asp Asp Lys Asn Gly Ala
            500                 505                 510

Glu Val Phe Asn Asp Glu Asn Glu Asp Ser Asn Ile Ile Tyr Pro Ser
        515                 520                 525

Ser Trp Leu Gln Asn Leu Pro Glu Trp Ser Asn Lys Lys Leu Glu Ser
    530                 535                 540

Ser Asp Lys Lys Asp Asp Tyr Ala Ser Glu Ser Thr Ile Leu Ser Arg
545                 550                 555                 560

Asn Pro Thr Ala Arg Arg Ser Leu Cys Phe Asn Pro Glu Leu Ile Gly
                565                 570                 575

Glu Lys Lys Leu Thr Arg Arg Ser Arg Leu Gln Val Phe Gln Asp Ile
            580                 585                 590

Thr Leu Leu Pro Glu Thr Pro Arg Phe Ala
        595                 600

<210> SEQ ID NO 10
<211> LENGTH: 603
<212> TYPE: PRT
<213> ORGANISM: Lotus japonicus

<400> SEQUENCE: 10

Met Pro Phe Glu Arg Asn Ser Pro Ala Arg Cys Phe Met Thr Pro Pro
1               5                   10                  15

Pro Pro Arg Leu Ser Ser Trp Arg Ser Thr Pro Ser Arg Ser Pro Ile
            20                  25                  30

Met Met Pro Leu Ser Glu Arg Lys Arg Ser Ser Pro Asn Lys Asp Asp
```

```
            35                  40                  45
Pro Tyr His Val Ile His Lys Val Pro Ala Gly Asp Ser Pro Tyr Val
 50                  55                  60
Lys Ala Lys Gln Val Gln Leu Val Asp Lys Asp Pro Gly Lys Ala Ile
 65                  70                  75                  80
Ser Leu Phe Trp Ala Ala Ile Asn Ala Gly Asp Arg Val Glu Ser Ala
                 85                  90                  95
Leu Lys Asp Met Ala Leu Val Met Lys Gln Leu Asn Arg Ser Asp Glu
            100                 105                 110
Ala Ile Glu Ala Ile Lys Ser Phe Arg His Leu Cys Pro Pro Asp Ser
        115                 120                 125
Gln Glu Ser Leu Asp Asn Ile Leu Val Glu Leu Tyr Lys Arg Ser Gly
    130                 135                 140
Arg Val Asp Glu Glu Ile Ser Met Leu His His Lys Leu Lys Gln Ile
145                 150                 155                 160
Glu Asp Gly Val Thr Phe Val Gly Arg Thr Thr Lys Gln Ala Arg Ser
                165                 170                 175
Gln Gly Lys Lys Ile His Val Thr Ala Glu Gln Ile Ser Arg Ile
            180                 185                 190
Leu Gly Asn Leu Ala Trp Ala Tyr Leu Gln Lys Gly Asp Tyr Lys Ala
        195                 200                 205
Ala Glu Glu His Tyr Arg Lys Ala Leu Ser Phe Glu Val Asp Arg Asn
    210                 215                 220
Lys Gln Cys Asn Leu Ala Ile Cys Leu Met Gln Thr Asn Arg Ile Thr
225                 230                 235                 240
Glu Ala Lys Phe Leu Leu Gln Ala Val Thr Thr Ala Ser Lys His Arg
                245                 250                 255
Lys Met Asp Asp Ser Cys Ala Lys Ser Phe Glu Arg Ala Ser Gln Met
            260                 265                 270
Leu Met Asp Met Glu Ser Ser Ser Gln Cys Ser Pro Leu Ser Asn
        275                 280                 285
Leu Ser Gly Lys Ser Ser Asp Met Val Gln Ser Arg Thr Gln Asn Trp
    290                 295                 300
Ser Val Thr Ser Glu Gly Glu Val Ser Asn Ala Arg Arg Leu Tyr
305                 310                 315                 320
Glu Ser Pro Glu Pro Ala Arg Arg Asp Leu Lys Val Pro Tyr Thr Asn
                325                 330                 335
Thr Lys Lys Cys Ser Trp Gly Phe Asn Asn Gly Pro Gln Arg Glu Thr
            340                 345                 350
Trp Gly Asp Val His Ser Asp Pro Lys Pro Ser Phe Gly Ile Pro Ser
        355                 360                 365
Lys Gln Asn Asn Leu Ser Leu Pro Ala Asn Gly Lys Trp Asn Ala Arg
    370                 375                 380
Thr Met Val Lys Arg Glu Asp Lys Thr Ala Ile Gly Ser Gly Leu Tyr
385                 390                 395                 400
Thr Tyr Ser Asn Thr Glu Thr Asp Arg Lys Phe Lys Glu Asp Lys Phe
                405                 410                 415
Ala Val Glu Ser Asn Asp Met Val Val Asn Gly Ala Asn Gln Phe Ala
            420                 425                 430
Ser Ser Ile Gly Thr Asp Gln Ser Lys Cys Ser Glu Ile Ser Ile Lys
        435                 440                 445
Leu Cys Cys Tyr Pro Phe Cys Gln Leu Asn Ser Ser Leu Ile Asn Leu
    450                 455                 460
```

His Glu Leu Ala Ser Gly Ser Ile Lys Pro Val Lys Lys Ser Trp
465                 470                 475                 480

Ala Asp Ile Val Glu Glu Gln Asn Glu Gly His Asp Phe Phe Gly
                485                 490                 495

Gly Tyr Thr Arg Phe Asp Gly Gln Glu Gly Ala Gln Val Phe Asn Lys
            500                 505                 510

Glu Asn Glu Asn Ser Asn Ile Val Phe Gln Arg Pro Trp Pro Leu Ser
            515                 520                 525

Glu Thr Lys Cys Ile Ser Lys Lys Leu Glu Ser Met Asp Leu Lys Asp
        530                 535                 540

Gly His His Gly Ser Gly Thr Val Thr Leu Ser Arg Lys Pro Ala Val
545                 550                 555                 560

Arg Arg Ser Leu Cys Phe Asn Pro Glu Leu Ala Lys Glu Arg Asp Ser
                565                 570                 575

Ser Leu Ser Glu Glu Lys Lys Pro Pro Arg Asn Asn Arg Leu Gln Val
            580                 585                 590

Phe Lys Asp Ile Ala Leu His Pro Glu Thr Pro
            595                 600

<210> SEQ ID NO 11
<211> LENGTH: 617
<212> TYPE: PRT
<213> ORGANISM: Medicago truncatula

<400> SEQUENCE: 11

Met Thr Phe Glu Arg Asn Ser Pro Ala Arg Cys Tyr Met Thr Pro Pro
1               5                   10                  15

Ser Ser Ser Ser Ser Trp Lys Ser Arg Pro Val Arg Ser Pro Thr Val
            20                  25                  30

Pro Phe Ser Glu Arg Lys Lys Ser Pro Ala Ala Ser Val Ser Lys Asp
        35                  40                  45

Asp Leu Phe His Val Ile His Lys Val Pro Ser Gly Asp Ser Pro Tyr
    50                  55                  60

Val Lys Ala Lys Gln Val Gln Leu Val Asp Lys Asp Pro Gly Lys Ala
65                  70                  75                  80

Ile Ser Leu Phe Trp Ala Ala Ile Asn Ala Gly Asp Arg Val Glu Ser
                85                  90                  95

Ala Leu Lys Asp Met Ala Leu Val Met Lys Gln Leu Asn Arg Ser Asp
                100                 105                 110

Glu Ala Ile Glu Ala Ile Lys Ser Phe Arg His Leu Cys Pro Ser Asp
            115                 120                 125

Ser Gln Glu Ser Leu Asp Asn Ile Leu Val Glu Leu Tyr Lys Arg Ser
    130                 135                 140

Gly Arg Val Asp Glu Glu Ile Gly Met Leu His Gln Lys Leu Lys Gln
145                 150                 155                 160

Ile Glu Asp Gly Met Thr Tyr Val Gly Arg Thr Thr Lys His Ala Arg
                165                 170                 175

Ser Gln Gly Lys Lys Ile Gln Ile Ser Ala Glu Gln Ile Ser Arg
                180                 185                 190

Ile Leu Gly Asn Leu Ala Trp Ala Tyr Leu Gln Lys Gly Asp Tyr Lys
            195                 200                 205

Thr Ala Glu Glu His Tyr Arg Lys Ala Leu Ser Phe Glu Val Asp Arg
    210                 215                 220

Asn Lys Gln Cys Asn Leu Ala Ile Cys Leu Met Gln Met Asn Lys Val

|   |   |   |   |   |   |   |   |   |   |   |   |   |   |   |
|---|---|---|---|---|---|---|---|---|---|---|---|---|---|---|
| 225 | | | | 230 | | | | 235 | | | | 240 | | |

Thr Glu Ala Arg Phe Leu Leu Gln Ala Val Thr Ala Ala Thr Lys Asn
              245                   250             255

Arg Lys Met Asp Asp Ser Phe Val Lys Ser Tyr Glu Arg Ala Thr Gln
             260                 265                270

Met Leu Gln Glu Met Glu Ser Thr Ala Pro Ser Val Asp Ser Val Lys
        275                 280                 285

Asp Lys Gly Asp Asn Lys Phe Asn Glu Thr Glu Arg Phe Ser Gly Arg
290                   295                 300

Asn Met Ser Ser Pro Tyr Ser Thr Pro Asn Leu Glu Ser Ser Asn Gly
305                   310              315              320

Lys Thr Thr Gly Thr Val Lys Ser Arg Thr Glu Asn Asn Arg Ser Leu
             325                 330                335

Thr Ser Asp Ala Lys Asp Ser His His Ser His Ala Arg Arg Arg Leu
        340                 345                 350

Tyr Glu Ser Leu Asp Pro Ala Lys Ser Asp Pro Lys Val Pro Pro Tyr
           355                 360                365

Thr Lys Pro Lys Arg Pro Ser Trp Gly Phe Asn Ser His Ser Asp Ser
      370                 375                 380

Lys Pro Ser Phe Val Ser Tyr Pro Asn Glu Lys Ala Pro Tyr Ile Ile
385                   390              395              400

Lys Pro Asn Ser Thr Gln Asn Gly Phe Ser Pro Arg Thr Ala Thr Asn
             405                 410                415

Trp Arg Thr Arg Thr Pro Glu Gly Asp Ala Ala Ile Val Lys Tyr Gly
        420                 425                 430

Pro Thr Thr Thr Val Lys Gln Gly Asn Lys Thr Thr Val Phe Ser Ser
           435                 440              445

Gly Ser Ile Tyr Pro Leu Asn Thr Glu Ala Ala Met Lys Phe Thr Lys
      450               455                 460

Asn Asp Asn Asn Asn Lys Phe Thr Val Thr Asn Glu Phe Ala Ala Ser
465                   470              475              480

Val Asp Thr Lys Asp Gln Asn Gln Asp Lys Lys Leu Ala Lys Lys Ser
             485                 490                495

Trp Ala Asp Met Val Glu Glu Glu Gln Ser Glu Glu Tyr Glu Leu
        500                 505                510

Phe Tyr Lys Gly Tyr Thr Asn Phe Asp Ala Gln Val Phe Gln Asn Glu
             515                 520              525

Asn Glu Asn Ser Asn Ile Val Tyr Gln Pro Pro Ser Arg Arg Ser His
530                   535                 540

Tyr Glu Thr Glu Ser Leu Asn Gln Asn Leu Glu Phe Met Asn Leu Lys
545                   550              555              560

Asp Gly Tyr Asn Ala Ala Pro Val Asn Asp Thr Trp Leu Arg Asn Pro
             565                 570                575

Thr Val Arg Arg Ser Leu Phe Thr Asn Ala Glu Met Thr Asn Glu Arg
        580                 585                 590

Asp Val Phe Ser Gly Glu Glu Lys Arg Thr Arg Arg Ala Arg Leu Gln
           595                 600                605

Val Phe Gln Asp Ile Thr Ser Ser Ser
      610                 615

<210> SEQ ID NO 12
<211> LENGTH: 673
<212> TYPE: PRT
<213> ORGANISM: Vitis vinifera

<400> SEQUENCE: 12

```
Met Trp Ser His Asn Asn Asn Phe Pro Ala Lys Gly Phe Ser Thr Pro
1               5                   10                  15

Pro Pro Thr Trp Lys Ser Lys Ala Ser Phe Ser Ser Ala Thr Pro Val
            20                  25                  30

Ser Glu Lys Thr Arg Ser Met Ala Asn Lys Asp Asp Leu Phe His Val
        35                  40                  45

Val His Lys Val Pro Ala Gly Asp Ser Pro Tyr Val Arg Ala Lys Gln
    50                  55                  60

Val Gln Leu Ile Asp Lys Asp Pro Asn Arg Ala Ile Ser Leu Phe Trp
65                  70                  75                  80

Ala Ala Ile Asn Ser Gly Asp Arg Val Asp Ser Ala Leu Lys Asp Met
                85                  90                  95

Ala Val Val Met Lys Gln Leu Asn Arg Ser Asp Glu Ala Ile Glu Ala
            100                 105                 110

Ile Lys Ser Phe Arg His Leu Cys Pro Gln Glu Ser Gln Glu Ser Leu
        115                 120                 125

Asp Asn Val Leu Val Glu Leu Tyr Lys Arg Ser Gly Arg Leu Asp Glu
    130                 135                 140

Gln Ile Glu Met Leu Gln Tyr Lys Leu Lys Asn Ile Asp Glu Gly Ser
145                 150                 155                 160

Ala Phe Gly Gly Lys Arg Thr Lys Ile Ala Arg Ser Gln Gly Lys Lys
                165                 170                 175

Ile Gln Ile Ser Ile Glu Gln Glu Lys Ser Arg Leu Leu Gly Asn Leu
            180                 185                 190

Ala Trp Ala Tyr Leu Gln Gln Gly Asn Tyr Lys Thr Ala Gly Glu Leu
        195                 200                 205

Tyr Lys Gln Ala Leu Ala Leu Asp Pro Asp Arg Asn Lys Glu Cys Asn
    210                 215                 220

Leu Ala Ile Cys Leu Met Tyr Met Asn Lys Ile Lys Glu Ala Lys Ala
225                 230                 235                 240

Met Leu Tyr Ala Ile Gln Val Ser Ser Gln Asn Gly Arg Met Asp Asp
                245                 250                 255

Ser Tyr Val Lys Ser Phe Glu Arg Ala Ser Gln Val Leu Thr Glu Leu
            260                 265                 270

Glu Ala Asn Ser Val Ile Asp Pro Asn Glu Gln Glu Gly His Glu Glu
        275                 280                 285

Met Arg Arg His Leu Arg Ser Leu Val Ser Arg Asn Ser Ile Glu Val
    290                 295                 300

Asn Ser Cys Ile Asn Glu Glu Asn Asp His Leu Ser Gly Leu Val Ala
305                 310                 315                 320

Ser Arg Arg Arg Ala Gly Arg Gln Gln Glu Thr Met Leu Leu Asp
                325                 330                 335

Lys Pro Asn Arg Arg Ser Tyr Cys Gln Asn Phe Glu Asn Lys Asp
            340                 345                 350

Asn Phe Ser Gln Pro Asp Glu Glu Ser Ser Lys Cys Met Ser Leu Gly
        355                 360                 365

Leu Ser Ser Ala Gln Ser Pro Gln Asn Leu Tyr Ala Asp Lys Trp Lys
    370                 375                 380

Lys Gly Ala Gln Leu Glu Asn Pro Phe Glu Arg Ser Asp Phe Ser Ser
385                 390                 395                 400

Arg Arg Lys Gly Asn Trp Val Ser Ala Thr Asp Lys Val Gly Ser Val
```

```
            405                 410                 415
Gln Arg Arg Thr Tyr Gly Ser Pro Leu Pro Val Arg Gly Asn Ser Lys
            420                 425                 430

Leu Pro Ser Thr Glu Gln Arg Arg Gly Pro Cys Leu Leu Ser Lys Ala
            435                 440                 445

Asp Gln Arg Lys Ser Thr Trp Gly Glu Asn Thr Ala Asp Ser Pro Gly
            450                 455                 460

Arg Lys Leu Ser Phe Glu Asp Pro Ile Ala Lys Glu Ala Gly Ala Met
465                 470                 475                 480

Ala Pro Gln Asn Pro Asp Gly Arg Leu Gln Ala Ser Ser Asn Glu Lys
            485                 490                 495

Leu Lys Ile Ala Leu Gln Thr Ser Glu Lys Ser Leu Pro Ser Pro Gly
            500                 505                 510

Gly Phe Asp Gly Lys Cys Phe Arg Glu Asn Ser Gly Lys Leu Met Ser
            515                 520                 525

Leu Gln Gln Val Glu Gly Asn Pro Gln Leu Pro Asn Gln Asp Ser Ser
            530                 535                 540

Thr Ser Lys Asn Lys Met Ser Trp Ala Asp Met Leu Asp Tyr Cys Tyr
545                 550                 555                 560

Gln Lys Pro Ser Phe Ser Phe Gln Thr Pro Asn Lys Trp Tyr Asp Gly
            565                 570                 575

Trp Ser His Gly Glu Asp Phe Asn Asp Glu Asn Leu Asn Ser Asn Ile
            580                 585                 590

Phe His Gln Thr Pro Pro Ser Val His Glu Ile Asp Asn Val Ser Tyr
            595                 600                 605

Lys Leu Glu Ala Phe Asp Leu Lys Asp Gly Tyr Asn Thr Pro Gly Ser
            610                 615                 620

Asp Val Ser Ser Arg Asn Asn Pro Thr Ala Arg Arg Ser Leu Ser Asn
625                 630                 635                 640

Glu Thr Met Ser Thr Ser Gly Ser Thr Ile Arg Pro Lys Arg Arg Asn
            645                 650                 655

Arg Leu Gln Val Phe Arg Asp Ile Thr Leu His Thr Glu Ser Pro Arg
            660                 665                 670

Thr

<210> SEQ ID NO 13
<211> LENGTH: 773
<212> TYPE: PRT
<213> ORGANISM: Cucumis sativus

<400> SEQUENCE: 13

Met Leu Thr Asn Ser Gly Lys Asn Lys Phe Leu Cys Lys Gly Phe Ser
1               5                   10                  15

Thr Pro Pro Pro Ser Trp Lys Trp Lys Pro Phe Arg Leu Pro Lys Thr
            20                  25                  30

Ala Pro Phe Ser Glu Ser Lys Arg Leu Ser Pro Asn Phe Ala Asn Lys
            35                  40                  45

Ser Asp Leu Phe His Val Ile His Lys Val Pro Ala Gly Asp Ser Pro
            50                  55                  60

Tyr Val Lys Ala Lys Gln Val Gln Leu Ile Asp Lys Asp Pro Asn Arg
65                  70                  75                  80

Ala Val Ser Leu Phe Trp Ala Ala Ile Asn Ala Gly Asp Arg Val Asp
            85                  90                  95

Ser Ala Leu Lys Asp Met Ala Val Val Met Lys Gln Leu Asp Arg Ser
```

```
                 100                 105                 110
Asp Glu Ala Ile Glu Ala Ile Lys Ser Phe Arg His Leu Cys Pro Tyr
            115                 120                 125

Asp Ser Gln Glu Ser Ile Asp Asn Val Leu Ile Glu Leu Tyr Lys Arg
        130                 135                 140

Ser Gly Arg Ile Glu Glu Ile Asp Met Leu Gln Cys Lys Leu Lys
145                 150                 155                 160

Gln Ile Glu Asp Gly Thr Val Phe Gly Gly Lys Arg Thr Lys Ala Ala
                165                 170                 175

Arg Ser Gln Gly Lys Lys Val Gln Ile Thr Val Glu Gln Glu Lys Ser
            180                 185                 190

Arg Val Leu Gly Asn Leu Ala Trp Ala Phe Leu Gln Leu Asp Asn Ile
        195                 200                 205

Tyr Ile Ala Glu Glu Tyr Tyr Arg Lys Ala Leu Ser Leu Glu Ser Asp
    210                 215                 220

Asn Asn Lys Lys Cys Asn Leu Ala Ile Cys Leu Ile Leu Thr Asn Arg
225                 230                 235                 240

Leu Thr Glu Ala Lys Ser Leu Leu Gln Ser Val Arg Ala Ser Ser Gly
                245                 250                 255

Gly Lys Pro Met Glu Glu Ser Tyr Ala Lys Ser Phe Glu Arg Ala Ser
            260                 265                 270

His Met Leu Ala Glu Lys Glu Ser Lys Ser Phe Asn Ser Thr Glu His
        275                 280                 285

Glu Glu Asp Asn Asn Thr Ala Ala Thr Ile Thr Ser Lys Asn Thr Thr
    290                 295                 300

Gly Lys Ser Gly Arg Cys Val Pro Gln Ile Thr Ala Ser Thr Lys Trp
305                 310                 315                 320

Thr Arg Asp Asp Glu Arg Met Tyr Ile Asn Glu Asn Ser Trp Asp Asp
                325                 330                 335

Asp His His Trp Asp Cys Tyr Glu Asn Lys Ser Ile Gly Ala Val Asn
            340                 345                 350

Ser Ser His Asn Tyr Leu His Cys Asp Lys Trp Ser Glu Gly Cys Phe
        355                 360                 365

Ile Glu Asn Leu Gly Lys Thr Asp Ser Cys Ile Pro Ile Lys Ile Lys
    370                 375                 380

Gly Asp Arg Asn Gln Gly Gly Leu Phe Arg Leu Glu Asp Glu Ser Phe
385                 390                 395                 400

Asn Cys Cys Ser Leu Phe Ser Ser Pro Thr Pro Ala Lys Arg Ser Val
                405                 410                 415

Glu Val Pro Phe Thr Gln Pro Lys Asn Ser Phe Trp Glu Phe Asn Asn
        420                 425                 430

Arg Trp Gly Ser Lys Glu Arg Lys Gln Gln Arg Lys Arg Ile Arg Lys
    435                 440                 445

Val Leu Phe Gly Asn Pro Ser Lys Lys Asn Lys Ser Phe Asp Ser Gly
450                 455                 460

Phe Leu Val Asp Ser Ser Glu Ser Glu Gly Thr Lys Pro Thr Ser
465                 470                 475                 480

Asn Tyr Lys Thr Lys Tyr Arg Ser Ala Ala Pro Asp Ser Val Glu Leu
                485                 490                 495

Glu Val Pro Phe Thr Gln Pro Arg Ser Cys Glu Trp Val Met Asn Arg
        500                 505                 510

His Ser Arg Lys Ala Thr Glu Cys Phe Arg Ser Leu Arg Ser Ser Ser
    515                 520                 525
```

Ser Ser Arg Lys Leu Ser Phe Glu Pro Pro Thr Ser Thr Glu Asn Ile
    530                 535                 540

Gln Thr Thr Asn Asp Ser Asn Phe Gly Arg Phe Glu Leu Ser Arg Ala
545                 550                 555                 560

Val Ser Asp Glu Pro Gln Asp Leu Glu Gly Asp Trp Asn Gln Thr Ser
                565                 570                 575

Cys Gly Asp Ile Lys Tyr Glu Glu Gly Gly Ser Pro Met Leu Tyr Gly
            580                 585                 590

Leu Met Lys Lys Ile Lys Glu Glu Cys Ile Ala Val Asp Gln Lys Leu
        595                 600                 605

Gln His Asn Ser Pro Thr Val Phe Gly Lys Lys Ser Trp Ala Asp Met
610                 615                 620

Val Glu Glu Glu Glu Glu Lys Glu Met Ser Ser Ser Gly Ser
625                 630                 635                 640

Asp Gln Val Asn Cys Phe Ala Asp Asn Trp Ser Cys Ser Ser Asp Asp
                645                 650                 655

Asn Gly Glu Phe Lys Phe Asn Asp Glu Asn Leu Asn Ser Asn Ile Leu
            660                 665                 670

His Gln Asn His Cys Pro Pro Ser Ser Asn Gln Leu Glu Asp Thr Ile
        675                 680                 685

Lys Ile Gly Ser Leu Glu Ile Lys Asp Asp Ser Asp Glu Val Val Ser
690                 695                 700

Ser Arg Asn Ser Val Glu Arg Cys Pro Leu Tyr Phe Asp Gln Gln Gln
705                 710                 715                 720

Gln Pro Thr Leu Glu Ser Ile Asp Asn Cys Cys Ala Ser Pro Leu Pro
                725                 730                 735

Arg Lys Asp Leu Thr Thr Glu Val Ser Cys Lys Phe Gly Gln Glu Asn
            740                 745                 750

Lys Leu Met Arg Gly Asn Arg Leu Gln Val Phe His Glu Ile Thr Ser
        755                 760                 765

Val His Gln Glu Ser
    770

<210> SEQ ID NO 14
<211> LENGTH: 683
<212> TYPE: PRT
<213> ORGANISM: Cucumis sativus

<400> SEQUENCE: 14

Met Trp Thr Asn Asn Ser Lys Asn Asn Phe Pro Cys Lys Gly Phe Leu
1               5                   10                  15

Thr Pro Pro Ser Trp Lys Ser Gly Pro Phe Arg Ser Pro Lys Thr
            20                  25                  30

Ala Pro Phe Ser Glu Arg Lys Arg Ser Ser Pro Asn Phe Ala Asn Lys
        35                  40                  45

Ser Asp Leu Phe His Val Ile His Lys Val Pro Ala Gly Asp Ser Pro
    50                  55                  60

Tyr Val Lys Ala Lys Gln Val Gln Leu Ile Glu Lys Asp Pro Ser Arg
65                  70                  75                  80

Ala Val Ser Leu Phe Trp Ala Ala Ile Asn Ala Gly Asp Arg Val Asp
                85                  90                  95

Ser Ala Leu Lys Asp Met Ala Val Val Met Lys Gln Leu Asp Arg Ser
            100                 105                 110

Asp Glu Ala Ile Glu Ala Ile Lys Ser Phe Arg His Leu Cys Pro Tyr

```
                115                 120                 125
        Asp Ser Gln Glu Ser Ile Asp Asn Val Leu Ile Glu Leu Tyr Lys Arg
        130                 135                 140

Ser Gly Arg Ile Glu Glu Ile Asp Met Leu Gln Arg Lys Leu Lys
        145                 150                 155                 160

Gln Ile Glu Asp Gly Thr Ile Phe Gly Gly Lys Arg Thr Lys Ala Ala
                            165                 170                 175

Arg Ser Gln Gly Lys Lys Val Gln Ile Thr Ile Glu Gln Lys Ser
                        180                 185                 190

Arg Val Leu Gly Asn Leu Ala Trp Ala Phe Leu Gln Leu Asn Asn Ile
                        195                 200                 205

Tyr Val Ala Glu Asp Tyr Tyr Arg Lys Ala Leu Ser Leu Glu Ala Asp
                210                 215                 220

Asn Asn Lys Lys Cys Asn Leu Ala Ile Cys Gln Ile Leu Thr Asn Arg
        225                 230                 235                 240

Leu Thr Glu Ala Lys Ser Leu Leu Gln Ser Val Arg Ala Ser Ser Gly
                            245                 250                 255

Gly Lys Pro Met Glu Glu Ser Tyr Ala Lys Ser Phe Glu Arg Ala Phe
                        260                 265                 270

His Met Leu Thr Glu Lys Glu Ser Lys Ser Phe Asn Ser Thr Gly Asn
                        275                 280                 285

Glu Glu Asp Asn Gly Ala Gly Thr Thr Ile Thr Ser Lys Asn Ala Thr
                290                 295                 300

Gly Arg Thr Gly His Cys Val Pro Gln Ile Ala Ala Ser Thr Arg Trp
        305                 310                 315                 320

Thr Arg Asp Asp Glu Gln Met Tyr Ile Asn Glu Asn Ser Arg Asp Ile
                            325                 330                 335

Asp Pro His Trp Asp Cys Cys Asp Asp Lys Ser Val Gly Ala Val Asn
                        340                 345                 350

Ser Ser His Asn Tyr Leu His Ser Asp Lys Trp Ile Glu Gly Cys Cys
                        355                 360                 365

Ile Glu Asn Leu Gly Lys Thr Val Ser Cys Met Pro Ile Lys Met Lys
        370                 375                 380

Gly Asn Arg Asn Arg Asp Ser Leu Phe Arg Leu Val Glu Glu Ser Phe
        385                 390                 395                 400

Asn Cys Cys Ser Leu His Thr Ser Pro Thr Pro Thr Lys Lys Asn Val
                            405                 410                 415

Glu Val Pro Phe Thr Gln Gln Lys Asn Ser Phe Trp Glu Phe Asn Thr
                        420                 425                 430

Arg Trp Arg Ser Lys Glu Arg Lys Gln Gln Gln Lys Arg Thr Arg Lys
                        435                 440                 445

Val Leu Phe Glu Asn Pro Ser Arg Lys Asp Gln Ser Phe Asp Ser Gly
                450                 455                 460

Phe Val Val Asp Tyr Ser Ser Glu Ser Asp Glu Thr Glu Pro Ala Ser
        465                 470                 475                 480

Asn Tyr Lys Thr Lys Tyr Arg Ser Ala Ala Pro Asp Ser Ile Glu Leu
                            485                 490                 495

Glu Val Pro Phe Thr Gln Pro Arg Ser Cys Ser Trp Gly Met Asn Gly
                        500                 505                 510

Gly Gly Asn Ser Arg Lys Thr Thr Glu Cys Phe Arg Ser Leu Leu Ser
                        515                 520                 525

Arg Ser Ser Ser Arg Lys Leu Ser Phe Glu Leu Pro Thr Ser Thr Glu
                530                 535                 540
```

Asn Thr Gln Ala Met Thr Asp Ser Asn Leu Gly Arg Ser Lys Leu Ser
545                 550                 555                 560

Arg Glu Ile Ser Asp Glu Pro Gln Asp Leu Ala Gly Gly Asp Trp Lys
            565                 570                 575

Gln Thr Ser Tyr Gly Asp Ile Glu Tyr Glu Gly Thr Ile Pro Asn
        580                 585                 590

Asp Ser Met Lys Ile Met Glu Glu His Met Thr Ile Asp His Lys Phe
            595                 600                 605

Lys His Asn Thr Pro Thr Val Gly Gly Lys Lys Ser Trp Ala Asp Met
        610                 615                 620

Val Glu Glu Glu Glu Asp Ser Asp Asp Lys Asn Glu Asp Asp Thr
625                 630                 635                 640

Glu Glu Thr Leu Ser Ser Ser Gly Arg Gly Gln Val Asn Cys Phe Asp
            645                 650                 655

Asp Asn Trp Ser Ser Ser Ser Asp Asn Val Glu Tyr Lys Phe Asn Asp
            660                 665                 670

Glu Thr Leu Thr Val His Gln Glu Leu Glu Cys
        675                 680

<210> SEQ ID NO 15
<211> LENGTH: 644
<212> TYPE: PRT
<213> ORGANISM: Eucalyptus grandis

<400> SEQUENCE: 15

Met Trp Gly Asn Arg Glu Asn Phe Pro Ala Arg Gly Tyr Phe Thr Pro
1               5                   10                  15

Gln Pro Pro Lys Arg Ala Val Arg Pro Leu Val Ser Pro Val Leu Met
            20                  25                  30

Ser Glu Arg Lys Arg Ala Ser Pro Pro Asp Leu Phe His Ile Ile His
        35                  40                  45

Lys Val Pro Ala Gly Asp Ser Pro Tyr Val Lys Ala Lys Arg Val Gln
50                  55                  60

Leu Ile Asp Lys Asp Pro Ser Lys Ala Ile Ser Leu Phe Trp Ala Ala
65                  70                  75                  80

Ile Asn Ala Gly Asp Arg Val Asp Ser Ala Leu Lys Asp Met Ala Ile
                85                  90                  95

Val Met Lys Gln Leu Asn Arg Ser Asp Glu Ala Ile Glu Ala Ile Lys
            100                 105                 110

Ser Phe Arg His Leu Cys Pro Phe Asp Ser Gln Glu Ser Leu Asp Asn
        115                 120                 125

Val Leu Ile Glu Leu Tyr Lys Arg Ser Gly Arg Ile Glu Glu Glu Ile
    130                 135                 140

Glu Met Leu Gln His Lys Leu Arg Leu Ile Glu Glu Gly Lys Gly Phe
145                 150                 155                 160

Val Ala Asn Arg Thr Lys Thr Ala Arg Ser Gln Gly Lys Lys Ile Gln
                165                 170                 175

Val Thr Arg Glu Gln Glu Arg Ser Arg Ile Met Gly Asn Leu Ala Trp
            180                 185                 190

Ala His Leu Gln Leu Ser Asn Tyr Glu Ile Ala Glu Gly Leu Tyr Arg
        195                 200                 205

Glu Ala Leu Ser Leu Glu Pro Asp Lys Asn Lys Gln Cys Asn Leu Ala
    210                 215                 220

Ile Cys Leu Met Asn Met Asn Lys Leu Ala Asp Ala Lys Ala Val Leu

```
            225                 230                 235                 240
Asp Ala Val Arg Gly Pro Cys Gly Asp Gly Met Asp Glu Ser Tyr
                245                 250                 255
Ala Lys Ser Phe Asp Arg Ala Leu Gln Met Leu Asn Glu Ile Lys Ser
                260                 265                 270
Arg Pro Ile Lys Gln Asn Glu Val Asp His Lys Glu Ile Gln Asn Ser
                275                 280                 285
Arg Glu Ser Thr Cys Phe Thr Glu Gln Val Ile Asn Arg Gly Ala Arg
            290                 295                 300
Pro Leu Ala Ser Thr Thr Ala Asn Gly His Gly Glu Glu Thr Trp
305                 310                 315                 320
Ile Leu Asn Glu Arg Asn Gly Met Leu Ser Arg Ala Glu Ala Trp Ser
                325                 330                 335
Ser Ser Glu Asn Ile Phe Gly Asp Asn Trp Arg Glu Val Ser Asn Phe
                340                 345                 350
Gly Thr Pro Leu Arg Tyr Val Leu Pro Gly Asn Leu His Ala Lys Glu
                355                 360                 365
Asn Cys Leu Glu Thr Ser Lys Val Gly Trp Ser Ser Ser Lys Ser
            370                 375                 380
Ala Tyr Val Ser Pro Ala Ser Ile Lys Arg Asn Ile Glu Phe Ser Pro
385                 390                 395                 400
Gly Glu Ser Arg Arg His Thr Cys Arg Ser Leu Tyr Ala Ser Pro Ala
                405                 410                 415
Ser Cys Arg Asp Ser Glu Tyr Lys Ser Lys Ala Thr Ser Thr Gly Glu
                420                 425                 430
Thr Lys Leu Val Gly Asn Gly Ser Val Ala Met Ala Lys Pro Lys Asn
            435                 440                 445
Tyr Asp Glu Asn Met Ile Arg Ser Lys Gly Asp Pro Ala Lys Leu Val
            450                 455                 460
Glu Thr Ser Thr Asp Asp Ile Lys Asp Ser Gly Gly Glu Ser Phe Trp
465                 470                 475                 480
Val Asp Lys His Lys Lys Ser Trp Ala Asp Met Ala Glu Glu Glu
                485                 490                 495
Glu Gln Glu Pro Thr Asp Pro Pro Val Gln His Leu Trp Asn Asp Ser
                500                 505                 510
Pro Gln Lys Pro Pro Phe Arg Thr Pro Thr Arg Ser Phe Arg Ser
                515                 520                 525
Glu Glu Phe Asn Asp Glu Asn Leu Asp Ile Asn Ile Gly Gly His Glu
            530                 535                 540
Arg Thr Leu Thr Glu Asn Leu Ser Arg Thr Leu Thr Phe Ser Asp Leu
545                 550                 555                 560
Gly Cys Gly Ser Lys Ser Gln Thr Met Asp Thr Pro Ser Arg Thr Ser
                565                 570                 575
Gly Arg Ser Ala Val Arg Arg Ser Leu Asn Phe Asn Gln Ile Pro Lys
            580                 585                 590
Gln Glu Leu Asp Ser Val Met Leu Leu Glu Pro Glu Lys Ala Gly Gly
            595                 600                 605
Cys Gly Ala Pro Glu Asp Ala Val Pro Val Lys Lys Ala Gly Gln Pro
610                 615                 620
Pro Arg Arg Lys Arg Leu Gln Val Phe Gln Asp Ile Thr Arg Leu Pro
625                 630                 635                 640
Pro His Thr Ala
```

<210> SEQ ID NO 16
<211> LENGTH: 634
<212> TYPE: PRT
<213> ORGANISM: Eucalyptus grandis

<400> SEQUENCE: 16

```
Met Trp Gly Asn Arg Glu Asn Phe Pro Ala Arg Gly Tyr Phe Thr Pro
1               5                   10                  15

Gln Pro Pro Lys Arg Ala Thr Arg Pro Leu Val Ser Pro Val Leu Met
            20                  25                  30

Ser Glu Arg Lys Arg Ala Ser Pro Pro Asp Leu Phe His Ile Ile His
        35                  40                  45

Lys Val Pro Ala Gly Asp Ser Pro Tyr Val Lys Ala Lys Arg Val Gln
50                  55                  60

Leu Ile Asp Lys Asp Pro Ser Lys Ala Ile Ser Leu Phe Trp Ala Ala
65                  70                  75                  80

Ile Asn Ala Gly Asp Arg Val Asp Ser Ala Leu Lys Asp Met Ala Ile
                85                  90                  95

Val Met Lys Gln Leu Asn Arg Ser Asp Glu Ala Ile Glu Ala Ile Lys
            100                 105                 110

Ser Phe Arg His Leu Cys Pro Phe Asp Ser Gln Glu Ser Leu Asp Asn
        115                 120                 125

Val Leu Ile Glu Leu Tyr Lys Arg Ser Gly Arg Ile Glu Glu Glu Ile
130                 135                 140

Glu Met Leu Gln His Lys Leu Arg Leu Ile Glu Glu Gly Lys Gly Phe
145                 150                 155                 160

Val Ala Asn Arg Thr Lys Thr Ala Arg Ser Gln Gly Lys Lys Ile Gln
                165                 170                 175

Val Thr Arg Glu Gln Glu Arg Ser Arg Ile Met Gly Asn Leu Ala Trp
            180                 185                 190

Ala His Leu Gln Leu Ser Asn Tyr Glu Ile Ala Glu Gly Leu Tyr Arg
        195                 200                 205

Glu Ala Leu Ser Leu Glu Pro Asp Lys Asn Lys Gln Cys Asn Leu Ala
210                 215                 220

Ile Cys Leu Met Asn Met Asn Lys Leu Ala Asp Ala Lys Ala Val Leu
225                 230                 235                 240

Asp Ala Val Arg Gly Pro Cys Gly Asp Gly Asp Met Asp Glu Ser Tyr
                245                 250                 255

Ala Lys Ser Phe Asp Arg Ala Leu Gln Met Leu Asn Glu Ile Lys Ser
            260                 265                 270

Leu Pro Ile Lys Gln Asn Glu Val Asp His Lys Glu Ile Gln Asn Ser
        275                 280                 285

Arg Glu Ser Thr Cys Cys Thr Glu Arg Val Ile Asn Leu Gly Ala Gln
290                 295                 300

Pro Leu Ala Ser Thr Thr Ile Ala Asn Gly His Gly Glu Glu Thr Trp
305                 310                 315                 320

Ile Leu Asn Glu Arg Asn Gly Met Leu Ser Arg Ala Glu Ala Trp Ser
                325                 330                 335

Ser Ser Glu Asn Ile Phe Gly Asp Asn Trp Arg Glu Val Ser Asn Phe
            340                 345                 350

Gly Thr Pro Leu Arg Tyr Val Leu Pro Gly Asn Leu His Ala Lys Glu
        355                 360                 365

Asn Cys His Glu Thr Ser Lys Val Gly Trp Ser Ser Ser Arg Ser
370                 375                 380
```

```
Ala Tyr Ala Ser Pro Ala Ser Val Lys Arg Asn Ile Glu Phe Ser Pro
385                 390                 395                 400

Gly Glu Ser Arg Arg His Thr Cys Arg Ser Leu Ile Gln Val Glu Gly
            405                 410                 415

Tyr Phe Asn Trp Glu Arg Gln Asn Ser Ser Glu Met Gly Ser Val Ala
        420                 425                 430

Met Ala Lys Pro Lys Asn Tyr Asp Glu Asn Met Ile Arg Ser Lys Gly
    435                 440                 445

Asp Pro Ala Lys Val Val Glu Thr Ser Thr Asp Ile Lys Asp Ser
450                 455                 460

Gly Gly Glu Ser Phe Trp Val Asp Lys His Lys Lys Ser Trp Ala Asp
465                 470                 475                 480

Met Ala Glu Glu Glu Glu Gln Glu Pro Thr Asp Pro Val Gln
                485                 490                 495

His Leu Trp Asn Asp Ser Pro Gln Lys Pro Pro Phe Arg Thr Pro
            500                 505                 510

Thr Arg Ser Phe Arg Ser Glu Glu Phe Asn Asp Glu Asn Leu Asp Ile
            515                 520                 525

Asn Ile Gly Gly His Glu Arg Thr Leu Thr Glu Asn Leu Ser Arg Thr
530                 535                 540

Leu Thr Phe Ser Asp Leu Gly Cys Gly Ser Lys Ser Gln Thr Met Asp
545                 550                 555                 560

Thr Pro Ser Arg Thr Ser Gly Arg Ser Ala Val Arg Arg Ser Leu Asn
                565                 570                 575

Phe Asn Gln Ile Pro Lys Gln Glu Leu Asp Ser Val Met Leu Leu Glu
            580                 585                 590

Pro Glu Lys Ala Gly Gly Cys Gly Ala Pro Glu Asp Ala Val Pro Val
        595                 600                 605

Lys Lys Ala Gly Gln Pro Pro Arg Arg Lys Arg Leu Gln Val Phe Gln
610                 615                 620

Asp Ile Thr Arg Leu Pro Pro His Thr Thr
625                 630

<210> SEQ ID NO 17
<211> LENGTH: 689
<212> TYPE: PRT
<213> ORGANISM: Aquilegia caerula

<400> SEQUENCE: 17

Met Gly Ile Asp Asn Lys Lys Val Gly Met Lys Gly Phe Ser Thr Pro
1               5                   10                  15

Pro Pro Pro Pro Leu Arg Trp Lys Ser Ala Pro Cys Thr Pro Ile Gln
            20                  25                  30

Thr Leu Glu Met Asn Glu Glu Ser Leu His Gln Leu Ser Ala Thr Ile
        35                  40                  45

Ala Lys Val Asp Ser Phe His Ile Ile His Lys Val Pro Ser Gly Asp
    50                  55                  60

Ser Pro Tyr Val Lys Ala Lys His Val Gln Leu Ile Asp Lys Asp Pro
65                  70                  75                  80

Ser Lys Ser Val Ala Leu Phe Trp Ser Ala Ile Asn Ala Gly Asp Arg
                85                  90                  95

Val Asp Ser Ala Leu Lys Asp Met Ala Ile Val Met Lys Gln Leu Asp
            100                 105                 110

Arg Ser Asp Glu Ala Ile Glu Ala Ile Lys Ser Phe Arg His Leu Cys
```

-continued

```
                115                 120                 125
Thr Pro Leu Ser Gln Glu Ser Leu Asp Asn Val Leu Val Asp Leu Tyr
130                 135                 140
Lys Arg Gly Gly Arg Ile Glu Glu His Ile Glu Leu Leu His His Lys
145                 150                 155                 160
Leu Lys Leu Ile Asp Gly Val Ala Phe Gly Gly Lys Lys Thr Lys
                165                 170                 175
Ile Ala Arg Ser Gln Gly Lys Lys Phe Leu Val Ser Ile Asp Gln Glu
                180                 185                 190
Arg Ser Arg Leu Leu Gly Asn Leu Gly Trp Ala Tyr Met Gln Gln Asn
                195                 200                 205
Asp Tyr Lys Thr Ala Glu Glu Ile Tyr Arg Lys Ala Leu Ser Ile Glu
210                 215                 220
Gln Asp Lys Asn Lys Gln Cys Asn Leu Ala Ile Cys Leu Met Asn Arg
225                 230                 235                 240
Gly Glu Ile Met Glu Ala Lys Ser Leu Leu Gln Thr Val Thr Pro Ser
                245                 250                 255
Ser Thr Glu Arg Glu Leu Val Asp Pro Phe Ile Lys Ser Phe Asp Arg
                260                 265                 270
Ala Tyr Glu Met Leu Ile Glu Leu Glu Ser Lys Ser Cys Pro Asn Arg
                275                 280                 285
Asn Ala Lys Pro Val Ala Ser Ala Ser Pro Ile Glu Glu Pro Leu Leu
290                 295                 300
Leu Lys Lys Gly Ser Tyr Val Cys Asp Asp Arg Leu Asp Ser Phe Gly
305                 310                 315                 320
Lys Gly Arg Leu Asn Arg Glu Val Glu Met Glu Lys Gly Gly Gly
                325                 330                 335
His Ser Cys Arg Lys Ser Leu Phe Ala Asp Lys Gly Asn Lys Glu Asn
                340                 345                 350
Cys Ser Pro Asn Leu Phe Glu Arg Gly Asn Gly Ile Ser Gly Trp Lys
                355                 360                 365
Asn Val Glu Pro Phe Ser Glu Ser Arg Met Glu Glu Gly Ser Thr Arg
370                 375                 380
Lys Asn Val Arg Thr Phe Gly Phe His Arg Tyr Ser Asn Arg Ser Pro
385                 390                 395                 400
Lys Leu Thr Thr Lys Tyr Gly Leu Gln Ser Pro Ser Asp Gly Asp Trp
                405                 410                 415
Arg Arg Arg Ser Arg Asp Asn Asp Ala Asn Lys Asn Gln Ala Thr Ile
                420                 425                 430
Thr Pro Thr Lys Ser Pro Ile Phe Ile Glu Ser Lys Cys Gly Leu Gln
                435                 440                 445
Ser Thr Asp Gly Gly Cys Arg Lys Ser Pro Ile Ser Phe Ala Tyr Gln
                450                 455                 460
Lys Ala His Glu Val Gly Gly Asp Leu Gln Ala Cys Ser Gly Gln His
465                 470                 475                 480
Leu Glu Gln Arg Ser Glu Val Thr Val Thr Asp Ser Ala Ser Lys Tyr
                485                 490                 495
Ile Gly Gly Asn Glu Thr Pro Glu Ala Cys Asn Gly Ile Asp Ser Thr
                500                 505                 510
Thr Glu Gly Ser Thr Ser Lys Tyr Leu Cys Ser Ser Phe Arg Ser Gly
                515                 520                 525
Lys Ser Trp Ala Asp Met Ala Glu Glu Glu Glu Leu Leu Arg Glu
530                 535                 540
```

Cys Lys Asn Asn Ser Ile Ser Thr Trp Glu Tyr Pro Ser Phe Gln Thr
545                 550                 555                 560

Pro Cys Lys Ser Val Asp Arg Trp Asn Asp Glu Lys Phe Phe His Asn
                565                 570                 575

Glu Asn Met Asp Ser Asn Ile Ile Gly Ser Thr Pro Glu Leu Thr Thr
            580                 585                 590

Gln Pro Arg Arg Asp Gly Tyr Thr Gln Thr Leu Ile Arg Lys Leu Glu
        595                 600                 605

Leu Ile Asp Leu Lys Lys Glu Glu His Ile Lys Thr Thr Ala Ser Tyr
    610                 615                 620

Ser Phe Ser Asn Pro Thr Ala Arg Arg Thr Leu Ala Phe Glu Lys Thr
625                 630                 635                 640

Asp Ser Ala Asp Tyr Phe Arg Pro Ser Pro Leu Cys Lys Gln Val Leu
                645                 650                 655

Phe Asn Gly Glu Ser Asp Asn Thr Ala Gly His Gly Lys Asn Ser Met
            660                 665                 670

Pro Val Gly Arg Arg Ser Arg Arg Leu Pro Val Phe Gln Glu Ile Thr
        675                 680                 685

Pro

<210> SEQ ID NO 18
<211> LENGTH: 625
<212> TYPE: PRT
<213> ORGANISM: Phaseolus vulgaris

<400> SEQUENCE: 18

Met Leu Phe Glu Arg Gly Ser Pro Ala Arg Cys Phe Val Thr Pro Pro
1               5                   10                  15

Pro Pro Ser Pro Trp Lys Thr Ile Ser Ser Arg Ser Pro Ser Val Pro
            20                  25                  30

Phe Ser Glu Arg Lys Lys Ser Pro Asn Ser Ala Asn Lys Ser Asp Ile
        35                  40                  45

Phe His Ile Ile His Lys Val Pro Ser Gly Asp Ser Pro Tyr Val Lys
    50                  55                  60

Ala Lys Gln Val Gln Leu Val Asp Lys Asp Pro Gly Arg Ala Ile Ser
65                  70                  75                  80

Leu Phe Trp Ala Ala Ile Asn Ala Gly Asp Arg Val Glu Ser Ala Leu
                85                  90                  95

Lys Asp Met Ala Leu Val Met Lys Gln Leu Asn Arg Ser Asp Glu Ala
            100                 105                 110

Ile Glu Ala Ile Arg Ser Phe Arg His Leu Cys Pro Ser Asp Ser Gln
        115                 120                 125

Asp Ser Leu Asp Asn Ile Leu Val Glu Leu Phe Lys Arg Ser Gly Arg
    130                 135                 140

Val Asp Glu Glu Ile Ser Met Leu His His Lys Leu Lys Leu Ile Glu
145                 150                 155                 160

Asp Gly Ile Thr Phe Val Gly Arg Thr Thr Lys Gln Ala Arg Ser Gln
                165                 170                 175

Gly Lys Lys Ile Gln Ile Thr Ala Glu Gln Glu Ile Ser Arg Ile Leu
            180                 185                 190

Gly Asn Leu Ala Trp Ala Tyr Leu Gln Lys Glu Asp Tyr Lys Thr Ala
        195                 200                 205

Glu Glu His Tyr Arg Arg Ala Leu Ser Phe Glu Val Asp Arg Asn Lys
    210                 215                 220

```
Gln Cys Asn Leu Ala Ile Cys Leu Met His Met Asn Lys Ile Lys Glu
225                 230                 235                 240

Ala Lys Phe Leu Leu Gln Ala Val Arg Thr Ala Lys Asn Arg Lys
            245                 250                 255

Met Asp Glu Ser Phe Val Lys Ser Phe Glu Arg Ala Ser Gln Met Leu
            260                 265                 270

Val Glu Ile Glu Thr Ser Ser Ser Glu Asn Ala Ser Phe Ser Met Thr
            275                 280                 285

Thr Ser Leu Pro Gln Cys Ser Ser Leu Gly Phe Glu Asn Ser Val Arg
            290                 295                 300

Lys Ser Ser Asp Arg Val Lys Arg Thr Glu Asn Gln Ser Asp Lys Ser
305                 310                 315                 320

Glu Gly Asp Val Ser His Ala Arg Arg Leu Tyr Gln Ser Pro Asp
                325                 330                 335

Pro Gly Arg Arg His Leu Asn Leu Tyr Val Pro Thr Lys Pro Lys Arg
            340                 345                 350

Cys Ser Trp Gly Phe Asn Asn Gly Tyr Arg Arg Gly Asp Phe His Ser
            355                 360                 365

Asp Ser Lys Pro Ser Ser Gly Thr Pro Pro Asn Glu Lys His Val Thr
370                 375                 380

Arg Thr Leu Asn Leu Arg Glu Ser Gly Leu Ser Ser Pro Ala Asn Glu
385                 390                 395                 400

Lys Trp Arg Thr Ser Thr Leu Glu Asp Pro Ala Ile Arg Lys Asn Lys
                405                 410                 415

Asp Thr Lys Val Ile Ile Ser Asp Leu Leu His Thr Leu Asn Thr Glu
            420                 425                 430

Ala Val Val Glu Phe Thr Glu Lys Glu Lys Ser Ala Ala Gly Asp Ser
            435                 440                 445

Ser His Arg Ser Ile Met Ser Glu Ser His Ala Met Val Glu Asn Gly
450                 455                 460

Thr Asp Asp Phe Ala Ser Gly Asn Gly Lys Pro His Glu Lys Lys Ser
465                 470                 475                 480

Trp Ala Asp Ile Val Glu Glu Gln Asn Glu Asn Asp Phe Phe
                485                 490                 495

Ser Gly Tyr Ile Asn Phe Asp Gly Glu Asn Gly Ala Glu Val Phe Asn
            500                 505                 510

Asp Glu Asn Glu Asp Ser Asn Ile Met Tyr Gln Ser Pro Trp Pro Gln
            515                 520                 525

Asn Gln Pro Glu Trp Ser Ser Lys Lys Leu Glu Ser Leu Glu Gln Lys
            530                 535                 540

Asp Gly Tyr His Pro Ser Gly Ser Val Ile Leu Ser Arg Asn Pro Thr
545                 550                 555                 560

Ala Arg Arg Ser Leu Cys Phe Asn Pro Glu Leu Ser Ser Glu Ser Ala
                565                 570                 575

Tyr Ala Ile Arg Thr Ser Lys Ser Pro Lys Lys Ala Ser Asn Leu Glu
            580                 585                 590

Asn Arg Asp Thr Leu Val Gly Glu Lys Lys Leu Pro Arg Lys Ser Arg
            595                 600                 605

Leu Gln Val Phe Gln Asp Ile Thr Leu Phe Pro Glu Thr Pro Arg Phe
            610                 615                 620

Ala
625
```

<210> SEQ ID NO 19
<211> LENGTH: 758
<212> TYPE: PRT
<213> ORGANISM: Prunus persica

<400> SEQUENCE: 19

```
Met Trp Thr Arg Asp Lys Ser Leu His Thr Arg Gly Phe Ser Thr Pro
  1               5                  10                  15

Pro Pro Thr Trp Lys Ser Gly Pro Pro Asn Pro Pro Met Val Pro Met
             20                  25                  30

Ser Glu Arg Lys Arg Val Ser Pro Ser Asp Gly Gly Asp Leu Phe His
         35                  40                  45

Val Met His Lys Val Pro Val Gly Asp Ser Pro Tyr Val Arg Ala Lys
     50                  55                  60

Gln Val Gln Leu Ile Glu Lys Asp Pro Ser Lys Ala Ile Ser Leu Phe
 65                  70                  75                  80

Trp Ala Ala Ile Asn Ala Gly Asp Arg Val Asp Ser Ala Leu Lys Asp
                 85                  90                  95

Met Ala Ile Val Met Lys Gln Leu Asn Arg Ser Glu Glu Ala Ile Glu
            100                 105                 110

Ala Ile Lys Ser Phe Arg His Leu Cys Pro His Asp Ser Gln Glu Ser
        115                 120                 125

Leu Asn Asn Val Leu Val Glu Leu Tyr Lys Arg Ala Gly Arg Ile Glu
130                 135                 140

Glu Glu Ile Glu Met Leu Gln Ser Lys Leu Lys His Ile Asp Glu Gly
145                 150                 155                 160

Ile Ala Phe Gly Gly Arg Arg Thr Lys Thr Ala Arg Ser Gln Gly Lys
                165                 170                 175

Lys Val Gln Ile Thr Val Glu Gln Glu Arg Ser Arg Ile Leu Gly Asn
            180                 185                 190

Leu Ala Trp Ala Tyr Leu Gln Gln Gly Asn Tyr Lys Thr Ala Glu Glu
        195                 200                 205

Tyr Tyr Met Lys Ser Leu Ser Leu Glu Leu Asp Lys Asn Lys Gln Cys
    210                 215                 220

Asn Leu Ala Ile Cys Leu Met His Met Asn Arg Leu Ala Glu Ala Lys
225                 230                 235                 240

Ser Leu Leu Gln Val Val Arg Ala Ser Ser Gly Asn Lys Pro Met Asp
                245                 250                 255

Glu Ser Tyr Ala Lys Ser Phe Glu Arg Ala Ile Gln Met Leu Thr Glu
            260                 265                 270

Leu Glu Ala Lys Ser Val Leu Arg Pro Ile Gln Leu Asp Glu Asn Cys
        275                 280                 285

Cys Lys Glu Ile Ser Arg Phe Pro Ile Ser Pro Ile Asn Arg Asn Ser
    290                 295                 300

Lys Gln Gly Asn Ser Leu Thr Asn Glu Gly Gln His Tyr Val Ser Gly
305                 310                 315                 320

Cys Met Ile Ser Arg Arg Trp Ala Asp Gly His Glu Glu Thr Val
                325                 330                 335

Ser Val Asn Lys Trp Lys Lys Asp Cys Tyr Phe Lys Asn Ser Cys Glu
            340                 345                 350

Gly Arg Ser Ser Phe Ser Ser Arg Met Lys Glu Asn Gln Gly Gly Ile
        355                 360                 365

Val Gly Thr Glu Thr Thr Pro Tyr Ser Lys Thr Phe Phe Ser Pro Ala
    370                 375                 380
```

Pro Asp Ile Trp Asn Arg Glu Val Leu Phe Thr Gln Pro Arg Arg Ser
385                 390                 395                 400

Ser Arg Gly Phe Asn Asp Gly His Gln Thr Arg Glu Ile Trp Gly Arg
            405                 410                 415

Gly Val Gly Ser Ser Asn Lys Lys Leu Ser Phe Glu Ser Cys Ser Arg
        420                 425                 430

Thr Glu Asn Met Arg Ala His Val Val Arg Ser Leu Asn Glu Asp Leu
    435                 440                 445

Leu Ala Ser Thr Thr Gly Lys Ser Glu Val Ala Phe Gln Asn Ser Val
450                 455                 460

Ser Ser Ile Ser Ser Pro Ile Ser Arg Asp Leu Arg Arg Pro Gln
465                 470                 475                 480

Lys Asp Ala Ala Val Arg Ser Val Leu Gln Pro Ile Ser Ser Gly Asn
                485                 490                 495

Trp Lys Cys Thr Ser Arg Ala Asn Asp Gly Cys Phe Gln Leu Lys Asp
            500                 505                 510

Glu Ala Val Val Ser Ser Gln Asn Thr Val Asn Gly Asp Trp
        515                 520                 525

Arg Arg Thr Ser Trp Glu Asn Asp Gly Met Lys Lys Ser Ala Glu Pro
530                 535                 540

Leu Met Val Gly Glu Asp Ala Lys Ala Leu Glu Ile Ser Thr Asp Gly
545                 550                 555                 560

Gly Pro Asn Gln Ser Ser Asp Thr Thr Ala Phe Val Glu Asp Cys Phe
            565                 570                 575

Gly Glu Asn Thr Ser Ser Lys Val Asp Asp Val His Gln Pro Ile Ala
        580                 585                 590

Glu Asn Gln Lys Pro Ala Pro Asp Phe Ser Met Tyr Ser Lys Cys Lys
    595                 600                 605

Lys Ser Trp Ala Asp Met Val Glu Glu Glu Gln Glu Leu Leu Asn
610                 615                 620

Gly Arg Thr Glu Tyr Phe Asp Ser Trp Tyr Thr Glu Asp Gly Phe Asn
625                 630                 635                 640

Asn Glu Asn Leu Asn Cys Asn Ile Thr Pro Glu Ser Pro Cys Leu Gln
            645                 650                 655

Ser Gln Met Lys Ser Leu Gly Gln Lys Leu Gln Ser Thr Asp Leu Val
        660                 665                 670

Asp Glu Tyr Val Ser Gly Asn Ala Ala Ser Ser Arg Asn Ser Thr Val
    675                 680                 685

Arg Arg Ser Leu Cys Phe Gly Gln Gln Gln Glu Gln Glu Ser Val Asp
690                 695                 700

Tyr Ile Ser Ser Ser Pro Val Pro Lys Glu Ala Leu Asn Phe Glu Gly
705                 710                 715                 720

Ser Asp Ser Val Gln Ala Asn Gly Lys Gly Ser Ile Tyr Gly Lys Asn
            725                 730                 735

Ser Ser Phe Ser Arg Arg Lys Arg Leu Gln Ser Phe Gln Asp Ile Thr
        740                 745                 750

Glu Phe Gln Asp Ser Pro
        755

<210> SEQ ID NO 20
<211> LENGTH: 649
<212> TYPE: PRT
<213> ORGANISM: Gossypium raimondii

<400> SEQUENCE: 20

```
Met Trp Ser Ser Asp Lys His Cys Pro Ala Arg Gly Phe Leu Thr Pro
1               5                   10                  15

Gln Pro Pro Ala Trp Lys Lys Val Gln Ser Thr Thr Val Leu Pro Met
            20                  25                  30

Ser Glu Arg Lys Arg Ile Ser Pro Ala Asn Asn Gly Asp Cys Phe His
        35                  40                  45

Val Ile His Lys Val Pro Ala Ser Asp Ser Pro Tyr Gly Arg Ala Lys
    50                  55                  60

His Val Gln Leu Ile Asp Lys Asp Pro Ser Lys Ala Val Ser Leu Phe
65                  70                  75                  80

Trp Ala Ala Ile Asn Ala Gly Asp Arg Val Asp Ser Ala Leu Lys Asp
                85                  90                  95

Met Ala Val Val Met Lys Gln Leu Asn Arg Ser Asp Glu Ala Ile Glu
            100                 105                 110

Ala Ile Lys Ser Phe Arg His Leu Cys Pro Tyr Asp Ser Gln Glu Ser
        115                 120                 125

Leu Asp Asn Val Leu Val Glu Leu Tyr Lys Arg Ser Gly Arg Val Asp
    130                 135                 140

Glu Glu Ile Glu Ile Leu Leu Asn Lys Leu Arg Asn Ile Glu Glu Gly
145                 150                 155                 160

Thr Val Phe Gly Gly Lys Lys Thr Lys Ile Ala Arg Ser Gln Gly Lys
                165                 170                 175

Lys Ile Gln Ile Thr Ile Glu Gln Glu Lys Ser Arg Ile Leu Gly Asn
            180                 185                 190

Leu Ala Trp Ala Tyr Leu Gln Gln His Asn Tyr Gly Ile Ala Glu Gln
        195                 200                 205

His Tyr Arg Lys Ala Leu Ser Leu Glu Pro Asp Lys Asn Lys Gln Cys
    210                 215                 220

Asn Leu Ala Ile Cys Leu Met His Met Asn Arg Leu Gly Glu Ala Lys
225                 230                 235                 240

Ser Leu Leu Gln Asp Val Lys Val Ser Ala Gly Thr Glu Glu Met Asp
                245                 250                 255

Glu Ser Tyr Ser Lys Ser Tyr Glu Arg Ala Met Glu Ile Leu Met Gln
            260                 265                 270

Val Glu Thr Gln Ser Lys Leu Glu Pro Ala Gly Ala Gln Glu Pro Glu
        275                 280                 285

Lys Gly Asn Glu Thr Arg Arg Cys Leu Thr Ser Cys Arg Asp Arg Ser
    290                 295                 300

Leu Lys Glu Ala Ser Val Phe Leu Pro Arg Asn Gly Asp Asn Ile Pro
305                 310                 315                 320

Trp Cys Ile Glu Lys Asn Gly Asn Leu Ser Gly Tyr Asp Asp Thr Ser
                325                 330                 335

Ser Ser Gln Cys Thr Pro Ile Gly Leu Lys Gly Ser Phe Gln Cys Ser
            340                 345                 350

Pro Gln Thr Met Leu Ser Glu Lys Trp Arg Lys Gly Ser Tyr Phe Glu
        355                 360                 365

Ser Pro Ser Glu Gly Ser Val Tyr Ser Ser Lys Leu Lys Glu Ser
    370                 375                 380

Trp Arg Tyr Ser Ala Gly Gln Glu Val Gly Ser Ala His Lys Asn Met
385                 390                 395                 400

Tyr Ala Ser Leu Ala Ala Ser Arg Lys Asn Ser Glu Lys Val Leu Leu
                405                 410                 415
```

```
Thr Gln Pro Arg Arg Cys Ser Trp Gly Phe Asn Thr Ala Asp Gln Arg
            420                 425                 430

Arg Gly Gly Arg Trp Gly Glu Asp Thr Thr Val Arg Asn Ser Ile Arg
        435                 440                 445

Lys Leu Ser Phe Glu Gln Thr Thr Thr Glu Ser Val Pro Ser Pro
    450                 455                 460

Ser Ile Gln Lys Leu Lys Glu Glu Pro Leu Ser Ser Ser Asn Ala Lys
465                 470                 475                 480

Ser Glu Asn Tyr Ser Ala Val Gly Leu Gly Glu Glu Ala Gln Glu
                485                 490                 495

Gly Leu Ser Gly Val Leu Phe Thr Gln Pro Arg Asn Ser Leu Ser Trp
            500                 505                 510

Leu Asn Asn Arg Asp Gln Arg Gly Arg Cys Ala Glu Glu Ser Ile
        515                 520                 525

Asp Gly Ser Phe Ser Lys Leu Ser Ser Val Thr Thr His Ser Val
    530                 535                 540

Gln Ser Leu Asn Val Glu Pro Leu Val Ser Ser Lys Asp Glu Ser Glu
545                 550                 555                 560

Ile Gly Val Glu Lys Pro Ala Asp Ala Ala Ser Asn Lys Lys Thr Trp
                565                 570                 575

Ala Asp Met Val Glu Glu Glu Lys Asp Glu Phe Leu Asn Asp Glu
            580                 585                 590

Asn Leu Asn Ser Asn Ile Ile Tyr Gln His Pro Asp Arg Ser Lys His
        595                 600                 605

His Ile Glu Asn Ile Thr Gln Gln Leu Glu Ser Phe Gly Val Lys Gly
    610                 615                 620

Gly Tyr Asn Ala Ser Ala Asn Thr Val Ser Leu Arg Arg Asn Arg Leu
625                 630                 635                 640

Gln Val Phe Arg Asp Ile Thr Ser Thr
                645

<210> SEQ ID NO 21
<211> LENGTH: 614
<212> TYPE: PRT
<213> ORGANISM: Solanum lycopersicum

<400> SEQUENCE: 21

Met Trp Arg Asn Asn Glu Arg Val Tyr Met Thr Pro Ala Arg Gly Phe
1               5                   10                  15

Leu Thr Pro Pro Lys Trp Arg Ser Pro Ala Thr Glu Lys Asp Gln
            20                  25                  30

Lys Trp Pro Thr His Ala Gln Ser Ala Lys Ala Asp Leu Phe His Val
    35                  40                  45

Ile His Lys Val Pro Ser Gly Asp Ser Pro Tyr Val Arg Ala Lys His
    50                  55                  60

Val Gln Leu Ile Asp Lys Asp Pro Gly Lys Ala Val Ser Leu Phe Trp
65                  70                  75                  80

Ala Ala Ile Asn Ser Gly Asp Arg Val Asp Ser Ala Leu Lys Asp Met
                85                  90                  95

Ala Val Val Met Lys Gln Leu Asp Arg Ser Asp Glu Ala Ile Glu Ala
            100                 105                 110

Ile Lys Ser Phe Arg Asn Leu Cys Pro Ser Glu Ser Gln Glu Ser Ile
        115                 120                 125

Asp Asn Ile Leu Ile Glu Leu Tyr Lys Arg Ser Gly Arg Leu Glu Glu
```

-continued

```
            130                 135                 140
Glu Ile Glu Leu Leu Glu Leu Lys Leu Lys Asn Val Glu Glu Gly Ile
145                 150                 155                 160

Ala Phe Gly Gly Lys Arg Thr Lys Ile Ala Arg Ser Gln Gly Lys Lys
                165                 170                 175

Val Gln Ile Thr Ile Glu Lys Glu Tyr Ala Arg Leu Leu Gly Asn Leu
                180                 185                 190

Ala Trp Ser Tyr Met Gln Leu Asn Asn Phe Lys Leu Ala Glu Glu Tyr
            195                 200                 205

Tyr Arg Lys Ala Leu Ser Leu Glu Ser Asp Lys Asn Lys Gln Ser Asn
        210                 215                 220

Leu Ala Ile Cys Leu Met His Met Asn Lys Ile Ala Glu Ala Arg Phe
225                 230                 235                 240

Leu Leu Gln Ser Ile Lys Thr Ser Asp Arg Arg Gln Met Asp Glu Ser
                245                 250                 255

Cys Thr Lys Ser Phe Glu Arg Ala Thr Gln Met Leu Ala Glu Leu Glu
                260                 265                 270

Ser His Gly Ile Gln Asn Ser Lys Glu Gln Val Glu Glu Met Arg Glu
            275                 280                 285

Val Arg Ile Asp Ser Ser Thr Ser Asp Glu His Asp Arg Arg Gly His
        290                 295                 300

Glu Lys Thr His Pro Pro Pro Phe Thr Ala Ser Gly Pro Pro Lys His
305                 310                 315                 320

Phe Leu Thr Gln Pro Arg Arg Tyr Ser Cys Ser Leu Asn Asp Gly Gly
                325                 330                 335

Trp Leu Asn Lys Asp Ser Val Ser Ala Cys Ser Arg Arg Leu Leu Phe
                340                 345                 350

Glu Gln Thr Ser Asn Asn Glu Asn Val Gln Leu Val Val Asn His Asn
            355                 360                 365

Phe Asn Lys Leu Ile Ser Val Asn Asp Ile Ser Glu Gly Ala Ser Val
        370                 375                 380

Val Cys Gly Gln Val Phe Ser Arg Ser Trp Gly Asn Gly Ala Asn Val
385                 390                 395                 400

Arg Ser Glu Cys Asp Leu Gln Pro Pro Tyr Ser Lys Trp Lys Asn Asn
                405                 410                 415

Ser Ser Gly Asn Asp Gly Ser Asp Gln Ile Ser Leu Glu Leu Ser Arg
                420                 425                 430

Ser Pro Thr Glu Ser Leu Pro Asp Ile Thr Ser Ala Arg Lys Cys Ser
            435                 440                 445

Glu Asn Gly Ser Lys Asp Cys Trp Ser Ser Thr Leu Thr Tyr Arg Asp
        450                 455                 460

Met Val Thr Leu Glu Asp Thr Thr Glu His Leu Asp Ser Thr Ser Leu
465                 470                 475                 480

Lys Pro Leu Asn Leu Pro Ala Cys Thr Ser Lys Lys Ser Trp Ala Asp
                485                 490                 495

Met Val Glu Glu Asp Glu Leu Gly Leu Gln Phe His Glu Thr Pro Gly
                500                 505                 510

Lys Tyr Ser Asp Glu Asn Glu Ile Asp Ala Asn Ile Ile Asn Leu
            515                 520                 525

Ser Gln Asn Ile Asp Thr Leu Cys Leu Asn Glu Gly Tyr His Thr Gln
        530                 535                 540

Pro Gly Arg Glu Ala Arg Arg Ser Leu Cys Phe Asp His Asn Asp Arg
545                 550                 555                 560
```

```
Lys Glu Lys Cys Ser Ser Gly Phe Gln Gly Lys Glu Leu Lys Ser Gly
                565                 570                 575

Ser Leu Asn Ser Leu Pro Pro Ile Gly Asp Ile Ala Tyr Gln Thr Pro
            580                 585                 590

Val Thr Leu Met Arg Arg Asn Arg Leu Gln Val Phe Arg Asp Ile Thr
        595                 600                 605

Pro Glu Ser Pro Lys Pro
        610

<210> SEQ ID NO 22
<211> LENGTH: 614
<212> TYPE: PRT
<213> ORGANISM: Solanum tuberosum

<400> SEQUENCE: 22

Met Trp Arg Asn Asn Glu Arg Val Tyr Met Ser Pro Ala Arg Gly Phe
1               5                   10                  15

Leu Thr Pro Pro Lys Trp Arg Ser Pro Ala Ser Asp Lys Asp Gln
            20                  25                  30

Arg Trp Pro Thr His Ala Gln Ser Ala Lys Ala Asp Leu Phe His Val
        35                  40                  45

Ile His Lys Val Pro Ser Gly Asp Ser Pro Tyr Val Arg Ala Lys His
    50                  55                  60

Val Gln Leu Ile Asp Lys Asp Pro Gly Lys Ala Ile Ser Leu Phe Trp
65                  70                  75                  80

Ala Ala Ile Asn Ser Gly Asp Arg Val Asp Ser Ala Leu Lys Asp Met
                85                  90                  95

Ala Val Val Met Lys Gln Leu Asp Arg Ser Asp Glu Ala Ile Glu Ala
            100                 105                 110

Ile Lys Ser Phe Arg Asn Leu Cys Pro Ser Glu Ser Gln Glu Ser Ile
        115                 120                 125

Asp Asn Ile Leu Ile Glu Leu Tyr Lys Arg Ser Gly Arg Leu Glu Glu
    130                 135                 140

Glu Ile Glu Leu Leu Glu Leu Lys Leu Lys Asn Val Glu Glu Gly Ile
145                 150                 155                 160

Ala Phe Gly Gly Lys Arg Thr Lys Ile Ala Arg Ser Gln Gly Lys Lys
                165                 170                 175

Val Gln Ile Thr Ile Glu Lys Glu Tyr Ala Arg Leu Leu Gly Asn Leu
            180                 185                 190

Ala Trp Ser Tyr Met Gln Leu Asn Asn Phe Lys Leu Ala Glu Glu Tyr
        195                 200                 205

Tyr Arg Lys Ala Leu Ser Leu Glu Ser Asp Lys Asn Lys Gln Ser Asn
    210                 215                 220

Leu Ala Ile Cys Leu Met His Met Asn Lys Ile Ala Glu Ala Arg Phe
225                 230                 235                 240

Leu Leu Gln Ser Ile Lys Ala Ser Asp Arg Trp Gln Met Asp Glu Ser
                245                 250                 255

Cys Thr Lys Ser Phe Glu Arg Ala Thr Gln Met Leu Ala Glu Leu Glu
            260                 265                 270

Thr His Gly Ile Gln Asn Ser Lys Glu Gln Val Glu Met Arg Glu
        275                 280                 285

Val Arg Ile Asp Ser Ser Thr Ser Asp Glu His Asp Cys Arg Gly His
    290                 295                 300

Glu Lys Thr His Pro Pro Pro Phe Thr Ala Ser Gly Pro Pro Lys His
```

```
305                 310                 315                 320
    Phe Leu Thr Gln Pro Arg Arg Tyr Ser Cys Ser Leu Asn Asp Gly Gly
                    325                 330                 335

Trp Leu Asn Lys Asp Ser Val Ser Ala Cys Ser Arg Arg Leu Leu Phe
                    340                 345                 350

Glu Gln Thr Ser Asn Asn Glu Asn Val Gln Leu Val Asn His Asn
                    355                 360                 365

Phe Asn Lys Leu Ile Ser Ala Asn Asp Met Ser Glu Gly Ala Ser Leu
                    370                 375                 380

Val Arg Gly Gln Val Leu Thr Arg Ser Trp Gly Asn Gly Ala Asn Val
    385                 390                 395                 400

Glu Ser Glu Cys Asp Leu Gln Pro Pro Tyr Ser Lys Trp Lys Asn Asn
                    405                 410                 415

Ser Ser Gly Asn Asp Gly Ser Asp Gln Ile Ser Leu Glu Leu Ser Lys
                    420                 425                 430

Ser Pro Thr Glu Ser Leu Ala Asp Ile Thr Ser Ala Arg Lys Tyr Ser
                    435                 440                 445

Gly Asp Gly Ser Lys Asp Cys Trp Ser Ser Thr Leu Thr Tyr Arg Asp
                    450                 455                 460

Thr Val Thr Leu Glu Asp Thr Thr Glu His Leu Glu Ser Thr Asn Leu
    465                 470                 475                 480

Lys Pro Leu Asn Leu Pro Ala Cys Thr Ser Lys Lys Ser Trp Ala Asp
                    485                 490                 495

Met Val Glu Glu Asp Glu Leu Gly Leu Gln Phe His Glu Thr Pro Gly
                    500                 505                 510

Lys Tyr Ser Asp Glu Asn Glu Asn Ile Asp Ser Asn Ile Ile Asn Leu
                    515                 520                 525

Ser Gln Asn Ile Asp Thr Leu Arg Leu Asn Glu Gly Tyr His Thr Gln
                    530                 535                 540

Pro Gly Arg Glu Ala Arg Arg Ser Leu Cys Phe Asp Gln Asn Asp Arg
    545                 550                 555                 560

Lys Glu Lys Cys Ser Ser Asp Phe Gln Gly Lys Val Leu Lys Ser Gly
                    565                 570                 575

Ser Leu Asn Ser Leu Pro Pro Ile Gly Asp Ile Ala Tyr Gln Thr Pro
                    580                 585                 590

Val Thr Leu Met Arg Arg Asn Arg Leu Gln Val Phe Arg Asp Ile Thr
                    595                 600                 605

Pro Glu Ser Pro Lys Pro
                    610

<210> SEQ ID NO 23
<211> LENGTH: 683
<212> TYPE: PRT
<213> ORGANISM: Setaria italica

<400> SEQUENCE: 23

Met Pro Ser Gly Gly Arg Arg Leu Pro Pro Trp Thr Ser Pro Arg Ser
1               5                   10                  15

Ala Gly Ala Pro Arg Trp Ser Pro Ala Ala Gly Thr Pro Val Ala Gly
                20                  25                  30

Ala Gly Cys Gly Pro Val Ser Gly Tyr Arg Thr Pro Pro Val Ser Ala
                35                  40                  45

Gly Gly Cys Phe Gly Thr Arg Val Thr Pro Pro Thr Gly Gly Ala
                50                  55                  60
```

-continued

```
Arg Val Thr Pro Pro Ser Thr Gly Gly Cys Ser Ser Arg Pro Pro Arg
 65                  70                  75                  80

Pro Pro Pro Ser Leu Asp Ser Pro Tyr Val Arg Ala Lys Gln Ala Gln
                 85                  90                  95

Val Ile Glu Lys Asp Pro Asn Lys Ala Val Pro Leu Phe Trp Ala Ala
            100                 105                 110

Ile Asn Ser Gly Asp Arg Ile Glu Ser Ala Leu Lys Asp Met Ala Asn
            115                 120                 125

Val Leu Lys Gln Ala Asn Arg Ala Glu Glu Ala Ile Glu Ala Ile Arg
    130                 135                 140

Ser Phe Arg Asp Arg Cys Pro Tyr Glu Ala Gln Asp Ser Leu Asp Asn
145                 150                 155                 160

Ile Leu Leu Asp Leu Tyr Lys Lys Cys Gly Arg Thr Glu Glu Gln Ile
                165                 170                 175

Glu Met Leu Thr Ile Lys Leu Arg Val Val Asp Glu Glu Leu Ala Ser
            180                 185                 190

Gly Arg Trp Lys Thr Lys Leu Ser Lys Ser His Gly Arg Val Val Tyr
            195                 200                 205

Leu Ser Leu Arg Asp Glu Lys Ala Arg Leu Leu Gly Asn Leu Ala Trp
    210                 215                 220

Ala Tyr Met Gln Ser Glu Asn Tyr Glu Glu Ala Glu Met Leu Tyr Arg
225                 230                 235                 240

Gln Ala Leu Ala Ile Glu Ala Asp Tyr Asn Lys Glu Cys Asn Leu Ala
                245                 250                 255

Ile Cys Leu Met Lys Thr Gly Lys Leu Ala Glu Ala Lys Tyr Leu Leu
            260                 265                 270

Gln Ala Ile Pro Tyr Asn Cys Asp Asp Glu Ser His Val Lys Ser Leu
            275                 280                 285

Ser Arg Ala Thr Glu Met Leu Arg Asp Leu Glu Leu Gln Ser Leu Pro
    290                 295                 300

Ser Pro Ile Thr Gln Met Lys Ser Lys Glu Ser Arg Ile Leu Leu Ala
305                 310                 315                 320

Thr Asp Val Glu Ile Leu Glu Asp Pro Gln Pro Gln Thr Leu Ser Thr
                325                 330                 335

Pro Leu Ser Gln Leu Lys Tyr Lys Glu Pro His Ile Ser Val Ser Ala
            340                 345                 350

Asn Ala Glu Gln His Glu Lys Cys Ser Ser Trp Phe Pro Ser Pro Ile
            355                 360                 365

Thr Gln Leu Lys Arg Glu Glu Pro Arg Ile Leu Val Thr Val Asp Ala
    370                 375                 380

Glu Lys Asn Glu Gly Cys Ala Glu Phe Gln Asp Leu Ser Arg Leu Phe
385                 390                 395                 400

Asn Asp Ala Ala Thr Pro His Ser Ile Leu Glu Lys Leu Arg Lys Arg
                405                 410                 415

Leu Val Asn Glu Ala Pro Lys Ser Ile His Asp Gln Ile Gln Thr
            420                 425                 430

His Thr Pro Thr Glu Cys Leu Pro Asn Ser Glu Gly Asn His Asn Ala
            435                 440                 445

Ser Glu Asn Pro Val Gln Gly Gly Lys Leu Leu Thr Lys Gly Val Arg
    450                 455                 460

Lys Thr Trp Ala Asp Met Val Asp Glu Glu Gln Gln Leu Gly Glu
465                 470                 475                 480

Asp Lys Ser Trp Thr Asp Met Val Ala Lys Gly Glu His Gln Leu Arg
```

```
                485                 490                 495
Asn Asp Lys Leu Thr Val Gly Val Gly Thr Thr Glu Gln Thr Glu Ser
                500                 505                 510

Ser Lys His Ala Ser Lys Gln Glu Tyr Arg Thr Pro Pro Ser Gln
            515                 520                 525

Gly Ser Ser Thr Leu His Arg Pro Val Ile Gly His Gln Gln Gly
        530                 535                 540

Phe Ser Ala Asn Ser Trp Arg Ser Asn Ser Lys Ile Ser Thr Asp
545                 550                 555                 560

Asn Lys Val Asn Trp Asp Leu Val Arg Ala Pro Thr Trp Ser Lys
                565                 570                 575

His Lys Val Gln Asp His Ser Gly Arg Val Cys Gln Arg Pro Asn Ala
            580                 585                 590

Ala His Leu Lys Glu Asn Thr Ser Gly Ser Lys Gln Ala Pro Trp Arg
        595                 600                 605

Ser Ser Ala Ser Gln Arg Ala Leu Phe Pro Asp Trp Lys Ser Lys Gly
        610                 615                 620

Glu Gly Tyr Gly His Gly Tyr Val Pro Phe Gly Asp Asn Glu His Ser
625                 630                 635                 640

Gln Gly Ser Ser Arg Thr Glu Ala Thr His Arg Trp His Asn Asn Ala
                645                 650                 655

Ala Gly Thr Val Ser Trp Arg Pro Gln Asn Arg Leu Arg Val Phe Gln
            660                 665                 670

Glu Ile Thr Asn Glu Ile Asn Gln Asn Val Val
        675                 680

<210> SEQ ID NO 24
<211> LENGTH: 717
<212> TYPE: PRT
<213> ORGANISM: Brachypodium distachyon

<400> SEQUENCE: 24

Met Arg Ser Gly Gly Arg Arg Leu Pro Pro Trp Thr Ser Pro Arg Gly
1               5                   10                  15

His Ala Ala Ala Glu Val Val Ala Pro Thr Gly Trp Ser Pro Arg Thr
                20                  25                  30

Pro Ala Ala Gly Gly Gly Ser Gly Ser Tyr Val Thr Pro Pro Leu
            35                  40                  45

Thr Ala Gly Cys Cys Cys Ser Ser Ser Tyr Arg Val Thr Pro Pro
        50                  55                  60

Ser Ser Gly Gly Gly Cys Thr Ser Leu Leu Thr Pro Pro Val Ser Gly
65                  70                  75                  80

Gly Gly Cys Ser Arg Pro Pro Arg Ala Pro Ala Val Val Asp Ser
                85                  90                  95

Pro Tyr Val Arg Ala Lys Gln Ala Gln Leu Ile Glu Lys Asp Pro Asn
                100                 105                 110

Lys Ala Val Pro Leu Phe Trp Ala Ala Ile Asn Ser Gly Glu Arg Ile
            115                 120                 125

Glu Ser Ala Leu Lys Asp Met Ala Thr Val Leu Lys Gln Ala Asn Arg
        130                 135                 140

Ala Glu Glu Ala Ile Glu Ala Ile Arg Ser Phe Arg Asp Arg Cys Pro
145                 150                 155                 160

Asn Glu Ala Gln Asp Ser Leu Asp Asn Val Leu Leu Asp Leu Tyr Lys
                165                 170                 175
```

```
Lys Cys Gly Arg Thr Lys Glu Gln Ile Glu Met Leu Thr Ile Lys Leu
                180                 185                 190

Arg Met Val Asp Glu Asp Leu Ala Ser Gly Arg Trp Lys Thr Lys Leu
            195                 200                 205

Ser Lys Ser His Gly Arg Val Val Tyr Leu Ser Leu Arg Asp Glu Lys
        210                 215                 220

Ala Arg Leu Leu Gly Asn Leu Ala Trp Ala His Met Gln Ser Glu Asn
225                 230                 235                 240

Tyr Glu Glu Ala Glu Met Leu Tyr Arg Gln Ala Leu Ala Ile Glu Ala
                245                 250                 255

Asp Tyr Asn Lys Glu Cys Asn Leu Ala Val Cys Leu Met Lys Thr Gly
            260                 265                 270

Lys Val Ala Glu Ala Lys Tyr Leu Leu Gln Ala Ile Pro Tyr Asn Ser
        275                 280                 285

Ser Asp Glu Lys His Val Arg Ser Phe Ala Arg Ala Thr Glu Met Ile
        290                 295                 300

Lys Glu Leu Glu Ser Gln Ala Leu Pro Ser Pro Ile Thr Gln Met Lys
305                 310                 315                 320

Ser Lys Asp Ser Arg Ile Leu Leu Ala Thr Asp Ala Glu Asn Leu Asp
                325                 330                 335

Tyr Ile Gln Pro Glu Ile Leu Ser Thr Ser Thr Gln Leu Gln Tyr
            340                 345                 350

Glu Glu Pro Glu Phe Ser Val Ser Ala Asp Thr Glu Lys Gln Val Asp
        355                 360                 365

Cys Asn Ser Gln Glu Leu Pro Ser Pro Ile Thr Gln Leu Lys Arg Lys
        370                 375                 380

Val Pro Gln Ile Met Val Asp Ser Glu Lys Asn Gly Glu Cys Pro Glu
385                 390                 395                 400

Glu Asn Gln Asp Ile Ser Arg Leu Phe Asn Asp Ala Ala Thr Pro Gln
                405                 410                 415

Ser Leu Leu Glu Lys Leu Arg Lys Arg Leu Val Lys Lys Asp Arg Pro
            420                 425                 430

Asn Ile Ser Ile Gln His Gln Ala Gln Thr Pro Ser Ser Thr Glu Cys
            435                 440                 445

Leu Pro Ile Cys Asn Gly Ala Thr Asp Ala Ser Asp Asn His Leu Gln
450                 455                 460

Glu Gly Gln Ser Ser Val Gly Gly Ala Arg Lys Thr Trp Ala Asp Met
465                 470                 475                 480

Val Glu Glu Asp Glu Gln Gln Leu Gly Asp Gly Lys Ser Gly Thr Ala
                485                 490                 495

Gln Asn Glu Ser Ser Lys Gln Ala Ser Glu Gln Arg Tyr Ile Thr Pro
            500                 505                 510

Pro Ser Ser Gln Ala Asn Ser Thr Leu Gln Thr Pro Ala Ala Gly Val
        515                 520                 525

Arg Leu Gln Ser Ser Ala Gly Ser Trp Arg Arg Lys Asp Ser Thr
530                 535                 540

Gly Glu Asn Val Asn Arg Lys Phe Val Arg Thr Ala Pro Ala Trp Arg
545                 550                 555                 560

Gln Gln Lys Val Gln Asp His Ser Asn Arg Val Cys Gln Arg Leu Asn
                565                 570                 575

Thr Ile His Leu Gly Glu Lys Ala Gln Gly Gln Gly Ala Glu Gln Thr
            580                 585                 590

Pro Trp Arg Ser Ser Ala Ala Gln Arg Ser Leu Phe His Gly His Leu
```

```
                    595                 600                 605
Pro Ser Gly Glu Ser Gly Arg Cys His Val Ser Gly His Thr Glu Ala
    610                 615                 620
Val Asn Arg Trp Pro Lys Asn Ala Ala Ala Ile Thr Arg Pro Trp Arg
625                 630                 635                 640
Ala Gln Asn Arg Leu Arg Val Phe Gln Glu Ile Thr Asn Glu Met Asn
                645                 650                 655
Arg Asn Val Ala Tyr Glu His Cys Cys Leu Pro Cys Met Gln Thr Leu
            660                 665                 670
Cys Ala Cys Thr Phe Trp Arg Tyr Cys Leu Asp Val Thr Ala Trp Phe
        675                 680                 685
Ile Cys Cys Asn Val Leu His Val Ala Phe Ile Cys Tyr Cys Cys Cys
    690                 695                 700
Cys Trp Leu Ala Gly Trp Leu Ala Gly Gln Phe Pro Ala
705                 710                 715

<210> SEQ ID NO 25
<211> LENGTH: 815
<212> TYPE: PRT
<213> ORGANISM: Oryza sativa japonica

<400> SEQUENCE: 25

Met Pro Ser Gly Gly Arg Arg Leu Pro Pro Trp Thr Ser Pro Arg Gly
1               5                   10                  15
Ala Ala Pro Arg Trp Ser Pro Cys Thr Pro Ala Gly Ala Asp Gly Ser
                20                  25                  30
Gly Arg Ala Ala His Ala Thr Pro Pro Ala Ser Gly Gly Cys Ser Ser
            35                  40                  45
His Val Thr Pro Pro Ala Ser Gly Gly Gly Cys Tyr Gly Tyr Arg
        50                  55                  60
Val Thr Pro Pro Thr Ser Gly Gly Cys Ser Arg Pro Pro Arg Ala Pro
65                  70                  75                  80
Leu Ser Ser Val Asp Ser Pro Tyr Val Arg Ala Lys Gln Ala Gln Val
                85                  90                  95
Ile Glu Lys Asp Pro Asn Lys Ala Val Pro Leu Phe Trp Ala Ala Ile
                100                 105                 110
Asn Ser Gly Asp Arg Ile Glu Ser Ala Leu Lys Asp Met Ala Thr Val
                115                 120                 125
Leu Lys Gln Ala Asn Arg Ala Glu Glu Ala Ile Glu Ala Ile Arg Ser
    130                 135                 140
Phe Arg Asp Arg Cys Pro Asn Glu Ala Gln Glu Ser Leu Asp Asn Ile
145                 150                 155                 160
Leu Leu Asp Leu Tyr Lys Lys Cys Gly Arg Thr Lys Glu Gln Ile Glu
                165                 170                 175
Met Leu Thr Leu Lys Leu Arg Ile Val Asp Glu Glu Leu Ala Ser Gly
                180                 185                 190
Arg Trp Lys Thr Lys Leu Ser Lys Ser His Gly Arg Val Val Tyr Leu
        195                 200                 205
Ser Leu Arg Asp Glu Lys Ala Arg Leu Leu Gly Asn Leu Ala Trp Ala
    210                 215                 220
His Met Gln Ser Glu Asn Tyr Asp Glu Ala Glu Met Leu Tyr Arg Gln
225                 230                 235                 240
Ala Leu Ala Ile Glu Ala Asp Tyr Asn Lys Glu Cys Asn Leu Ala Ile
                245                 250                 255
```

```
Cys Leu Ile Lys Thr Gly Lys Val Ala Glu Ala Lys Tyr Leu Leu Gln
            260                 265                 270

Ser Ile Pro Asp Asn Cys Ser Asp Glu Ser His Val Arg Ser Leu Ala
        275                 280                 285

Arg Ala Arg Glu Met Leu Met Glu Leu Glu Ser Pro Thr Leu His Ser
    290                 295                 300

Pro Ile Thr Gln Met Lys Ser Lys Glu Ser Leu Ile Trp Leu Ala Ile
305                 310                 315                 320

Asp Ala Glu Asn Leu Gly His Leu Gln Pro Gln Val Ser Thr Ala
                325                 330                 335

Leu Thr Gln Leu Lys Ser Glu Glu Pro His Ile Ser Val Ala Ala Asp
        340                 345                 350

Ala Glu Lys Gln Glu Asp Cys Asn Ser Gln Val Phe Pro Ser Pro Ile
            355                 360                 365

Thr Gln Met Lys Arg Glu Glu Pro Glu Ser Leu Ile Ala Thr Ser Gly
    370                 375                 380

Glu Asn Asn Glu Lys Cys Leu Asn Glu Tyr Gln Asp Leu Ser Arg Leu
385                 390                 395                 400

Phe Asn Asp Ala Ala Thr Pro Gln Ser Leu Leu Glu Lys Leu Arg Lys
                405                 410                 415

Arg Leu Val Lys Glu Asp Thr Leu Asn Ile Ser Ile Gln His Gln Val
        420                 425                 430

Gln Ile Pro Ser Phe Val Glu Cys Leu Pro Asn Ser Gly Gly Ser Thr
            435                 440                 445

Asp Ala Gly Glu Asn Thr Arg Pro Glu Gly Lys Ala Leu Val Asn Gly
        450                 455                 460

Val Arg Lys Thr Trp Ala Asp Met Val Glu Glu Asp Glu Arg Gln Leu
465                 470                 475                 480

Gly Asp Val Ser Ser Thr Ile Gly Met Asp Thr Thr Lys Arg Asn Val
                485                 490                 495

Ser Cys Lys His Ala Asn Glu Glu Met Tyr Arg Thr Pro Ser Phe Ser
        500                 505                 510

Gln Glu Ser Ser Ala Leu Lys Arg Ser Ser Val Asp Asp His Pro Gln
            515                 520                 525

Ser Ser Ser Ala Asp Ser Trp Arg His Ser Asp Ser Lys Ile Ser Thr
530                 535                 540

Asp Glu Asn Val Asn Met Lys Phe Val Arg Thr Ala Pro Gln Trp Arg
545                 550                 555                 560

Gln Gln Lys Val Gln Asp Tyr Ser Asn Arg Val Ser Gln Arg Leu Asp
                565                 570                 575

Thr Ser His Leu Ser Asp Arg Ala Glu Gly Thr Glu Gln Pro Pro Trp
        580                 585                 590

Arg Ser Ser Thr Ala Gln Arg Ser Leu Phe Pro Asp Trp Lys Ser Lys
            595                 600                 605

Cys Glu Arg Tyr Gly His Gly Tyr Val Pro Phe Gly Asp Asn Glu His
610                 615                 620

Phe Gln Gly Ser Ser His Phe Glu Ala Thr Asn Arg Trp Pro Lys Asn
625                 630                 635                 640

Ala Arg Pro Trp Arg Pro Gln Asn Arg Leu Trp Val Phe Gln Glu Ile
                645                 650                 655

Thr Asn Glu Ile Asn Gln Lys Gln Thr Arg Ala Leu Trp Leu Thr Ile
        660                 665                 670

Tyr Thr Thr Leu Leu Phe Gly Thr Thr Ala Leu Asp Asp Thr Ala Trp
```

```
                    675                 680                 685
Phe Leu Val Glu Cys Phe His Leu Leu Ala Gly His Leu Leu Leu His
690                 695                 700

Asp Gly Leu Gln Asp Leu Ser Val Ala Pro Pro Ser Gly Gln Phe Ala
705                 710                 715                 720

Glu Met Ala Met Gln Met His Pro Ala Thr Gly Leu Ser Thr His Trp
                725                 730                 735

Ser Gln Val Asp Ser Pro Pro Leu Lys Leu Arg Glu Gly Ala Asn Met
            740                 745                 750

Val Val Leu Leu Gln Asp Gln Leu Leu Pro Met Ala Phe Ser Ile Ala
        755                 760                 765

Asn Val Cys Glu Asp Cys Ile Met Ala Tyr Met Ser Ala Ser Ala Ser
    770                 775                 780

Ser Val Leu Phe Tyr Thr Ser Cys Leu Asp Met Gln Gln Leu Pro Tyr
785                 790                 795                 800

Thr Gly His Val Ile Thr Ile Asn Lys Ser Glu Ala Ala Thr Ile
                805                 810                 815

<210> SEQ ID NO 26
<211> LENGTH: 813
<212> TYPE: PRT
<213> ORGANISM: Oryza sativa indica

<400> SEQUENCE: 26

Met Pro Ser Gly Gly Arg Arg Leu Pro Pro Trp Thr Ser Pro Arg Gly
1               5                   10                  15

Ala Ala Pro Arg Trp Ser Pro Cys Thr Pro Ala Gly Ala Asp Gly Ser
            20                  25                  30

Gly Arg Ala Ala His Ala Thr Pro Pro Ala Ser Gly Gly Cys Ser Ser
        35                  40                  45

His Val Thr Pro Pro Ala Ser Gly Gly Gly Cys Tyr Gly Tyr Arg
    50                  55                  60

Val Thr Pro Pro Thr Ser Gly Gly Cys Ser Arg Pro Pro Arg Ala Pro
65                  70                  75                  80

Leu Ser Ser Val Asp Ser Pro Tyr Val Arg Ala Lys Gln Ala Gln Val
                85                  90                  95

Ile Glu Lys Asp Pro Asn Lys Ala Val Pro Leu Phe Trp Ala Ala Ile
            100                 105                 110

Asn Ser Gly Asp Arg Ile Glu Ser Ala Leu Lys Asp Met Ala Thr Val
        115                 120                 125

Leu Lys Gln Ala Asn Arg Ala Glu Glu Ala Ile Glu Ala Ile Arg Ser
    130                 135                 140

Phe Arg Asp Arg Cys Pro Asn Glu Ala Gln Glu Ser Leu Asp Asn Ile
145                 150                 155                 160

Leu Leu Asp Leu Tyr Lys Lys Cys Gly Arg Thr Lys Glu Gln Ile Glu
                165                 170                 175

Met Leu Thr Leu Lys Leu Arg Ile Val Asp Glu Glu Leu Ala Ser Gly
            180                 185                 190

Arg Trp Lys Thr Lys Leu Ser Lys Ser His Gly Arg Val Val Tyr Leu
        195                 200                 205

Ser Leu Arg Asp Glu Lys Ala Arg Leu Leu Gly Asn Leu Ala Trp Ala
    210                 215                 220

His Met Gln Ser Glu Asn Tyr Asp Glu Ala Glu Met Leu Tyr Arg Gln
225                 230                 235                 240
```

```
Ala Leu Ala Ile Glu Ala Asp Tyr Asn Lys Glu Cys Asn Leu Ala Ile
                245                 250                 255

Cys Leu Ile Lys Thr Gly Lys Val Ala Glu Ala Lys Tyr Leu Leu Gln
            260                 265                 270

Ser Ile Pro Asp Asn Cys Ser Asp Glu Ser His Val Arg Ser Leu Ala
        275                 280                 285

Arg Ala Arg Glu Met Leu Met Glu Leu Glu Ser Pro Thr Leu His Ser
290                 295                 300

Pro Ile Thr Gln Met Lys Ser Lys Glu Ser Leu Ile Trp Leu Ala Ile
305                 310                 315                 320

Asp Ala Glu Asn Leu Gly His Leu Gln Pro Gln Val Ser Ser Thr Ala
                325                 330                 335

Leu Thr Gln Leu Lys Ser Glu Glu Pro His Ile Ser Val Ala Ala Asp
            340                 345                 350

Ala Glu Lys Gln Glu Asp Cys Asn Ser Gln Val Phe Pro Ser Pro Ile
        355                 360                 365

Thr Gln Met Lys Arg Glu Glu Pro Glu Ser Leu Ile Ala Thr Ser Gly
370                 375                 380

Glu Lys Asn Glu Lys Cys Leu Asn Glu Tyr Gln Asp Leu Ser Arg Leu
385                 390                 395                 400

Phe Asn Asp Ala Ala Thr Pro Gln Ser Leu Leu Glu Lys Leu Arg Lys
                405                 410                 415

Arg Leu Val Lys Glu Asp Thr Leu Asn Ile Ser Ile Gln His Gln Val
            420                 425                 430

Gln Ile Pro Ser Phe Val Glu Cys Leu Pro Asn Ser Gly Gly Ser Thr
        435                 440                 445

Asp Ala Gly Glu Asn Thr Arg Pro Glu Gly Lys Ala Leu Val Asn Gly
450                 455                 460

Val Arg Lys Thr Trp Ala Asp Met Val Glu Glu Asp Glu Arg Gln Leu
465                 470                 475                 480

Gly Asp Val Ser Ser Thr Ile Gly Met Asp Thr Thr Lys Arg Asn Val
                485                 490                 495

Ser Cys Lys His Ala Asn Glu Glu Met Tyr Arg Thr Pro Ser Phe Ser
            500                 505                 510

Gln Glu Ser Ser Ala Leu Lys Arg Ser Ser Val Asp Asp His Pro Gln
        515                 520                 525

Ser Ser Ser Ala Asp Ser Trp Arg His Ser Asp Ser Lys Ile Ser Thr
530                 535                 540

Asp Glu Asn Val Asn Met Lys Phe Val Arg Thr Ala Pro Gln Trp Arg
545                 550                 555                 560

Gln Lys Lys Val Gln Asp Tyr Ser Asn Arg Val Ser Gln Arg Leu Asp
                565                 570                 575

Thr Ser His Leu Ser Asp Arg Ala Glu Gly Thr Glu Gln Pro Pro Trp
            580                 585                 590

Arg Ser Ser Thr Ala Gln Arg Ser Leu Phe Pro Asp Trp Lys Ser Lys
        595                 600                 605

Cys Glu Arg Tyr Gly His Gly Tyr Val Pro Phe Cys Asp Asn Glu His
610                 615                 620

Phe Gln Gly Ser Ser His Phe Glu Ala Thr Asn Arg Trp Pro Lys Asn
625                 630                 635                 640

Ala Arg Pro Trp Arg Pro Gln Asn Arg Leu Trp Val Phe Gln Glu Ile
                645                 650                 655

Thr Asn Glu Ile Asn Gln Lys Gln Thr Arg Ala Leu Trp Leu Thr Ile
```

```
                    660                 665                 670
Tyr Thr Thr Leu Leu Phe Gly Thr Thr Ala Leu Asp Asp Thr Ala Trp
                675                 680                 685
Phe Leu Val Glu Cys Phe His Leu Leu Ala Gly His Leu Leu Leu His
            690                 695                 700
Asp Gly Leu Gln Asp Leu Ser Val Ala Pro Ser Gly Gln Phe Ala
705                 710                 715                 720
Glu Met Ala Met Gln Met His Pro Ala Thr Gly Leu Ser Thr His Trp
                725                 730                 735
Ser Gln Val Asp Ser Pro Leu Lys Leu Arg Glu Gly Ala Asn Met
            740                 745                 750
Val Val Leu Leu Gln Asp Gln Met Leu Pro Met Ala Phe Ser Ile Ala
                755                 760                 765
Asn Val Cys Glu Asp Cys Ile Met Ala Tyr Met Ser Ala Ser Ala Ser
            770                 775                 780
Ser Val Leu Phe Tyr Thr Ser Cys Leu Asp Met Gln Gln Leu Pro Tyr
785                 790                 795                 800
Thr Gly His Val Ile Thr Ile Asn Lys Ser Glu Thr Ala
                805                 810

<210> SEQ ID NO 27
<211> LENGTH: 685
<212> TYPE: PRT
<213> ORGANISM: Sorghum bicolor

<400> SEQUENCE: 27

Met Pro Ser Gly Gly Arg Arg Leu Pro Pro Trp Thr Ser Pro Arg Ser
1               5                   10                  15
Ala Gly Ala Gly Ala Ala Arg Trp Ser Pro Ala Ala Gly Thr Pro Ala
                20                  25                  30
Ala Ala Gly Gly Gln Arg Ser Gly Ser Gly Tyr Gly Thr Pro Pro Leu
            35                  40                  45
Ser Ala Gly Cys Phe Gly Thr Arg Val Thr Pro Pro Thr Ser Gly Gly
    50                  55                  60
Ala Arg Val Thr Pro Pro Ser Thr Gly Gly Cys Ser Ser Arg Pro Pro
65                  70                  75                  80
Arg Pro Pro Pro Ser Leu Asp Ser Pro Tyr Val Arg Ala Lys Gln Ala
                85                  90                  95
Gln Ile Val Glu Lys Asp Pro Asn Lys Ala Val Pro Leu Phe Trp Ala
                100                 105                 110
Ala Ile Asn Ser Gly Asp Arg Thr Glu Ser Ala Leu Lys Asp Met Ala
            115                 120                 125
Asn Val Leu Lys Gln Ala Asn Arg Ala Glu Glu Ala Ile Glu Ala Ile
        130                 135                 140
Arg Ser Phe Arg Asp Arg Cys Pro Tyr Glu Ala Gln Glu Ser Leu Asp
145                 150                 155                 160
Asn Ile Leu Leu Asp Leu Tyr Lys Lys Cys Gly Arg Thr Asp Glu Gln
                165                 170                 175
Ile Glu Met Leu Thr Ile Lys Leu Arg Ile Val Asp Glu Glu Leu Ala
            180                 185                 190
Ser Gly Arg Trp Lys Thr Lys Met Ser Lys Ser His Gly Arg Val Val
        195                 200                 205
Tyr Leu Ser Leu Arg Asp Glu Lys Ala Arg Leu Leu Gly Asn Leu Ala
    210                 215                 220
```

-continued

```
Trp Ala Tyr Met Gln Ser Glu Asn Tyr Glu Gly Ala Glu Met Leu Tyr
225                 230                 235                 240

Arg Gln Ala Leu Ala Ile Glu Ala Asp Tyr Asn Lys Glu Cys Asn Leu
                245                 250                 255

Ala Ile Cys Leu Met Lys Thr Gly Lys Val Ala Glu Ala Lys Tyr Leu
            260                 265                 270

Ile Gln Ala Ile Pro Tyr Asn Cys Asp Asp Glu Ser His Val Lys Ser
        275                 280                 285

Leu Ser Arg Ala Thr Glu Met Leu Arg Glu Leu Glu Leu Gln Ser Leu
    290                 295                 300

Pro Ser Pro Ile Thr Gln Ala Lys Ser Lys Glu Ser Gln Ile Phe Leu
305                 310                 315                 320

Ala Asp Asp Val Glu Met Leu Val Asp Leu Gln Pro Gln Thr Leu Ser
                325                 330                 335

Thr Pro Leu Ser Glu Leu Lys Tyr Lys Arg Pro His Ile Ser Val Ser
                340                 345                 350

Gln Asn Ala Glu Lys His Glu Asn Cys Asn Ser Trp Leu Pro Ser Pro
            355                 360                 365

Ile Thr Gln Leu Arg Arg Glu Glu Pro His Ile Met Val Thr Ala Gly
        370                 375                 380

Ala Glu Lys Asn Glu Ser Phe Ala Glu Phe Gln Asp Leu Ser Arg Leu
385                 390                 395                 400

Phe Asn Asp Ala Ala Thr Pro His Ser Ile Leu Glu Lys Leu Arg Lys
                405                 410                 415

Arg Leu Val Lys Glu Ala Pro Lys Ile Gly Ile His Asp Asp Gln Ile
                420                 425                 430

Gln Thr Pro Ile Pro Thr Glu Cys Leu Pro Asn Ser Glu Arg Asn Leu
            435                 440                 445

Asp Ala Ser Glu Thr Pro Met Gln Glu Gly Lys Leu Leu Thr Lys Gly
            450                 455                 460

Val Lys Lys Thr Trp Ala Asp Met Val Asp Glu Glu Gln Gln Leu
465                 470                 475                 480

Gly Asp Asp Lys Pro Leu Ala Asp Met Val Ala Lys Asp Glu Gln Gln
                485                 490                 495

Leu Gly Glu Ser Lys Ser Thr Leu Gly Val Gly Thr Thr Glu Gln Lys
            500                 505                 510

Glu Ser Ser Lys His Ala Ser Lys Leu Glu Tyr Arg Thr Pro Leu Ala
            515                 520                 525

Ser Gln Glu Ser Arg Thr His Gln Arg Pro Phe Met Gly Gly Gln Leu
    530                 535                 540

Gln Gly Ser Ser Ala Ala Ser Trp Arg Gln Asn Asp Ser Lys Ile Ser
545                 550                 555                 560

Met Asp Lys Asn Val Asn Arg Asp Leu Val Arg Thr Ala Pro Thr Trp
                565                 570                 575

Ser Lys His Lys Ala Gln Asp His Asn Asn Arg Val Trp Gln Arg Leu
            580                 585                 590

Asp Thr Val His Pro His Glu Arg Ala Ser Asp Thr Asn Gln Val Pro
            595                 600                 605

Arg Arg Ser Asn Thr Ser Gln Arg Ala Leu Phe Pro Asp Trp Lys Ser
        610                 615                 620

Lys Gly Glu Gly His Gly His Gly Cys Val Leu Phe Asp Asp Asn Glu
625                 630                 635                 640

Arg Thr Gln Cys Ser Ser His Val Glu Ala Thr His Arg Trp His Asn
```

645                 650                 655
Asn Glu Ala Ser Thr Gly Ser Trp Arg Pro Gln Asn Arg Leu Arg Val
            660                 665                 670

Phe Gln Glu Ile Thr Asn Glu Ile Asn Gln Asn Val Val
            675                 680                 685

<210> SEQ ID NO 28
<211> LENGTH: 690
<212> TYPE: PRT
<213> ORGANISM: Zea mays

<400> SEQUENCE: 28

Met Pro Ser Gly Gly Arg Arg Leu Pro Pro Trp Thr Ser Pro Arg Ser
1               5                   10                  15

Ala Gly Ala Pro Met Trp Ser Thr Ala Gly Thr Pro Gly Gly Pro Arg
            20                  25                  30

Pro Gly Pro Gly Tyr Gly Thr Pro Val Ser Ala Gly Cys Phe Gly
            35                  40                  45

Thr Arg Val Thr Pro Pro Thr Ser Gly Gly Thr Arg Val Thr Pro Pro
50                  55                  60

Thr Ser Gly Gly Ala Gly Ala Arg Val Thr Pro Pro Ser Thr Gly Gly
65                  70                  75                  80

Cys Ser Ser Arg Pro Pro Arg Pro Pro Ser Met Asp Ser Pro Tyr
                85                  90                  95

Val Arg Ala Lys Gln Ala Gln Ile Val Glu Lys Asp Pro Asn Lys Ala
            100                 105                 110

Val Pro Leu Phe Trp Ala Ala Ile Asn Ser Gly Asp Arg Ile Glu Ser
            115                 120                 125

Ala Leu Lys Asp Met Ala Asn Val Leu Lys Gln Ala Asn Arg Ser Glu
130                 135                 140

Glu Ala Ile Glu Ala Ile Arg Ser Phe Arg Asp Arg Cys Pro Tyr Glu
145                 150                 155                 160

Ala Gln Glu Ser Leu Asp Asn Ile Leu Leu Asp Leu Tyr Lys Lys Cys
                165                 170                 175

Gly Arg Thr Asp Glu Gln Ile Glu Met Leu Thr Leu Lys Leu Arg Ile
            180                 185                 190

Val Asp Glu Glu Leu Ala Ser Gly Arg Trp Lys Thr Lys Leu Ser Lys
            195                 200                 205

Ser His Gly Arg Val Val Tyr Leu Ser Leu Arg Asp Glu Lys Ala Arg
210                 215                 220

Leu Leu Gly Asn Leu Ala Trp Ala Tyr Met Gln Ser Glu Asn Tyr Glu
225                 230                 235                 240

Glu Ala Glu Met Leu Tyr Arg Gln Ala Leu Ala Ile Glu Ala Asp Tyr
                245                 250                 255

Asn Lys Glu Cys Asn Leu Ala Ile Cys Leu Met Lys Thr Gly Lys Leu
            260                 265                 270

Ala Glu Ala Lys Tyr Leu Ile His Ala Ile Pro Tyr Asn Cys Asn Asp
            275                 280                 285

Glu Ser His Val Lys Ser Leu Ser Arg Ala Thr Glu Met Leu Arg Glu
290                 295                 300

Phe Asp Leu Gln Ser Leu Pro Ser Pro Ile Thr Gln Ala Lys Ser Lys
305                 310                 315                 320

Glu Pro Arg Asn Phe Val Ala Asp Asp Val Glu Met Leu Val Asp Leu
                325                 330                 335

```
Gln Pro Gln Thr Leu Ser Thr Pro Phe Ser Glu Leu Lys Tyr Lys Glu
            340                 345                 350

Ala His Ile Ser Val Ser Gln Asn Ala Glu Lys His Glu Asn Cys Asn
        355                 360                 365

Ser Cys Leu Pro Ser Pro Ile Thr Gln Leu Arg Arg Glu Glu Pro His
    370                 375                 380

Thr Met Val Thr Ala Asp Ala Glu Lys Asn Glu Gly Phe Ala Glu Phe
385                 390                 395                 400

Gln Asp Leu Ser Arg Leu Phe Asn Asp Ala Ala Thr Pro His Ser Val
                405                 410                 415

Leu Glu Lys Leu Arg Lys Arg Leu Val Lys Glu Ala Pro Lys Val Ser
            420                 425                 430

Ile His Asp Gln Ile Gln Thr Pro Pro Thr Glu Ser Leu Pro Asn Ser
        435                 440                 445

Glu Arg Asn Leu Asp Ala Ser Glu Thr Ser Val Gln Glu Gly Lys Leu
    450                 455                 460

Leu Thr Lys Gly Val Arg Lys Thr Trp Ser Asp Met Val Asp Glu Glu
465                 470                 475                 480

Glu Gln Gln Leu Gly Asp Asp Lys Pro Trp Ala Asp Met Val Ala Lys
                485                 490                 495

Asp Asp Gln Gln Leu Gly Asp Gly Lys Ser Thr His Gly Val Gly Ile
            500                 505                 510

Thr Glu Gln Asn Glu Ser Ser Lys His Ala Ser Lys Leu Glu Tyr Arg
        515                 520                 525

Thr Pro Ser Ser Gln Glu Ser Arg Thr His Gln Arg Pro Val Met
    530                 535                 540

Gly Gly Gln Leu Gln Gly Ser Ser Ala Gly Ser Trp Arg Arg Ser Asp
545                 550                 555                 560

Ser Lys Ile Tyr Met Asp Lys Asn Val Asn Trp Asp Leu Val Arg Thr
                565                 570                 575

Ala Pro Thr Trp Ser Arg His Lys Val His Asp His Asn Asn Arg Val
            580                 585                 590

Trp Gln Arg Leu His Thr Ile His Pro Arg Glu Arg Ala Ser Gly Thr
        595                 600                 605

Lys Gln Val Pro Arg Arg Ser Asn Thr Ser Gln Arg Ala Leu Phe Pro
    610                 615                 620

Asp Trp Lys Ser Lys Gly Glu Gly Tyr Gly His Gly Tyr Val Pro Phe
625                 630                 635                 640

Asp Asp Asn Glu His Thr Gln Cys Ser Ser His Ile Glu Ala Ala Thr
                645                 650                 655

His Arg Trp His Asn Asn Glu Ala Ser Thr Gly Ser Trp Arg Pro Gln
            660                 665                 670

Asn Arg Leu Arg Val Phe Gln Glu Ile Thr Asn Glu Ile Asn Gln Asn
        675                 680                 685

Val Val
    690

<210> SEQ ID NO 29
<211> LENGTH: 362
<212> TYPE: PRT
<213> ORGANISM: Arabidopsis thaliana

<400> SEQUENCE: 29

Met Glu Gly Lys Phe Ala Ile Ser Glu Ser Thr Asn Leu Leu Gln Arg
1               5                   10                  15
```

```
Ile Lys Asp Phe Thr Gln Ser Val Val Asp Leu Ala Glu Gly Arg
         20                  25                  30

Ser Pro Lys Ile Ser Ile Asn Gln Phe Arg Asn Tyr Cys Met Asn Pro
         35                  40                  45

Glu Ala Asp Cys Leu Cys Ser Ser Asp Lys Pro Lys Gly Gln Glu Ile
 50                  55                  60

Phe Thr Leu Lys Lys Glu Pro Gln Thr Tyr Arg Ile Asp Met Leu Leu
 65                  70                  75                  80

Arg Val Leu Leu Ile Val Gln Gln Leu Leu Gln Glu Asn Arg His Ala
                 85                  90                  95

Ser Lys Arg Asp Ile Tyr Tyr Met His Pro Ser Ala Phe Lys Ala Gln
             100                 105                 110

Ser Ile Val Asp Arg Ala Ile Gly Asp Ile Cys Ile Leu Phe Gln Cys
             115                 120                 125

Ser Arg Tyr Asn Leu Asn Val Val Ser Val Gly Asn Gly Leu Val Met
             130                 135                 140

Gly Trp Leu Lys Phe Arg Glu Ala Gly Arg Lys Phe Asp Cys Leu Asn
145                 150                 155                 160

Ser Leu Asn Thr Ala Tyr Pro Val Pro Val Leu Val Glu Glu Val Glu
                 165                 170                 175

Asp Ile Val Ser Leu Ala Glu Tyr Ile Leu Val Val Glu Lys Glu Thr
             180                 185                 190

Val Phe Gln Arg Leu Ala Asn Asp Met Phe Cys Lys Thr Asn Arg Cys
             195                 200                 205

Ile Val Ile Thr Gly Arg Gly Tyr Pro Asp Val Ser Thr Arg Arg Phe
             210                 215                 220

Leu Arg Leu Leu Met Glu Lys Leu His Leu Pro Val His Cys Leu Val
225                 230                 235                 240

Asp Cys Asp Pro Tyr Gly Phe Glu Ile Leu Ala Thr Tyr Arg Phe Gly
                 245                 250                 255

Ser Met Gln Met Ala Tyr Asp Ile Glu Ser Leu Arg Ala Pro Asp Met
             260                 265                 270

Lys Trp Leu Gly Ala Phe Pro Ser Asp Ser Glu Val Tyr Ser Val Pro
             275                 280                 285

Lys Gln Cys Leu Leu Pro Leu Thr Glu Glu Asp Lys Lys Arg Thr Glu
    290                 295                 300

Ala Met Leu Leu Arg Cys Tyr Leu Lys Arg Glu Met Pro Gln Trp Arg
305                 310                 315                 320

Leu Glu Leu Glu Thr Met Leu Lys Arg Gly Val Lys Phe Glu Ile Glu
                 325                 330                 335

Ala Leu Ser Val His Ser Leu Ser Phe Leu Ser Glu Val Tyr Ile Pro
             340                 345                 350

Ser Lys Ile Arg Arg Glu Val Ser Ser Pro
    355                 360
```

<210> SEQ ID NO 30
<211> LENGTH: 383
<212> TYPE: PRT
<213> ORGANISM: Arabidopsis thaliana

<400> SEQUENCE: 30

```
Met Glu Glu Ser Ser Gly Leu Ser Ser Met Lys Phe Phe Ser Asp Gln
 1               5                  10                  15

His Leu Ser Tyr Ala Asp Ile Leu Leu Pro His Glu Ala Arg Ala Arg
```

```
            20                  25                  30
Ile Glu Val Ser Val Leu Asn Leu Leu Arg Ile Leu Asn Ser Pro Asp
             35                  40                  45
Pro Ala Ile Ser Asp Leu Ser Leu Ile Asn Arg Lys Arg Ser Asn Ser
 50                  55                  60
Cys Ile Asn Lys Gly Ile Leu Thr Asp Val Ser Tyr Ile Phe Leu Ser
 65                  70                  75                  80
Thr Ser Phe Thr Lys Ser Ser Leu Thr Asn Ala Lys Thr Ala Lys Ala
                 85                  90                  95
Phe Val Arg Val Trp Lys Val Met Glu Ile Cys Phe Gln Ile Leu Leu
                100                 105                 110
Gln Glu Lys Arg Val Thr Gln Arg Glu Leu Phe Tyr Lys Leu Leu Cys
                115                 120                 125
Asp Ser Pro Asp Tyr Phe Ser Ser Gln Ile Glu Val Asn Arg Ser Val
130                 135                 140
Gln Asp Val Val Ala Leu Leu Arg Cys Ser Arg Tyr Ser Leu Gly Ile
145                 150                 155                 160
Met Ala Ser Ser Arg Gly Leu Val Ala Gly Arg Leu Phe Leu Gln Glu
                165                 170                 175
Pro Gly Lys Glu Ala Val Asp Cys Ser Ala Cys Gly Ser Ser Gly Phe
                180                 185                 190
Ala Ile Thr Gly Asp Leu Asn Leu Leu Asp Asn Thr Ile Met Arg Thr
                195                 200                 205
Asp Ala Arg Tyr Ile Ile Ile Val Glu Lys His Ala Ile Phe His Arg
                210                 215                 220
Leu Val Glu Asp Arg Val Phe Asn His Ile Pro Cys Val Phe Ile Thr
225                 230                 235                 240
Ala Lys Gly Tyr Pro Asp Ile Ala Thr Arg Phe Phe Leu His Arg Met
                245                 250                 255
Ser Thr Thr Phe Pro Asp Leu Pro Ile Leu Val Leu Val Asp Trp Asn
                260                 265                 270
Pro Ala Gly Leu Ala Ile Leu Cys Thr Phe Lys Phe Gly Ser Ile Gly
                275                 280                 285
Met Gly Leu Glu Ala Tyr Arg Tyr Ala Cys Asn Val Lys Trp Ile Gly
                290                 295                 300
Leu Arg Gly Asp Asp Leu Asn Leu Ile Pro Glu Glu Ser Leu Val Pro
305                 310                 315                 320
Leu Lys Pro Lys Asp Ser Gln Ile Ala Lys Ser Leu Leu Ser Ser Lys
                325                 330                 335
Ile Leu Gln Glu Asn Tyr Ile Glu Glu Leu Ser Leu Met Val Gln Thr
                340                 345                 350
Gly Lys Arg Ala Glu Ile Glu Ala Leu Tyr Cys His Gly Tyr Asn Tyr
                355                 360                 365
Leu Gly Lys Tyr Ile Ala Thr Lys Ile Val Gln Gly Lys Tyr Ile
                370                 375                 380

<210> SEQ ID NO 31
<211> LENGTH: 1330
<212> TYPE: PRT
<213> ORGANISM: Arabidopsis thaliana

<400> SEQUENCE: 31

Met Phe Phe Gln His Ser Gln Leu Gln Asn Ser Asp His Leu Leu His
  1               5                  10                  15
```

-continued

```
Glu Ser Met Ala Asp Ser Asn His Gln Ser Leu Ser Pro Pro Cys Ala
         20                  25                  30

Asn Gly His Arg Ser Thr Ile Ser Leu Arg Asp Asp Gln Gly Gly Thr
             35                  40                  45

Phe Cys Leu Ile Cys Phe Ser Asn Leu Val Ser Asp Pro Arg Ile Pro
 50                  55                  60

Thr Val His Val Ser Tyr Ala Leu His Gln Leu Ser Ile Ala Ile Ser
 65                  70                  75                  80

Glu Pro Ile Phe Leu Arg Thr Leu Leu Ser His Ile His Phe Leu
                 85                  90                  95

Val Ser Pro Leu Val His Ala Leu Ser Ser Ile Asp Asp Ala Pro Ile
                100                 105                 110

Ala Ile Gln Ile Met Asp Met Ile Ser Leu Leu Cys Ser Val Glu Glu
            115                 120                 125

Ser Ser Ile Gly Glu Asp Phe Val Glu Arg Ile Ser Asp Gln Leu Ser
        130                 135                 140

Ser Gly Ala Leu Gly Trp Ser Arg Arg Gln Leu His Met Leu His Cys
145                 150                 155                 160

Phe Gly Val Leu Met Ser Cys Glu Asn Ile Asp Ile Asn Ser His Ile
                165                 170                 175

Arg Asp Lys Glu Ala Leu Val Cys Gln Leu Val Glu Gly Leu Gln Leu
            180                 185                 190

Pro Ser Glu Glu Ile Arg Gly Glu Ile Leu Phe Ala Leu Tyr Lys Phe
        195                 200                 205

Ser Ala Leu Gln Phe Thr Glu Gln Asn Val Asp Gly Ile Glu Val Leu
    210                 215                 220

Ser Leu Leu Cys Pro Lys Leu Leu Cys Leu Ser Leu Glu Ala Leu Ala
225                 230                 235                 240

Lys Thr Gln Arg Asp Asp Val Arg Leu Asn Cys Val Ala Leu Leu Thr
                245                 250                 255

Ile Leu Ala Gln Gln Gly Leu Leu Ala Asn Ser His Ser Asn Ser Ala
            260                 265                 270

Ser Ser Met Ser Leu Asp Glu Val Asp Asp Pro Met Gln Thr Ala
        275                 280                 285

Glu Asn Val Ala Ala Arg Pro Cys Leu Asn Val Leu Phe Ala Glu Ala
    290                 295                 300

Ile Lys Gly Pro Leu Leu Ser Thr Asp Ser Glu Val Gln Ile Lys Thr
305                 310                 315                 320

Leu Asp Leu Ile Phe His Tyr Ile Ser Gln Glu Ser Thr Pro Ser Lys
                325                 330                 335

Gln Ile Gln Val Met Val Glu Glu Asn Val Ala Asp Tyr Ile Phe Glu
            340                 345                 350

Ile Leu Arg Leu Ser Glu Cys Lys Asp Gln Val Val Asn Ser Cys Leu
        355                 360                 365

Arg Val Leu Asp Leu Phe Ser Leu Ala Glu His Ser Phe Arg Lys Arg
    370                 375                 380

Leu Val Ile Gly Phe Pro Ser Val Ile Arg Val Leu His Tyr Val Gly
385                 390                 395                 400

Glu Val Pro Cys His Pro Phe Gln Ile Gln Thr Leu Lys Leu Ile Ser
                405                 410                 415

Ser Cys Ile Ser Asp Phe Pro Gly Ile Ala Ser Ser Ser Gln Val Gln
            420                 425                 430

Glu Ile Ala Leu Val Leu Lys Lys Met Leu Glu Arg Tyr Tyr Ser Gln
```

```
            435                 440                 445
Glu Met Gly Leu Phe Pro Asp Ala Phe Ala Ile Ile Cys Ser Val Phe
450                 455                 460

Val Ser Leu Met Lys Thr Pro Ser Phe Gly Glu Thr Ala Asp Val Leu
465                 470                 475                 480

Thr Ser Leu Gln Glu Ser Leu Arg His Ser Ile Leu Ala Ser Leu Ser
                485                 490                 495

Leu Pro Glu Lys Asp Ser Thr Gln Ile Leu His Ala Val Tyr Leu Leu
            500                 505                 510

Asn Glu Ile Tyr Val Tyr Cys Thr Ala Ser Thr Ser Ile Asn Met Thr
            515                 520                 525

Ser Cys Ile Glu Leu Arg His Cys Val Ile Asp Val Cys Thr Ser His
530                 535                 540

Leu Leu Pro Trp Phe Leu Ser Asp Val Asn Val Asn Glu Glu Ala
545                 550                 555                 560

Thr Leu Gly Ile Met Glu Thr Phe His Ser Ile Leu Leu Gln Asn Ser
                565                 570                 575

Asp Ile Gln Ala Lys Glu Phe Ala Glu Leu Leu Val Ser Ala Asp Trp
            580                 585                 590

Phe Ser Phe Ser Phe Gly Cys Leu Gly Asn Phe Cys Thr Asp Asn Met
    595                 600                 605

Lys Gln Arg Ile Tyr Leu Met Leu Ser Ser Leu Val Asp Ile Leu Leu
            610                 615                 620

Glu Gln Lys Thr Gly Ser His Ile Arg Asp Ala Leu His Cys Leu Pro
625                 630                 635                 640

Ser Asp Pro Gln Asp Leu Leu Phe Leu Leu Gly Gln Ala Ser Ser Asn
                645                 650                 655

Asn Gln Glu Leu Ala Ser Cys Gln Ser Ala Ala Leu Leu Ile Phe His
            660                 665                 670

Thr Ser Ser Ile Tyr Asn Asp Arg Leu Ala Asp Asp Lys Leu Val Leu
            675                 680                 685

Ala Ser Leu Glu Gln Tyr Ile Ile Leu Asn Lys Thr Ser Leu Ile Cys
            690                 695                 700

Ala Ile Ser Asp Ser Pro Ala Leu Leu Asn Leu Val Asn Leu Tyr Gly
705                 710                 715                 720

Leu Cys Arg Ser Leu Gln Asn Glu Arg Tyr Gln Ile Ser Tyr Ser Leu
                725                 730                 735

Glu Ala Glu Arg Ile Ile Phe His Leu Leu Asn Glu Tyr Glu Trp Asp
            740                 745                 750

Leu Gly Ser Ile Asn Ile His Leu Glu Ser Leu Lys Trp Leu Phe Gln
    755                 760                 765

Gln Glu Ser Ile Ser Lys Ser Leu Ile Tyr Gln Ile Gln Lys Ile Ser
            770                 775                 780

Arg Asn Asn Leu Ile Gly Asn Glu Val His Asn Val Tyr Gly Asp Gly
785                 790                 795                 800

Arg Gln Arg Ser Leu Thr Tyr Trp Phe Ala Lys Leu Ile Ser Glu Gly
                805                 810                 815

Asp Asn Tyr Ala Ala Thr Leu Leu Val Asn Leu Leu Thr Gln Leu Ala
            820                 825                 830

Glu Lys Glu Glu Gln Glu Asn Asp Val Thr Ser Ile Leu Asn Leu Met
            835                 840                 845

Asn Thr Ile Val Ser Ile Phe Pro Thr Ala Ser Asn Asn Leu Ser Met
850                 855                 860
```

-continued

```
Asn Gly Ile Gly Ser Val Val His Arg Leu Val Ser Gly Phe Ser Asn
865                 870                 875                 880

Ser Ser Leu Gly Thr Ser Phe Lys Thr Leu Leu Leu Val Phe Asn
        885                 890                 895

Ile Leu Thr Ser Val Gln Pro Ala Val Leu Met Ile Asp Glu Ser Trp
            900                 905                 910

Tyr Ala Val Ser Ile Lys Leu Leu Asn Phe Leu Ser Leu Arg Asp Thr
            915                 920                 925

Ala Ile Lys Gln Asn His Glu Asp Met Val Val Ile Gly Ile Leu Ser
        930                 935                 940

Leu Val Leu Tyr His Ser Ser Asp Gly Ala Leu Val Glu Ala Ser Arg
945                 950                 955                 960

Asn Ile Val Ser Asn Ser Tyr Leu Val Ser Ala Ile Asn Thr Val Val
                965                 970                 975

Asp Val Ala Cys Ser Lys Gly Pro Ala Leu Thr Gln Cys Gln Asp Glu
            980                 985                 990

Thr Asn Ile Gly Glu Ala Leu Ala Phe Thr Leu Leu Leu Tyr Phe Phe
        995                 1000                1005

Ser Leu Arg Ser Leu Gln Ile Val Leu Ala Gly Ala Val Asp Trp
    1010                1015                1020

Gln Ala Phe Phe Gly Thr Ser Thr Ser Leu Glu Thr Leu Pro Val
    1025                1030                1035

Val Cys Ile Tyr Cys His Asn Leu Cys Arg Leu Met His Phe Gly
    1040                1045                1050

Ala Pro Gln Ile Lys Leu Ile Ala Ser Tyr Cys Leu Leu Glu Leu
    1055                1060                1065

Leu Thr Gly Leu Ser Glu Gln Val Asp Ile Lys Lys Glu Gln Leu
    1070                1075                1080

Gln Cys Ser Ser Ser Tyr Leu Lys Ser Met Lys Ala Val Leu Gly
    1085                1090                1095

Gly Leu Val Phe Cys Asp Asp Ile Arg Val Ala Thr Asn Ser Ala
    1100                1105                1110

Leu Cys Leu Ser Met Ile Leu Gly Trp Glu Asp Met Glu Gly Arg
    1115                1120                1125

Thr Glu Met Leu Lys Thr Ser Ser Trp Tyr Arg Phe Ile Ala Glu
    1130                1135                1140

Glu Met Ser Val Ser Leu Ala Leu Pro Cys Ser Ala Ser Ser Thr
    1145                1150                1155

Tyr Val Asn His His Lys Pro Ala Val Tyr Leu Thr Val Ala Met
    1160                1165                1170

Leu Arg Leu Lys Asn Lys Pro Val Trp Leu Arg Thr Val Phe Asp
    1175                1180                1185

Glu Ser Cys Ile Ser Ser Met Ile Gln Asn Leu Asn Gly Ile Asn
    1190                1195                1200

Ile Ser Arg Glu Ile Val Ile Leu Phe Arg Glu Leu Met Gln Ala
    1205                1210                1215

Glu Leu Leu Asn Ser Gln Gln Val Thr Lys Leu Asp Arg Ala Phe
    1220                1225                1230

Gln Glu Cys Arg Lys Gln Met His Arg Asn Gly Thr Arg Asp Glu
    1235                1240                1245

Thr Val Glu Glu Gln Val Gln Arg Lys Ile Pro Ser Ile His Asp
    1250                1255                1260
```

His Ser Glu Phe Cys Asn Tyr Leu Val His Leu Met Val Ser Asn
    1265                1270                1275

Ser Phe Gly His Pro Ser Glu Ser Glu Thr Tyr Thr Gln Lys Lys
    1280                1285                1290

Lys Gln Ile Leu Asp Glu Met Glu Gln Leu Ser Glu Leu Ile Ser
    1295                1300                1305

Thr Arg Glu Gly Arg Val Ser Pro Ile Gln Glu Glu Thr Arg Gln
    1310                1315                1320

Met Gln Thr Glu Arg Ile Val
    1325                1330

<210> SEQ ID NO 32
<211> LENGTH: 385
<212> TYPE: PRT
<213> ORGANISM: Arabidopsis thaliana

<400> SEQUENCE: 32

Met Ser Ser Ser Val Ala Glu Ala Asn His Thr Glu Lys Glu Ser
1                5                  10                  15

Leu Arg Leu Ala Ile Ala Val Ser Leu Leu Arg Ser Lys Phe Gln Asn
                20                  25                  30

His Gln Ser Ser Ser Ser Thr Ser Arg Cys Tyr Val Ser Glu Ser
                35                  40                  45

Asp Ala Leu Arg Trp Lys Gln Lys Ala Lys Glu Arg Lys Lys Glu Ile
50                  55                  60

Ile Arg Leu Gln Glu Asp Leu Lys Asp Ala Glu Ser Ser Phe His Arg
65                  70                  75                  80

Asp Leu Phe Pro Ala Asn Ala Ser Cys Lys Cys Tyr Phe Asp Asn
                85                  90                  95

Leu Gly Val Phe Ser Gly Arg Arg Ile Gly Glu Ala Ser Glu Ser Arg
                100                 105                 110

Phe Asn Asp Val Leu Arg Arg Arg Phe Leu Arg Leu Ala Cys Val Val
                115                 120                 125

Ile Leu Ser Leu Ala Arg Arg Arg Ser Arg Arg Lys Leu Thr Arg Ser
130                 135                 140

Ser Gln Arg Leu Gln Pro Ser Glu Pro Asp Tyr Glu Glu Glu Ala Glu
145                 150                 155                 160

His Leu Arg Ile Ser Ile Asp Phe Leu Leu Glu Leu Ser Glu Ala Asp
                165                 170                 175

Ser Asn Asp Ser Asn Phe Ser Asn Trp Ser His Gln Ala Val Asp Phe
                180                 185                 190

Ile Phe Ala Ser Leu Lys Lys Leu Ile Ser Met Gly Arg Asn Leu Glu
                195                 200                 205

Ser Val Glu Glu Ser Ile Ser Phe Met Ile Thr Gln Leu Ile Thr Arg
210                 215                 220

Met Cys Thr Pro Val Lys Gly Asn Glu Val Lys Gln Leu Glu Thr Ser
225                 230                 235                 240

Val Gly Phe Tyr Val Gln His Leu Ile Arg Lys Leu Gly Ser Glu Pro
                245                 250                 255

Phe Ile Gly Gln Arg Ala Ile Phe Ala Ile Ser Gln Arg Ile Ser Ile
                260                 265                 270

Leu Ala Glu Asn Leu Leu Phe Met Asp Pro Phe Asp Glu Ser Phe Pro
                275                 280                 285

Glu Met Asp Glu Cys Met Phe Ile Leu Ile Gln Leu Ile Glu Phe Leu
                290                 295                 300

Ile Cys Asp Tyr Leu Leu Pro Trp Ala Asn Glu Ala Phe Asp Asn Val
305                 310                 315                 320

Met Phe Glu Glu Trp Ile Ala Ser Val Val His Ala Arg Lys Ala Val
            325                 330                 335

Lys Ala Leu Glu Glu Arg Asn Gly Leu Tyr Leu Leu Tyr Met Asp Arg
            340                 345                 350

Val Thr Gly Glu Leu Ala Lys Arg Val Gly Gln Ile Thr Ser Phe Arg
            355                 360                 365

Glu Val Glu Pro Ala Ile Leu Asp Lys Ile Leu Ala Tyr Gln Glu Ile
            370                 375                 380

Glu
385

<210> SEQ ID NO 33
<211> LENGTH: 449
<212> TYPE: PRT
<213> ORGANISM: Arabidopsis thaliana

<400> SEQUENCE: 33

Met Lys Met Asn Ile Asn Lys Ala Cys Asp Leu Lys Ser Ile Ser Val
1               5                   10                  15

Phe Pro Pro Asn Leu Arg Arg Ser Ala Glu Pro Gln Ala Ser Gln Gln
            20                  25                  30

Leu Arg Ser Gln Gln Ser Gln Ser Phe Ser Gln Gly Pro Ser Ser
            35                  40                  45

Ser Gln Arg Gly Cys Gly Gly Phe Ser Gln Met Thr Gln Ser Ser Ile
50                  55                  60

Asp Glu Leu Leu Ile Asn Asp Gln Arg Phe Ser Ser Gln Glu Arg Asp
65                  70                  75                  80

Leu Ser Leu Lys Lys Val Ser Ser Cys Leu Pro Pro Ile Asn His Lys
                85                  90                  95

Arg Glu Asp Ser Gln Leu Val Ala Ser Arg Ser Ser Gly Leu Ser
            100                 105                 110

Arg Arg Trp Ser Ser Ala Ser Ile Gly Glu Ser Lys Ser Gln Ile Ser
            115                 120                 125

Glu Glu Leu Glu Gln Arg Phe Gly Met Met Glu Thr Ser Leu Ser Arg
130                 135                 140

Phe Gly Met Met Leu Asp Ser Ile Gln Ser Asp Ile Met Gln Ala Asn
145                 150                 155                 160

Arg Gly Thr Lys Glu Val Phe Leu Glu Thr Glu Arg Ile Gln Gln Lys
                165                 170                 175

Leu Thr Leu Gln Asp Thr Ser Leu Gln Gln Leu Arg Lys Glu Gln Ala
            180                 185                 190

Asp Ser Lys Ala Ser Leu Asp Gly Gly Val Lys Phe Ile Leu Glu Glu
            195                 200                 205

Phe Ser Lys Asp Pro Asn Gln Glu Lys Leu Gln Lys Ile Leu Gln Met
            210                 215                 220

Leu Thr Thr Ile Pro Glu Gln Val Glu Thr Ala Leu Gln Lys Ile Gln
225                 230                 235                 240

Arg Glu Ile Cys His Thr Phe Thr Arg Glu Ile Gln Val Leu Ala Ser
                245                 250                 255

Leu Arg Thr Pro Glu Pro Arg Val Arg Val Pro Thr Ala Pro Gln Val
            260                 265                 270

Lys Ala Lys Glu Asn Leu Pro Glu Gln Arg Gly Gln Ala Ala Lys Val

```
                275                 280                 285
Leu Thr Ser Leu Lys Met Pro Glu Pro Arg Val Gln Val Pro Ala Ala
290                 295                 300

Pro Gln Ala Lys Glu Asn Phe Pro Glu Gln Arg Gly Pro Val Ala Lys
305                 310                 315                 320

Ser Asn Ser Phe Cys Asn Thr Thr Leu Lys Thr Lys Gln Pro Gln Phe
                325                 330                 335

Pro Arg Asn Pro Asn Asp Ala Ser Ala Arg Ala Val Lys Pro Tyr Leu
                340                 345                 350

Ser Pro Lys Ile Gln Val Gly Cys Trp Lys Thr Val Lys Pro Glu Lys
                355                 360                 365

Ser Asn Phe Lys Lys Arg Ala Thr Arg Lys Pro Val Lys Ser Glu Ser
                370                 375                 380

Thr Arg Thr Gln Phe Glu Gln Cys Ser Val Val Ile Asp Ser Asp Glu
385                 390                 395                 400

Glu Asp Ile Asp Gly Gly Phe Ser Cys Leu Ile Asn Glu Asn Thr Arg
                    405                 410                 415

Gly Thr Asn Phe Glu Trp Asp Ala Glu Lys Glu Thr Glu Arg Ile Leu
                420                 425                 430

Arg Thr Ala Arg Arg Thr Lys Arg Lys Phe Gly Asn Pro Ile Ile Ile
                435                 440                 445

Asn

<210> SEQ ID NO 34
<211> LENGTH: 233
<212> TYPE: PRT
<213> ORGANISM: Arabidopsis thaliana

<400> SEQUENCE: 34

Met Arg His Asn Ile Lys Phe Lys Ser Lys Gly Thr Leu Lys Ile Arg
1               5                   10                  15

Asn Thr Ala Gln Ile Ser Leu Trp Lys Lys Cys Ser Asp Ser Met Ile
                20                  25                  30

Ala Asp Gln Thr Tyr Leu Phe Ile Asn Arg Val Gln Asp Arg Arg Phe
            35                  40                  45

Asp Glu Glu Ser Leu Arg Ile Leu Glu Leu Ser Leu Val Ala Met Asn
        50                  55                  60

Val Lys Ser Phe Leu Glu Val Arg Ser Arg Leu Arg Asp Phe Met Arg
65                  70                  75                  80

Ser Glu Ser Val Val Ile Phe Gly Glu Leu Thr Gly Glu Ser Met Val
                85                  90                  95

Ala Lys Leu Ser Val Leu Glu Phe Phe Ala Arg Ala Phe Ala Leu Leu
            100                 105                 110

Gly Asp Met Glu Ser Cys Leu Ala Met Arg Tyr Glu Ala Leu Asn Leu
        115                 120                 125

Arg Gln Leu Lys Ser Pro Ser Cys Leu Trp Leu Gly Val Ser His Ser
    130                 135                 140

Glu Trp Thr Lys Phe Ala Val Gln Ser Met Glu Asn Gly Phe Pro Ser
145                 150                 155                 160

Ile Ala Gly Lys Ala Ser Glu Asn Ala Leu Leu Ser Leu Lys Lys Asp
                165                 170                 175

Ser Leu Ile Glu Pro Lys Ser Glu Asp Asn Ser Asp Ile Leu Asp Ala
            180                 185                 190

Ala Glu Lys Val Arg Arg Leu Arg Asp Ser Ala Ala Ser Leu Thr Ser
```

```
              195                 200                 205
Ser His Ser Gly Ile Phe Ile Tyr Ile Val Ser Ser Leu Lys Phe Ala
    210                 215                 220

Val Cys Asn Arg Leu Leu Thr Thr Phe
225                 230

<210> SEQ ID NO 35
<211> LENGTH: 617
<212> TYPE: PRT
<213> ORGANISM: Arabidopsis thaliana

<400> SEQUENCE: 35

Met Phe Tyr Ser His Gln Leu Leu Ala Arg Lys Ala Pro Leu Gly Gln
1               5                   10                  15

Ile Trp Met Ala Ala Thr Leu His Ala Lys Ile Asn Arg Lys Lys Leu
                20                  25                  30

Asp Lys Leu Asp Ile Ile Gln Ile Cys Glu Glu Ile Leu Asn Pro Ser
            35                  40                  45

Val Pro Met Ala Leu Arg Leu Ser Gly Ile Leu Met Gly Gly Val Val
        50                  55                  60

Ile Val Tyr Glu Arg Lys Val Lys Leu Leu Phe Asp Asp Val Asn Arg
65                  70                  75                  80

Phe Leu Val Glu Ile Asn Gly Ala Trp Arg Thr Lys Ser Val Pro Asp
                85                  90                  95

Pro Thr Leu Leu Pro Lys Gly Lys Thr His Ala Arg Lys Glu Ala Val
            100                 105                 110

Thr Leu Pro Glu Asn Glu Glu Ala Asp Phe Gly Asp Phe Glu Gln Thr
        115                 120                 125

Arg Asn Val Pro Lys Phe Gly Asn Tyr Met Asp Phe Gln Gln Thr Phe
    130                 135                 140

Ile Ser Met Arg Leu Asp Glu Ser His Val Asn Asn Pro Glu Pro
145                 150                 155                 160

Glu Asp Leu Gly Gln Gln Phe His Gln Ala Asp Ala Glu Asn Ile Thr
                165                 170                 175

Leu Phe Glu Tyr His Gly Ser Phe Gln Thr Asn Asn Glu Thr Tyr Asp
            180                 185                 190

Arg Phe Glu Arg Phe Asp Ile Glu Gly Asp Asp Glu Thr Gln Met Asn
        195                 200                 205

Ser Asn Pro Arg Glu Gly Ala Glu Ile Pro Thr Thr Leu Ile Pro Ser
    210                 215                 220

Pro Pro Arg His His Asp Ile Pro Glu Gly Val Asn Pro Thr Ser Pro
225                 230                 235                 240

Gln Arg Gln Glu Gln Glu Asn Arg Arg Asp Gly Phe Ala Glu Gln
                245                 250                 255

Met Glu Glu Gln Asn Ile Pro Asp Lys Glu Glu His Asp Arg Pro Gln
            260                 265                 270

Pro Ala Lys Lys Arg Ala Arg Lys Thr Ala Thr Ser Ala Met Asp Tyr
        275                 280                 285

Glu Gln Thr Ile Ile Ala Gly His Val Tyr Gln Ser Trp Leu Gln Asp
    290                 295                 300

Thr Ser Asp Ile Leu Cys Arg Gly Glu Lys Arg Lys Val Arg Gly Thr
305                 310                 315                 320

Ile Arg Pro Asp Met Glu Ser Phe Lys Arg Ala Asn Met Pro Pro Thr
                325                 330                 335
```

-continued

```
Gln Leu Phe Glu Lys Asp Ser Ser Tyr Pro Pro Gln Leu Tyr Gln Leu
                340                 345                 350

Trp Ser Lys Asn Thr Gln Val Leu Gln Thr Ser Ser Glu Ser Arg
            355                 360                 365

His Pro Asp Leu Arg Ala Glu Gln Ser Pro Gly Phe Val Gln Glu Arg
        370                 375                 380

Met His Asn His His Gln Thr Asp His His Glu Arg Ser Asp Thr Ser
385                 390                 395                 400

Ser Gln Asn Leu Asp Ser Pro Ala Glu Ile Leu Arg Thr Val Arg Thr
                405                 410                 415

Gly Lys Gly Ala Ser Val Glu Ser Met Met Ala Gly Ser Arg Ala Ser
            420                 425                 430

Pro Glu Thr Ile Asn Arg Gln Ala Ala Asp Ile Asn Val Thr Pro Phe
        435                 440                 445

Tyr Ser Gly Asp Asp Val Arg Ser Met Pro Ser Thr Pro Ser Ala Arg
    450                 455                 460

Gly Ala Ala Ser Ile Asn Asn Ile Glu Ile Ser Ser Lys Ser Arg Met
465                 470                 475                 480

Pro Asn Arg Lys Arg Pro Asn Ser Ser Pro Arg Arg Gly Leu Glu Pro
                485                 490                 495

Val Ala Glu Glu Arg Pro Trp Glu His Arg Glu Tyr Glu Phe Glu Phe
            500                 505                 510

Ser Met Leu Pro Glu Lys Arg Phe Thr Ala Asp Lys Glu Ile Leu Phe
        515                 520                 525

Glu Thr Ala Ser Thr Gln Thr Gln Lys Pro Val Cys Asn Gln Ser Asp
    530                 535                 540

Glu Met Ile Thr Asp Ser Ile Lys Ser His Leu Lys Thr His Phe Glu
545                 550                 555                 560

Thr Pro Gly Ala Pro Gln Val Glu Ser Leu Asn Lys Leu Ala Val Gly
                565                 570                 575

Met Asp Arg Asn Ala Ala Ala Lys Leu Phe Phe Gln Ser Cys Val Leu
            580                 585                 590

Ala Thr Arg Gly Val Ile Lys Val Asn Gln Ala Glu Pro Tyr Gly Asp
        595                 600                 605

Ile Leu Ile Ala Arg Gly Pro Asn Met
    610                 615
```

<210> SEQ ID NO 36
<211> LENGTH: 21
<212> TYPE: DNA
<213> ORGANISM: artificial sequence
<220> FEATURE:
<223> OTHER INFORMATION: synthetic primer

<400> SEQUENCE: 36
gacatcggca cttgcttaga g                                              21

<210> SEQ ID NO 37
<211> LENGTH: 21
<212> TYPE: DNA
<213> ORGANISM: artificial sequence
<220> FEATURE:
<223> OTHER INFORMATION: synthetic primer

<400> SEQUENCE: 37
gcgatatagc tcccactggt t                                              21

```
<210> SEQ ID NO 38
<211> LENGTH: 31
<212> TYPE: DNA
<213> ORGANISM: artificial sequence
<220> FEATURE:
<223> OTHER INFORMATION: synthetic primer

<400> SEQUENCE: 38
gagtttacta tactctgccg ccggcgagaa c                              31

<210> SEQ ID NO 39
<211> LENGTH: 38
<212> TYPE: DNA
<213> ORGANISM: artificial sequence
<220> FEATURE:
<223> OTHER INFORMATION: synthetic primer

<400> SEQUENCE: 39
ctccacctgg agtttactat gccccgccgc cggcgaga                       38

<210> SEQ ID NO 40
<211> LENGTH: 32
<212> TYPE: DNA
<213> ORGANISM: artificial sequence
<220> FEATURE:
<223> OTHER INFORMATION: synthetic primer

<400> SEQUENCE: 40
ccacctggag ttgcgtatac tccgccgcgg cg                             32

<210> SEQ ID NO 41
<211> LENGTH: 35
<212> TYPE: DNA
<213> ORGANISM: artificial sequence
<220> FEATURE:
<223> OTHER INFORMATION: synthetic primer

<400> SEQUENCE: 41
ccacctggag ttgcgagaac aagtgatcat gtggc                          35
```